(12) United States Patent
Scherman et al.

(10) Patent No.: US 11,491,227 B2
(45) Date of Patent: Nov. 8, 2022

(54) CUCURBITURIL-BASED HYDROGELS

(71) Applicant: CAMBRIDGE ENTERPRISE LIMITED, Cambridge (GB)

(72) Inventors: Oren Scherman, Cambridge (GB); Eric Appel, Los Alamitos, CA (US); Xian Jun Loh, Singapore (SG); Frank Biedermann, Halle (DE); Matthew Rowland, Cambridge (GB)

(73) Assignee: CAMBRIDGE ENTERPRISE LIMITED, Cambridge (GB)

( * ) Notice: Subject to any disclaimer, the term of this patent is extended or adjusted under 35 U.S.C. 154(b) by 339 days.

(21) Appl. No.: 14/379,109

(22) PCT Filed: Feb. 20, 2013

(86) PCT No.: PCT/GB2013/050414
§ 371 (c)(1),
(2) Date: Aug. 15, 2014

(87) PCT Pub. No.: WO2013/124654
PCT Pub. Date: Aug. 29, 2013

(65) Prior Publication Data
US 2015/0110772 A1 Apr. 23, 2015

(30) Foreign Application Priority Data

Feb. 20, 2012 (GB) .................................. 1202834
Jan. 30, 2013 (GB) .................................. 1301648

(51) Int. Cl.
*A61K 47/32* (2006.01)
*A61K 38/38* (2006.01)
*A61K 38/47* (2006.01)
*C08L 39/00* (2006.01)
*C08J 3/075* (2006.01)
*C08B 11/12* (2006.01)
*C08G 18/71* (2006.01)
*C08L 1/02* (2006.01)
*C08B 11/08* (2006.01)
*C08J 3/24* (2006.01)
*C08B 37/08* (2006.01)
*C08L 5/08* (2006.01)
*C08L 5/16* (2006.01)
*C08L 1/28* (2006.01)
*C08G 18/64* (2006.01)
*C08B 37/16* (2006.01)

(52) U.S. Cl.
CPC ............ *A61K 47/32* (2013.01); *A61K 38/385* (2013.01); *A61K 38/47* (2013.01); *C08B 11/08* (2013.01); *C08B 11/12* (2013.01); *C08B 37/0015* (2013.01); *C08B 37/0072* (2013.01); *C08G 18/6484* (2013.01); *C08G 18/71* (2013.01); *C08J 3/075* (2013.01); *C08J 3/246* (2013.01); *C08L 1/02* (2013.01); *C08L 1/284* (2013.01); *C08L 1/286* (2013.01); *C08L 5/08* (2013.01); *C08L 5/16* (2013.01); *C08L 39/00* (2013.01); *C08G 2210/00* (2013.01); *C08J 2300/10* (2013.01); *C08J 2300/204* (2013.01); *C08J 2300/208* (2013.01); *C08J 2300/21* (2013.01); *C08J 2301/28* (2013.01); *C08J 2305/08* (2013.01); *C08J 2305/16* (2013.01); *C08J 2329/04* (2013.01); *C08J 2375/02* (2013.01); *C12Y 302/01017* (2013.01)

(58) Field of Classification Search
None
See application file for complete search history.

(56) References Cited

U.S. PATENT DOCUMENTS

| | | | |
|---|---|---|---|
| 6,911,572 B1 | 6/2005 | Bruhn et al. | |
| 7,060,498 B1 | 6/2006 | Wang | |
| 8,378,059 B2 | 2/2013 | Rauwald et al. | |
| 2002/0133003 A1 | 9/2002 | Kim et al. | |
| 2004/0247680 A1 | 12/2004 | Farokhzad et al. | |
| 2005/0250551 A1 | 11/2005 | Helle | |
| 2005/0250881 A1 | 11/2005 | Gref et al. | |
| 2006/0154254 A1 | 7/2006 | Kim et al. | |
| 2006/0292570 A1 | 12/2006 | Keinan | |
| 2010/0247477 A1 | 9/2010 | Rauwald et al. | |
| 2010/0254890 A1 | 10/2010 | Yang et al. | |

(Continued)

FOREIGN PATENT DOCUMENTS

| | | |
|---|---|---|
| JP | 2007-211060 A | 8/2007 |
| WO | 99/064485 A1 | 12/1999 |
| WO | 05/023816 A2 | 3/2005 |

(Continued)

OTHER PUBLICATIONS

Li et al. (Biomaterials 27 (2006) 4132-4140).*
Kwok et al. (Polymer 44 (2003) 7335-7344.*
Schwall et al. (Materials 2009, 2, 577-612).*
Hoare et al. (Polymer 49 (2008) 1993-2007.*
Coulston et al. "Supramolecular gold nanoparticle-polymer composites formed in water with cucurbit[8]uril". Chem. Comm. vol. 47, pp. 164-166, 2011.
Esposito et al. "Comparative analysis of tetracycline-containing dental gels: poloxamer- and monoglyceride-based formulations". International Journal of Pharmaceutics. vol. 142, pp. 9-23, 1996.
Estroff et al. "Water Gelation by Small Organic Molecules". Chem. Rev. vol. 104, No. 3, pp. 1201-1217, 2004.
Greenfield et al. "Tunable Mechanics of Peptide Nanofiber Gels". Langmuir. vol. 26, No. 5, pp. 3641-3647, 2010.

(Continued)

*Primary Examiner* — Patricia Duffy
*Assistant Examiner* — Garen Gotfredson
(74) *Attorney, Agent, or Firm* — Oliff PLC

(57) ABSTRACT

The invention provides hydrogel, wherein the hydrogel has a supramolecular cross-linked network obtainable or obtained from the complexation of an aqueous composition including a host, such as cucurbituril, and one or more polymers having suitable guest functionality. One or more polymers in the aqueous composition may have a molecular weight of 50 kDa or more, such as 200 kDa or more. The hydrogel may hold a component, such as a therapeutic compound or a biological molecule. The hydrogels are suitable for use in medicine.

8 Claims, 22 Drawing Sheets

(56) References Cited

U.S. PATENT DOCUMENTS

2015/0202299 A1\* 7/2015 Burdick ............... A61L 31/042
424/85.2

FOREIGN PATENT DOCUMENTS

| WO | 05/112890 A1 | 12/2005 |
|---|---|---|
| WO | 07/046575 A1 | 4/2007 |
| WO | 07/106144 A1 | 9/2007 |
| WO | 08/096360 A2 | 8/2008 |
| WO | 09/071899 A2 | 6/2009 |
| WO | 11/077099 A2 | 6/2011 |
| WO | 13/014452 A1 | 1/2013 |

OTHER PUBLICATIONS

Hartgerink et al. "Self-Assembly and Mineralization of Peptide-Amphiphile Nanofibers". Science. vol. 294, pp. 1684-1688, Nov. 23, 2001.
Heitmann et al. "Sequence-Specific Recognition and Cooperative Dimerization of N-Terminal Aromatic Peptides in Aqueous Solution by a Synthetic Host". J. Am. Chem. Soc. vol. 128, pp. 12574-12581, 2006.
Horkay et al. "Macroscopic and Microscopic Thermodynamic Observations in Swollen Poly(vinyl acetate) Networks". Macromolecules. vol. 24, pp. 2896-2902, 1991.
Horkay et al. "Structural investigations of a neutralized polyelectrolyte gel and an associating neutral hydrogel". Polymer. vol. 46, pp. 4242-4247, 2005.
Hunt et al. "Tunable, High Modulus Hydrogels Driven by Ionic Coacervation". Adv. Mater. vol. 23, pp. 2327-2331, 2011.
Katakam et al. "Controlled release of human growth hormone following subcutaneous administration in dogs". Int. J. Pharm. vol. 152, pp. 53-58, 1997.
Koopmans et al. "Formation of Physical Hydrogels via Host-Guest Interactions of b-Cyclodextrin Polymers and Copolymers Bearing Adamantyl Groups". Macromolecules. vol. 41, pp. 7418-7422, 2008.
Kretschmann et al. "Switchable Hydrogels Obtained by Supramolecular Cross-Linking of Adamantyl-Containing LCST Copolymers with Cyclodextrin Dimers". Angew. Chem. Int. Edit. vol. 45, pp. 4361-4365, 2006.
Richard et al. "Analysis and Visualisation of Neutron-Scattering Data". J. Neutron Research. vol. 4, pp. 33-39, 1996.
Lee et al. "Unprecedented host-induced intramolecular charge-transfer complex formation". Chem. Comm. pp. 2692-2693, 2002. The Royal Soc. of Chem.
Li et al. "Poly(ester urethane)s Consisting of Poly[(R)-3-hydroxybutyrate] and Poly(ethylene glycol) as Candidate Biomaterials: Characterization and Mechanical Property Study". Biomacromolecules. vol. 6, pp. 2740-2747, 2005.
Loh et al. "Micellization and Thermogelation of Poly(ether urethane)s Comprising Poly(ethylene glycol) and Poly(propylene glycol)". Macromol. Symp. vol. 296, pp. 161-169, 2010.
Loh et al. "Biodegradable Thermogelling Poly[(R)-3-hydroxybutyrate]-Based Block Copolymers: Micellization, Gelation, and Cytotoxicity and Cell Culture Studies". J. Phys. Chem. B. vol. 113, pp. 11822-11830, 2009.
Loh et al. "Hydrolytic degradation and protein release studies of thermogelling polyurethane copolymers consisting of poly[(R)]-3-hydroxybutyrate], poly(ethylene glycol), and poly(propylene glycol)". Biomaterials. vol. 28, pp. 4113-4123, 2007.
Loh et al. "Biodegradable thermogelling poly(ester urethane)s consisting of poly(lactic acid)—Thermodynamics of micellization and hydrolytic degradation". Biomaterials. vol. 29, pp. 2164-2172, 2008.
Loh et al. "Synthesis and water-swelling of thermo-responsive poly(ester urethane)s containing poly(?-caprolactone), poly(ethylene glycol) and poly(propylene glycol)". Biomaterials. vol. 29, pp. 3185-3194, 2008.
Loh et al. "Controlled drug release from biodegradable thermoresponsive physical hydrogel nanofibers". J. Contol. Release. vol. 143, pp. 175-182, 2010.
Loh et al. "Encapsulation of basic fibroblast growth factor in thermogelling copolymers preserves its bioactivity." J. Mater. Chem. vol. 21, pp. 2246-2254, 2011.
Lutolf, Matthias. "Spotlight on hydrogels". Nature Materials. vol. 8, pp. 451-453, Jun. 2009.
Mynar et al. "The gift of healing". Nature. vol. 451, pp. 895-896, Feb. 2008.
Nakamura et al. "Supramolecular Catalysis of the Enantiodifferentiating [4+4] Photocyclodimerization of 2-Anthracenecarboxylate by ?-Cyclodextrin". J. Am. Chem. Soc. vol. 125, pp. 966-972, 2003.
Nochi et al. "Nanogel antigenic protein-delivery system for adjuvant-free intranasal vaccines". Nat. Mat. vol. 9, pp. 572-578, Jun. 20, 2010.
Peppas et al. "Physicochemical Foundations and Structural Design of Hydrogels in Medicine and Biology". Annu. Rev. Biomed. Eng. vol. 2, pp. 9-29, 2000.
Pezron et al. "Conformation of gelatin chains in aqueous solutions: 1. A light and small-angle neutron scattering study". Polymer. vol. 32 No. 17, pp. 3201-3210, 1991.
Reczek et al. "Multivalent Recognition of Peptides by Modular Self-Assembled Receptors". J. Am. Chem. Soc. vol. 131, pp. 2408-2415, 2009.
Ritger et al. "A Simple Equation for Description of Solute Release I. Fickian and Non-Fickian Release from Non-Swellable Devices in the form of Slabs, Spheres, Cyclinders or Discs". Journal of Contorlled Release. vol. 5, pp. 23-36, 1987.
Ritger et al. "A Simple Equation for Description of Solute Release II. Fickian and Anomalous Release from Swellable Devices". Journal of Controlled Release. vol. 5, pp. 37-42, 1987.
Staats et al. "Chaperoning vaccines". Nat. Mat. vol. 9, pp. 537-538, Jul. 2010.
Tamaki et al. "Reversible Photodimerization of Water-Soluble Anthracenes included in ?-Cyclodextrin." Chem. Lett. pp. 53-56, 1984.
Uzunova et al. "Toxicity of cucurbit[7]uril and cucurbit[8]uril: an explanatory in vitro and in vivo study". Org. Biomol. Chem. vol. 8 No. 9, pp. 2037-2042, May 7, 2010.
Van Tomme et al. "Self-gelling hydrogels based on oppositely charged dextran microspheres". Biomaterials. vol. 26, pp. 2129-2135, 2005.
Wang et al. "High-water-content mouldable hydrogels by mixing clay and a dendritic molecular binder". Nature. vol. 463, pp. 339-343, Jan. 21, 2010.
Wojtecki et al. "Using the dynamic bond to access macroscopically responsive structurally dynamic polymers". Nat. Mat. vol. 10, pp. 14-27, 2011.
Wu et al. "Fabrication of Supramolecular Hydrogels for Drug Delivery and Stem Cell Encapsulation". Langmuir. vol. 24, pp. 10306-10312, 2008.
Yang et al. "Highly Stereoselective Photocyclodimerization of ?-Cyclodextrin-Appended Anthracene Mediated by ?-Cyclodextrin and Cucurbit[8]uril: A Dramatic Steric Effect Operating Outside the Binfing Site". J. Am. Chem. Soc. vol. 130, pp. 8574-8575, 2008.
Jun. 20, 2013 International Search Report and Written Opinion issued in International Application No. PCT/GB2013/050414.
May 14, 2012 Search Report issued in Great Britain Application No. GB1202834.6.
Huang et al. "Fabrication of cucurbit[6]uril mediated alginate physical hydrogel beads and their application as a drug carriers". e-Polymers. vol. 95, pp. 1-11, 2008.
Park et al. "In Situ Supramolecular Assembly and Modular Modification of Hyaluronic Acid Hydrogels for 3D Cellular Engineering". ACS Nano. vol. 6, No. 4, pp. 2960-2968, 2012.
Loh et al. "New Biodegradable Thermogelling Copolymers Having Very Low Gelation Concentrations". Biomacromolecules. vol. 8, pp. 585-593, 2007.
Kim et al. "New Cucurbituril Homologues: Syntheses, Isolation, Characterization, and X-ray Crystal Structures of Cucurbit[n]uril (n=5, 7, and 8)". J. Am. Chem. Soc. vol. 122, pp. 540-541, 2000.

(56) References Cited

OTHER PUBLICATIONS

U.S. Appl. No. 14/233,417 in the name of Scherman et al., filed Jan. 17, 2014.
Jan. 3, 2012 Office Action issued in U.S. Appl. No. 12/734,925.
Jul. 2, 2012 Office Action issued in U.S. Appl. No. 12/734,925.
Sep. 25, 2015 Office Action issued in Chinese Patent Application No. 201380020985.8.
Dec. 21, 2015 Office Action issued in U.S. Appl. No. 14/233,417.
Nechifor et al., "The Size Distribution of Core Shell Polymeric Capsules as Revealed by Low-Field NMR Diffusometry," Applied Magnetic Resonance, vol. 40, pp. 205-211, Published Online Feb. 12, 2011.
Nov. 29, 2012 Search Report issued in International Patent Application No. PCT/GB2012/051787.
Nov. 29, 2012 Written Opinion issued in International Patent Application No. PCT/GB2012/051787.
Abraham et al. "Microfluidic Synthesis of Reversibly Swelling Porous Polymeric Microcapsules with Controlled Morphology". vol. 20, pp. 2177-2182, 2008.
Ameloot et al. "Interfacial synthesis of hollow metal-organic framework capsules demonstrating selective permeability". Nature Chemistry. DOI. 10.1038/NCHEM.1026, pp. 1-6, Apr. 10, 2011.
An et al. "pH Controlled Permeability of Lipid/Protein Biometric Microcapsules". Biomacromolecules. vol. 7, pp. 580-585, 2006.
Andrieux et al. "Characterization of Fluorescein Isothiocyanate-Dextrans Used in Vesicle Permeability Studies". Anal. Chem. vol. 74, No. 20, pp. 5217-5226, 2002.
Anema et al. "Shell-Isolated Nanoparticle-Enhanced Raman Spectroscopy: Expanding the Versatility of Surface-Enhanced Raman Scattering". Annu. Rev. Anal. Chem. vol. 4, pp. 129-150, 2011.
Bush et al. "Charge-Mediated Recognition of N-Terminal Tryptophan in Aqueous Solution by a Synthetic Host". J. Am. Chem. Soc. vol. 127, pp. 14511-14517, 2005.
Caruso et al. "Nanoengineering of Inorganic and Hybrid Hollow Spheres by Colloidal Templating". Science. vol. 282, pp. 1111-1114, Nov. 6, 1998.
Cavalieri et al. "Assembly and Functionalization of DNA-Polymer Microcapsules". ACS Nano. vol. 3, No. 1, pp. 234-240, 2009.
Chiefari et al. "Living Free-Radical Polymerization by Reversible Addition-Fragmentation Chain Transfer: The RAFT Process". Macromolecules. vol. 31, pp. 5559-5562, 1998.
Comiskey et al. "An electrophoretic ink for all-printed reflective electronic displays". Nature. vol. 394, pp. 253-255, Jul. 16, 1998.
Cui et al. "Monodisperse Polymer Capsules: Tailoring Size, Shell, Thickness, and Hydrophobic Cargo Loading via Emulsion Templating". Adv. Funct. Mater. vol. 20, pp. 1625-1631, 2010.
Danil de Namor et al. "Thermodynamics of Calixarene Chemistry". Chem. Rev. vol. 98, pp. 2495-2525, 1998.
De Cock et al. "Polymeric Multilayer Capsules in Drug Delivery". Angew. Chem. Int. Ed. vol. 49, pp. 6954-6973, 2010.
Donath et al. "Novel Hollow Polymer Shells by Colloid-Templated Assembly of Polyelectrolytes". Angew. Chem. Int. Ed. vol. 37, No. 16, pp. 2201-2205, 1998.
Dsouza et al. "Fluorescent Dyes and Their Supramolecular Host/Guest Complexes with Macrocycles in Aqueous Solution". Chem. Rev. vol. 111, pp. 7941-7980, 2011.
Duffy et al. "Rapid Prototyping of Microfluidic Systems in Poly(dimethylsiloxane)". Anal. Chem. vol. 70, pp. 4974-4984, 1998.
Forster et al. "Infrared, Ramen and Resonance Ramen Investigations of Methylviologen and its Radical Cation". Journal of Ramen Spectroscopy. vol. 12, No. 1, pp. 36-48, 1982.
Frens et al. "Controlled Nucleation for the Regulation of the Particle Size in Monodisperse Gold Suspensions". Nature Physical Science. vol. 241, pp. 20-22, Jan. 1, 1973.
Garstecki et al. "Formation of droplets and bubbles in a microfluidic T-junction-scaling and mechanism of break-up". Lab Chip. vol. 6, pp. 437-446, 2006.

Gokel et al. "Crown Ethers: Sensors for Ions and Molecular Scaffolds for Materials and Biological Models". Chem. Rev. vol. 104, pp. 2723-2750, 2004.
Granath, Kirsti. "Solution Properties of Branched Dextrans". Journal of Colloid Science. vol. 13, pp. 308-328, 1958.
Gunther et al. "Multiphase microfluidics: from flow characteristics to chemical and materials synthesis". Lab Chip. vol. 6, pp. 1487-1503, 2006.
Hermanson et al. "Permeability of silk microcapsules made by the interfacial adsorption of protein". Phys. Chem. Chem. Phys. vol. 9, pp. 6642-6446, 2007.
Holtze et al. "Biocompatible surfactants for water-in-fluorocarbon emulsions". Lab Chip. vol. 8, pp. 1632-1639, 2008. The Royal Soc. of Chem.
Huebner et al. "Microdroplets: A sea of applications?". Lab Chip. vol. 8, pp. 1244-1254, 2008. The Royal Soc. of Chem.
Jiao et al. "A systems Approach to Controlling Supramolecular Architecture and Emergent Solution Properties via Host-Guest Complexation in Water". J. Am. Chem. Soc. vol. 132, pp. 15734-15743, 2010.
Jiao et al. "Size Selective Supramolecular Cages from Aryl-Bisimidazolium Derivatives and Cucurbit[8]uril". Organic Letters. vol. 13, No. 12, pp. 3044-3047, 2011.
Kelly et al. "The Optical Properties of Metal Nanoparticles: The Influence of Size, Shape and Dielectric Environment". J. Phys. Chem. B. vol. 107, pp. 668-677, 2003.
Lagona et al. "The Cucurbit[n]uril Family". Angew. Chem. Int. Ed. vol. 44, pp. 4844-4870, 2005.
Link et al. "Size and Temperature Dependence of the Plasmon Absorption of Colloidal Gold Nanoparticles". J. Phys. Chem. B. vol. 103, pp. 4212-4217, 1999.
Martin et al. "Charged Gold Nanoparticles in the Non-Polar SOlvents: 10-min Synthesis and 2D Self-Assembly". Langmuir. vol. 26, No. 10, pp. 7410-7417, 2010.
Mehvar, Reza. "Dextrans for targeted and sustained delivery of therapeutic and imaging agents". Journal of Controlled Release. vol. 69, pp. 1-25, 2000.
Moghaddam et al. "New Ultrahigh Affinity Host-Guest Complexes of Curcurbit[7]uril with Bicycle[2.2.2]octane and Adamantane Guests: Thermodynamic Analysis and Evaluation of M2 Affinity Calculations". J. Am. Chem. Soc. vol. 133, pp. 3570-3581, 2011.
Patra et al. "Colloidal Microcapsules: Self-Assembly of Nanoparticles at the Liquid-Liquid Interface". Chem. Asian J. DOI: 10.1002/asia. 201000301, pp. 1-13, 2010.
Peyratout et al. "Tailor-Made Polyelectrolyte Microcapsules: From Multilayers to Smart Containers". Angew. Chem. Int. Ed. vol. 43, pp. 3762-3783, 2004.
Priest et al. "Microfluidic polymer multilayer adsorption on liquid crystal droplets for microcapsule synthesis". Lab Chip. vol. 8, pp. 2182-2187, 2008. The Royal Soc. of Chem.
Rauwald et al. "Correlating Solution Binding and ESI-MS Stabilities by Incorporating Solvation Effects in a Confined Cucurbit[8]uril System". J. Phys. Chem. B. vol. 114, pp. 8606-8615, 2010.
Rekharsky et al. "Complexation Thermodynamics of Cyclodextrins". Chem. Rev. vol. 98, pp. 1875-1917, 1998.
Therberge et al. "Microdroplets in Microfluidics: An Evolving Platform for Discoveries in Chemistry and Biology". Angew. Chem. Int. Ed. vol. 49, pp. 5846-5868, 2010.
Thorsen et al. "Dynamic Pattern Formation in a Vesicle-Generating Microfluidic Device". Physical Review Letters. vol. 86, No. 18, pp. 4163-4166, Apr. 30, 2001.
Utada et al. "Monodisperse Double Emulsions Generated from a Microcapillary Device". Science. vol. 308, pp. 537-541, Apr. 22, 2005.
Xu et al. "Preparation of Highly Monodisperse Droplet in a T-Junction Microfluidic Device". AIChE Journal. vol. 52, No. 9, pp. 3005-3010, 2006.
Yang et al. "Microfluidic assisted synthesis of multi-functional polycaprolactone microcapsules: incorporation of CdTe quantum dots, Fe3O4 superparamagnetic nanoparticles and tamoxifen anticancer drugs". Lab Chip. vol. 9, pp. 961-965, 2009.

(56) References Cited

OTHER PUBLICATIONS

Appel et al. "Ultrahigh-Water-Content Supramolecular Hydrogels Exhibiting Multistimuli Responsiveness". J. Am. Chem. Soc. vol. 134, pp. 11767-11773, 2012.
Appel et al. "Supramolecular polymeric hydrogels". Chem. Soc. Rev. vol. 41, pp. 6195-6214, 2012.
Benguigui et al. "Homogeneous and inhomogeneous polyacrylamide gels as observed by small angle neutron scattering: A connection with elastic properties". Eur. Phys. J. B. vol. 11, pp. 439-444, 1999.
Biedermann et al. "Postpolymerization Modification of Hydroxyl-Functionalized Polymers with Isocyanates". Macromolecules. vol. 44, pp. 4828-4835, 2011.
Lim et al. "Self-Assembled Ternary Complex of Cationic Dendrimer, Cucurbituril, and DNA: Noncovalent Strategy in Developing a Gene Delivery Carrier". Bioconjugate Chem. vol. 13, pp. 1181-1185, 2002.
Glossary, Drug-Discovery-and-Development, 2012, http:www.dddmag.com/content/glossary-drug-discovery-and-development-terms.
Bosman et al.; "Supramolecular polymers at work;" Materials Today; Apr. 2004; pp. 34-39; vol. 7; Elsevier Ltd.
Sijbesma et al.; "Reversible Polymers Formed from Self-Complementary Monomers Using Quadruple Hydrogen Bonding;" Science; Nov. 28, 1997; pp. 1601-1604; vol. 278; American Association for the Advancement of Science Washington D.C.
Archer et al.; "Coordination chemistry from monomers to copolymers;" Coordination Chemistry Reviews; 1993; pp. 49-68; vol. 128; Elsevier Sequoia.
Swiegers et al.; "New Self-Assembled Structural Motifs in Coordination Chemistry;" Chem. Rev.; 2000; pp. 3483-3537; vol. 100; American Chemical Society.
Lehn et al.; "Spontaneous assembly of double-stranded helicates from oligobipyridine ligands and copper(I) cations: Structure of an inorganic double helix;" Proc. Natl. Acad. Sci.; May 1987; pp. 2565-2569; vol. 84.
Schutte et al.; "Metallosupramolecular Thin Polyelectrolyte Films;" Angew. Chem. Int. Ed.; 1998; pp. 2891-2893; vol. 37, No. 20; Wiley-VCH Verlag GmbH & Co.
Lohmeijer et al.; "Supramolecular Engineering with Macromolecules: An Alternative Concept for Block Copolymers;" Angew. Chem. Int. Ed.; 2002; pp. 3825-3829; vol. 41, No. 20; Wiley-VCH Verlag GmbH & Co.
Chen et al; "Ruthenuim Bipyridine-Containing Polymers and Block Copolymers via Ring-Opening Metathesis Polymerization;" Macromolecules; 2004; pp. 5866-5872; vol. 37; American Chemical Society.
Zhou et al,; "Synthesis and Characterization of Bis(2,2':6'2"-terpyridine)ruthenium(II)-Connected Diblock Polymers via RAFT Polymerization;" Macromolecules; 2005; pp. 4114-4123; vol. 38; American Chemical Society.
Fustin et al.; "Metallo-Supramolecular Block Copolymers:" Advanced Materials; 2007; pp. 1665-1673; vol. 19; Wiley-VCH Verlag GmbH & Co.
Scherman et al.; "Olefin metathesis and quadruple hydrogen bonding: A powerful combination in multistep supramolecular synthesis;" PNAS; Aug. 8, 2006; pp. 11850-11855; vol. 103, No. 32; The National Academy of Sciences of the USA.
Yang et al.; "Supramolecular AB Diblock Copolymers;" Angew. Chem. Int. Ed.; 2004; pp. 6471-6474; vol. 43; Wiley-VCH Verlag GmbH & Co.
Higley et al.; "A Modular Approach toward Block Copolymers;" Chem. Eur. J.; 2005; pp. 2946-2953; vol. 11; Wiley-VCH Verlag GmbH & Co.
Yamauchi et al.; "Combinations of Microphase Separation and Terminal Multiple Hydrogen Bonding in Novel Macromolecules;" J. Am. Chem. Soc.; 2002; pp. 8599-8604; vol. 124; American Chemical Society.

Binder et al.; "Supramolecular Poly(ether ketone)-Polyisobutylene Pseudo-Block Copolymers;" Journal of Polymer Science: Part A: Polymer Chemistry; 2004; pp. 162-172; vol. 42; Wiley Periodicals, Inc.
Sontjens et al.; Stability and Lifetime of Quadruply Hydrogen Bonded 2-Ureido-4[1H]-pyrimidinone Dimers; J. Am. Chem. Soc.; 2000; pp. 7487-7493; vol. 122; American Chemical Society.
Shimizu; "Mini Review-Perspectives on main-chain hydrogen bonded supramolecular polymers;" Polymer International; 2007; pp. 444-452; vol. 56; Society of Chemical Industry.
Behrend et al.; "Justus Liebig's Annalen Der Chemie.;" 1904; pp. 1-37; vol. 339.
Freeman et al.; "Cucurbituril;" J. Am. Chem, Soc.; 1981; pp. 7367-7368; vol. 103; American Chemical Society.
Kim et al.; "Selective Inclusion of a Hetero-Guest Pair in a Molecular Host: Formation of Stable Charge-Transfer Complexes in Cucurbit[8]uril;" Angew. Chem. Int. Ed.; 2001; pp. 1526-1529; vol. 40, No. 8; Wiley-VCH Verlag GmbH.
Sindelar et al.; "Supramolecular Assembly of 2,7-Dimethyldiazapyrenium and Cucurbit[8]uril: A New Fluorescent Host for Detection of Catechol and Dopamine;" Chem. Eur. J.; 2005; pp. 7054-7059; vol. 11; Wiley-VCH Verlag GmbH & Co.
Jeon et al.; "Supramolecular Amphiphiles: Spontaneous Formation of Vesicles Triggered by Formation of a Charge-Transfer Complex in a Host;" Angew. Chem. Int. Ed.; 2002; pp. 4474-4476; vol. 41, No. 23; Wiley-VCH Verlag GmbH & Co.
Jeon et al.; "Molecular Loop Lock: A Redox-Driven Molecular Machine Based on a Host-Stablized Charge-Transfer Complex;" Angew. Chem. Int. Ed.; 2005; pp. 87-91; vol. 44; Wiley-VCH Verlag GmbH & Co.
Ko et al.; "Designed Self-Assembly of Molecular Necklaces Using Host-Stabilized Charge-Transfer Interactions;" J. Am. Chem. Soc.; 2004; pp. 1932-1933; vol. 126; American Chemical Society.
Kim et al.; "Growth of poly(pseudorotaxane) on gold using host-stabilized charge-transfer interaction;" Chem. Commun.; 2004; pp. 848-849; The Royal Society of Chemistry.
Jeon et al.; "A [2] Pseudorotaxane-Based Molecular Machine: Reversible Formation of a Molecular Loop Driven by Electrochemical and Photochemical Stimuli;" Angew. Chem, In, Ed.; 2003; pp. 4097-4100; vol. 42; Wiley-VCH Verlag GmbH & Co. cited byapplicant.
Ko et al.; "Supramolecular assemblies built with host-stabilized charge-transfer interactions;" Chem. Commun.; 2007 pp. 1305-1315; The Royal Society of Chemistry.
Moon et al.; "Cucurbit[8]uril-Mediated Redox-Controlled Self-Assembly of Viologen-Containing Dendrimers;" Angew. Chem. Int. Ed.; 2004; pp. 5496-5499; vol. 43; Wiley-VCH Verlag GmbH & Co.
Wang et al.; "Electrochemical Switching and Size Selection in Cucurbit[8]uril-Mediated Dendrimer Self-Assembly;" Angew. Chem. Int. Ed.; 2006; pp. 7042-7046; vol. 45; Wiley-VCH Verlag GmbH & Co.
Floudas et al.; "Poly(ethylene oxide-b-isoprene) Diblock Copolymer Phase Diagram;" Macromolecules; 2001; pp. 2947-2957; vol. 34; American Chemical Society.
Sun et al.; "The photoinduced long-lived charge-separated state of Ru(bpy).sub.3-methylviologen with cucurbit[8]uril in aqueous solution;" Chem. Commun; 2006; pp. 4195-4197; The Royal Society of Chemistry.
Jon et al.; "A facile, stereoselective [2+2] photoreaction mediated by cucurbit[8]uril;" Chem. Commun.; 2001; pp. 1938-1939; The Royal Society of Chemistry.
Rauwald et al.; "Supramolecular Block Copolymers with Cucurbit[8]uril in Water;" Angew. Chem. Int. Ed.; 2008; pp. 3950-3953; vol. 47; Wiley-VCH Verlag GmbH & Co.
Broeren et al.; "Multivalency in the Gas Phase: The Study of Dendritic Aggregates by Mass Spectrometry;" Angew. Chem. Int. Ed.; 2004; pp. 3557-3562; vol. 43; Wiley-VCH Verlag GmbH & Co.
Osaka et al.; "Characterization of host-guest complexes of cucurbit[n]uril (n=6,7) by electrospray ionization mass spectrometry;" J. Mass Spectrom; 2006; pp. 202-207; vol. 41; John Wiley & Sons, Ltd.
Brunsveld et al.; "Supramolecular Polymers;" Chem. Rev.; 2001; pp. 4071-4097; vol. 101; American Chemical Society.

(56) References Cited

OTHER PUBLICATIONS

Knapp et al.; "A Novel Synthetic Strategy toward Soluble, Well-Defined Ruthenium(II) Coordination Polymers," Macromolecules; 1996; pp. 478-480; vol. 29; American Chemical Society.
Kim et al.; "Direct Synthesis of Polymer Nanocapsules with a Noncovalently Tailorable Surface.," Angew. Chem. Int. Ed.; 2007; vol. 46, pp. 3471-3474; Wiley-VCH Verlag GmbH & Co.
Ligthart et al.; "Supramolecular Polymer Engineering;" Macromolecular Engineering, Precise Synthesis, Materials Properties, Applications; 2007; pp. 351-399; Wiley-VCH Verlag GmbH & Co.
Nov. 3, 2009 International Search Report issued in International Application No. PCT/GB2008/004016.
Nov. 3, 2009 Written Opinion of the International Search Report issued in International Application No. PCT/GB2008/004016.
Appel et al. "Supramolecular Cross-Linked Networks via Host-Guest Complexation with Cucurbit[8]uril". J. Am. Chem. Soc. vol. 132, pp. 14251-14260, 2010.
Patra et al. "Formation and Size Tuning of Colloidal Microcapsules via Host-Guest Molecular Recognition at the Liquid-Liquid Interface". Langmuir. vol. 25, No. 24, pp. 13852-13854, 2009.
Wang et al. "Stepwise Assembly of the Same Polyelectrolytes Using Host-Guest Interation to Obtain Microcapsules with Multiresponsive Properties". Chem. Mater. vol. 20, pp. 4194-4199, 2008.
Hwang et al., "Noncovalent Immobilization of Proteins on a Solid Surface by Cucurbit[7]uril-Ferrocenemethylammonium Pair, a Potential Replacement of Biotin-Avidin Pair". J. Am. Chem Soc. vol. 129, pp. 4170-4171, 2007.
Taylor et al. "Precise Subnanometer Plasmonic Junctions for SERS within Gold Nanoparticle Assemblies Using Cucurbit[n]uril 'Glue'". ACS Nano. vol. 5, No. 5, pp. 3878-3887, 2011.
Nov. 7, 2011 Search Report issued in British Patent Application No. 1112893.1.
Mar. 14, 2012 Search Report issued in British Patent Application No. 1202127.5.
Kola et al., "A detailed description of synthetic and natural polymers which are used in the formulation of sustained release drug delivery system: a review," Journal of Chemical and Pharmaceutical Sciences, vol. 6(3), pp. 161-169, Jul.-Sep. 2013 Issue.
Aug. 18, 2015 Office Action issued in U.S. Appl. No. 14/233,417.
Sep. 25, 2015 Office Action issued in Chinese Application No. 2013800209858.
May 16, 2016 Office Action issued in Chinese Application No. 2013800209858.
Nov. 22, 2016 Office Action issued in European Application No. 13706691.6.
Appel, Eric A., et al. "Supramolecular Crosslinked Networks via Host-Guest Complexation with Cucurbit[8]uril," Journal of the American Chemical Society, vol. 132, No. 40, Sep. 2010, pp. 14251-14260.
De Greet, Tom F. A., et al. "Supramolecular Polymerization." Chemical Reviews. vol. 109, No. 11, Sep. 2009, pp. 5687-5754.
Liu, Yiliu, et al. "Host-Enhanced pi-pi Interaction for Water-Soluble Supramolecular Polymerization." Chemistry Europe Journal. vol. 17, Aug. 2011, pp. 9930-9935.
Richard, D., et al., "Analysis and visualisation of neutron-scattering data." Journal of Neutron Research. vol. 4, 1996. pp. 33-39.

\* cited by examiner

- HEC-Np (1.5 %) + PVA@CB[8] (0.3 %)
- HEC-Np (1.0 %) + PVA@CB[8] (0.2 %)
- HEC-Np (0.5 %) + PVA@CB[8] (0.1 %)
- HEC-Np (0.5 %) + PVA@CB[8] (0.05 %)
- HEC-Np (0.25 %) + PVA@CB[8] (0.05 %)

CUCURBITURIL-BASED HYDROGELS

RELATED APPLICATIONS

This case is related to and claims priority from GB 1202834.6 filed on 20 Feb. 2012 and GB 1301648.0 filed on 30 Jan. 2013, the contents both of which are hereby incorporated by reference in their entirety.

FIELD OF THE INVENTION

This invention relates to hydrogels based on a cucurbituril cross-linked supramolecular network, and methods for the preparation of such hydrogels, and their use in methods of delivering components held within the hydrogel.

BACKGROUND

Hydrogels are three-dimensional cross-linked polymer networks that entrap and store large amounts of water. Given their similarity to soft biological tissues and variable mechanical properties, i.e. from soft and weak to hard and tough, they are increasingly important in a variety of biomedical and industrial applications.

Hydrogels can be prepared using either a covalent or a noncovalent approach. Most covalently cross-linked polymer hydrogels are brittle, have poor transparency and lack the ability to self-heal once the network is broken (Peppas et al. *Annu. Rev. Biomed. Eng.* 2 2000, 9-29). These shortcomings have been addressed by employing dynamic and reversible non-covalent interactions as the structural cross-links in hydrogels (direct formation) or driving nanofiber formation, whose entanglement subsequently leads to hydrogel formation (indirect formation) (Estroff et al. *Chem. Rev.* 2004, 104, 1201-1217; Wojtecki et al. *Nat. Mat.* 2010, 10, 14-27). A myriad of small molecules exist which self-assemble into long fibers, leading to hydrogel formation. An excellent example of which is the series of amphiphilic peptides developed by Stupp and co-workers (Hartgerink et al. *Science* 2001, 294, 1684-1688). Relatively strong hydrogels ($G'$=1 kPa) with low loadings of material relative to water (0.5 wt % peptide+0.5 wt % $CaCl_2$) can be prepared in this manner (Greenfield et al. *Langmuir* 2010, 26, 3641-3647). There are, however, far fewer examples of direct hydrogel formation, especially those with high water content (>97%).

Drawing from the broad precedence of supramolecular polymers it is clear only very few non-covalent systems exist which function in aqueous medium (Sijbesma et al. *Science* 1997, 278, 1601-1604; Greef et al. *Chem. Rev.* 2009, 109, 5687-5754). These include host-guest interactions of cyclodextrins and cucurbit[n]urils, hydrophobic, ionic, and some metal-ligand interactions. Several attempts have been made previously to develop hydrogels from cyclodextrins, however, they have been intrinsically limited by the low binding affinity of CDs to their guests, which has resulted in poor mechanical properties (Kretschmann et al. *Angew. Chem. Int. Edit.* 2006, 45, 4361-4365; Wu et al. Langmuir 2008, 24, 10306-10312; Koopmans et al. *Macromolecules* 2008, 41, 7418-7422). Moreover, ionic interactions are extremely sensitive to ionic strength of the aqueous media and often to changes in pH while the use of transition metals in metal-ligand pairs must be avoided in many applications due to toxicity and environmental concerns (Van Tomme et al. *Biomaterials* 2005, 26, 2129-2135; Hunt, J. et al. *Adv. Mater.* 2011, 23, 2327-2331; Wang et al. *Nature* 2010, 463, 339-343). Thermally activated hydrogels formed by hydrophobic association of block copolymers, typically containing two or more blocks displaying a lower critical solution temperature (LCST), e.g. N-isopropylacrylamide or Pluronics, have been extensively studied (Loh et al. Macromol. Symp. 2010, 296, 161-169; Loh et al. *Biomacromolecules* 2007, 8, 585-593). Although these materials have demonstrated potential for biomedical applications such as tissue engineering on account of their spontaneous formation at physiological temperature and biocompatibility, their applicability in other industries has not been demonstrated.

Biomaterials represent a rapidly developing field of designer materials which typically exhibit properties similar to biological matter or are biocompatible and useful for important biological applications such as drug delivery and tissue engineering. Hydrogels are one type of biomaterial which have shown themselves to be particularly important candidates for drug delivery and tissue engineering applications given their similarity to soft biological tissue and highly variable mechanical properties (Lutolf et al. *Nat. Mat.* 2009, 8, 451-453; Staats et al. *Nat. Mat.* 2010, 9, 537-538; Nochi et al. *Nat. Mat.* 2010, 9, 572-578). Many systems exist which have been thoroughly studied for their sustained drug release for drug delivery, wound covering and chemosensitizing for cancer therapy (Loh et al. *J. Control. Release* 2010, 143, 175-182; Loh et al. *J. Phys. Chem. B* 2009, 113, 11822-11830; Loh et al. *Biomaterials* 2008, 29, 2164-2172; Loh et al. *Biomaterials* 2008, 29, 3185-194; Loh et al. *Biomaterials* 2007, 28, 4113-4123; Li et al. *Biomacromolecules* 2005, 6, 2740-2747).

A high concentration of the polymeric constituents is often needed in these formulations, sometimes requiring greater than 15 wt %, and many times such formulations exhibit poor resilience and strong burst release of drugs. These shortcomings have made the system unsuitable for many biomedical applications (Esposito et al. *Int. J. Pharm.* 1996, 142, 923; Katakam et al. *Int. J. Pharm.* 1997, 152, 53-58). Recently, biocompatible thermogelling polymers based from poly(PEG/PPG/PHB urethane)s requiring relatively low polymer concentrations (5 wt %) to form hydrogels from aqueous solutions upon heating have been described (Loh et al. *Biomacromolecules* 2007, 8, 585-593). Moreover, the hydrolytic degradability of these triblock copolymers allowed for further tunability of their protein release, which was shown to extend up to approximately 75 days in vitro (Loh et al. *Biomaterials* 2007, 28, 4113-4123).

Some of the present inventors have previously described a hydrogel based on a network of polymers linked together by CB[8] (Appel et al. *J. Am. Chem. Soc.* 2010, 132, 14251-14260). Such a hydrogel is purported to facilitate progress in the fields of smart, self-healing materials, self-assembled hydrogels, and controlled solution viscosity. The polymers for use in the hydrogel have molecular weights in the range 10.1 to 37.1 kDa and polydispersity values in the range 1.11 to 2.42. At least one of the polymers has a molecular weight in the range 10.1 to 21.8 kDa, and at least one of the polymers has a polydispersity value in the range 1.53 to 2.42. The functionality of the polymers is in the range 4.3 to 10.1%. The hydrogel is based on the non-covalent attachment of a polystyrene-based polymer to a polyacrylamide-based polymer via a cucurbituril handcuff.

Whilst some of the present inventors have referred to the network described in the work above as a hydrogel, this is simply a convenient term to refer to the material that was obtained. It is acknowledged that the material may be referred to as a viscoelastic material. The rheological properties of this material are not ideal. For example, when the rheological properties of the materials were analysed by dynamic oscillatory rheology at 10% strain, the loss modulus (G") is observed to dominate the storage modulus (G') at higher frequencies. Thus, the loss modulus is dominant at frequencies of 20 rad/s or more. At lower frequencies the storage module is dominant. G' and G" are therefore not linear and are not parallel in the oscillatory rheology.

The earlier work also describes the Newtonian behaviour of the material to a high shear (as measured at steady shear measurements) with a subsequent catastrophic loss of viscosity. For example, the materials have a viscosity in the range 8 to 50 Pa s at shear rates in the range 0.1 to 30 1/s. The viscosity remains substantially constant through this range of shear rates. At shear rates above 30 1/s, the viscosity drops dramatically.

SUMMARY OF THE INVENTION

The present invention generally provides a hydrogel suitable for holding a deliverable component. The present inventors have found that hydrogels based on a network of cucurbituril complexes are suitable for holding and delivering components. In particular, the present inventors have found that hydrogels obtainable from the complexation of cucurbituril with a high molecular weight polymer suitably functionalised with cucurbituril guest functionality may be used to hold and deliver components such as proteins. Advantageously, the network, obtainable from the cucurbituril and the polymer component/s, is only a small weight percentage of the overall hydrogel. Thus, the hydrogels of the present invention have a very high water content.

The rheological proprieties of the hydrogels are useful and desirable. These properties may be advantageously tuned through appropriate changes to the hydrogel components and their ratios. A stable hydrogel may be prepared from relatively little material. As described herein the hydrogels have a dominant storage modulus (G') over loss modulus (G") for any frequency value in the range 0.1 to 100 rad/s for a hydrogel analysed by frequency sweep measurement at 37° C. The present hydrogels may be regarded as true hydrogels in view of the fact that G' and G" are substantially linear and substantially parallel in the oscillatory rheology, with G' dominant throughout. This is in contrast to previously reported materials where G' is not dominant throughout the oscillatory rheology.

The shear behaviour of the hydrogels of the invention is a further distinguishing feature. The hydrogels described herein display continuous shear-thinning behaviour when analysed by steady shear methods. At low shear rates, for example in the range 0.1 to 0.3 1/s, the viscosity value for the hydrogel material of the invention may be 100 Pa s or more, for example 400 Pa s or more, for example 700 Pa s or more. In contrast, at the same shear rates, the prior art materials have significantly lower viscosity values (for example, in the range 8 to 50 Pa s).

The present inventors believe that the use of higher molecular weight polymers, such as higher molecular weight hydrophilic polymers, provides hydrogels having these advantageous rheological properties. The present inventors also recognise that hydrogels based on a cucurbituril cross-linked supramolecular network are suitable for holding and releasing components, as necessary.

In one aspect of the invention there is provided a hydrogel holding a component, wherein the hydrogel has a supramolecular cross-linked network obtainable or obtained from the complexation of an aqueous composition comprising cucurbituril and one or more polymers having suitable cucurbituril guest functionality.

In one embodiment, the aqueous composition comprises a polymer having a molecular weight of 50 kDa or more, for example 200 kDa or more. In one embodiment, the component has a molecular weight of 200 kDa or more.

In a second aspect, the present invention provides a hydrogel, wherein the hydrogel has a supramolecular cross-linked network obtainable or obtained from the complexation of an aqueous composition comprising cucurbituril and one or more polymers having suitable cucurbituril guest functionality. One or more polymers in the aqueous composition has a molecular weight of 50 kDa or more. The polymers in the composition may be hydrophilic polymers.

In another aspect of the invention there is provided a method for the preparation of a hydrogel holding a component, the method according to (a) or (b), wherein
  (a) the method comprises the steps of (i) obtaining or forming a hydrogel, and (ii) introducing a component into the hydrogel thereby to form a hydrogel holding a component, wherein the hydrogel holding a component is formed by bringing into contact in an aqueous solution a mixture of cucurbituril, and one or more polymers having suitable cucurbituril guest functionality, thereby to form a supramolecular cross-linked network; and
  (b) the method comprises the step of bringing into contact in an aqueous solution a mixture of cucurbituril, a component, and one or more polymers having suitable cucurbituril guest functionality, thereby to form a hydrogel holding a component and the hydrogel is a supramolecular cross-linked network.

In another aspect of the invention there is provided a method for the preparation of a hydrogel, the method comprising the step of bringing into contact in an aqueous solution a mixture of cucurbituril, and one or more polymers having suitable cucurbituril guest functionality, thereby to form a supramolecular cross-linked network, wherein the aqueous composition comprises a polymer having a molecular weight of 50 kDa or more.

Advantageously, the hydrogels of the present invention are obtained seconds after the cucurbituril and the one or more polymers having suitable cucurbituril guest functionality, optionally together with a component, are brought into contact. The methods of the invention may be performed under mild and ambient conditions.

In a further aspect of the invention there is provided a method of delivering a component to a location, the method comprising the steps of:
  (i) providing a hydrogel holding a component, according to the first aspect of the invention;
  (ii) making the hydrogel available at a target location;
  (iii) releasing the component from the hydrogel.

In additional aspects of the invention there is provided the use of the hydrogels of the first or the second aspects, for example in medicine.

In any of the aspects described above, cucurbituril may be replaced with an alternative host, for example a host is capable of forming a ternary host-guest complex.

In one embodiment, the host is selected from cucurbituril, cyclodextrin, calix[n]arene, and crown ether compounds.

In one embodiment, the host is selected from cyclodextrin, calix[n]arene, and crown ether compounds.

In one embodiment, the host is capable of forming a ternary host-guest complex.

In a further aspect of the invention there is provided a hydrogel that is obtained or obtainable from a hydrogel of the first aspect of the invention by forming a covalent link or crosslink between polymers in the hydrogel, for example between guest molecules of the polymers.

In an embodiment of the invention there is provided a hydrogel as described herein, such as a hydrogel of the first aspect of the invention, where the polymers are non-covalently linked or cross-linked via a complex and are additionally covalently linked or cross-linked.

In one aspect there is provided a method of covalently linking or cross-linking a polymer, the method comprising the steps of:
(i) providing a non-covalently linked polymer or polymers, wherein the non-covalent linked is formed from a ternary complex of a host holding first and second guest molecules provided on the polymer or polymers;
(ii) permitting the polymer or polymers to react, thereby to form a covalent bond linking the polymer or polymers.

In a further aspect, there is provided a method of preparing a hydrogel having a supramolecular cross-linked network, wherein the hydrogel is formed from the covalent crosslinking of a polymer and/or the covalent linking of a polymer to another polymer, the method comprising the steps of:
(i) providing a hydrogel having a supramolecular cross-linked network which is obtainable from the ternary complexation of an aqueous composition comprising a host, such as cucurbituril, and one or more polymers having suitable guest functionality, such as cucurbituril guest functionality;
(ii) permitting the polymer or polymers to react, thereby to form a covalent bond linking the polymer or the polymers.

SUMMARY OF THE FIGURES

FIG. 3 (c) shows the small angle neutron scattering of the same two hydrogels in $D_2O$.

DETAILED DESCRIPTION OF THE INVENTION

Figure 1:
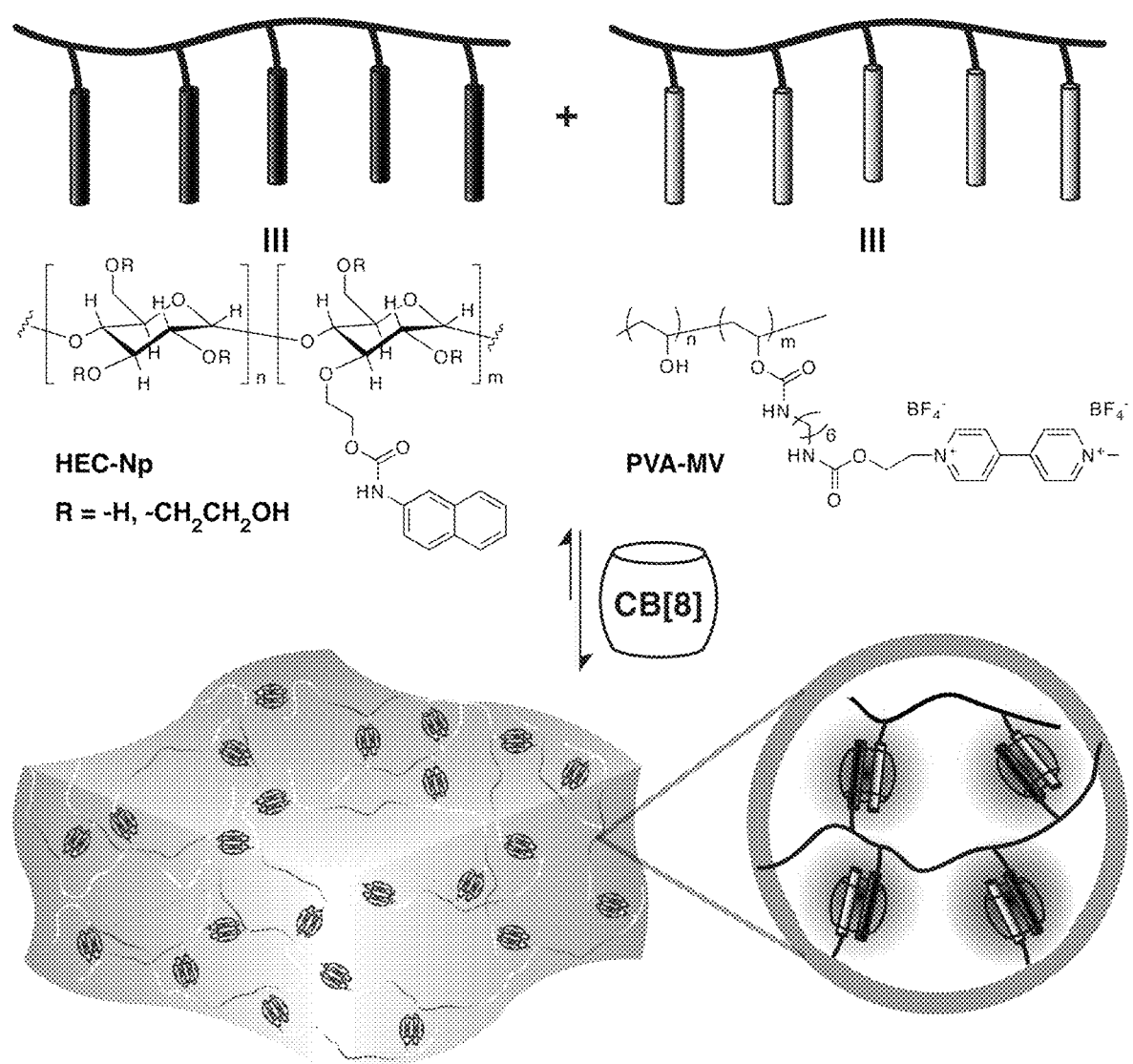
FIG. 1 is a schematic representation of the supramolecular hydrogel prepared through addition of CB[8] to a mixture of a multivalent first and second guest functional polymers in water.

The present inventors have established that structurally useful hydrogels may be readily prepared from relatively minor amounts of cucurbituril and one or more polymers suitably functionalised with cucurbituril guest functionality. The hydrogels may therefore have a very high water content. The inventors have also established that structurally useful hydrogels may be readily prepared from cucurbituril and one or more high molecular weight polymers suitably functionalised with cucurbituril guest functionality.

The supramolecular nature of these hydrogels provides scope for tuning the mechanical properties and the hydrogel is usefully responsive to various external stimuli including temperature, electric potential and competing guests. The hydrogels are easily processed and the simplicity of their preparation and the high tunability of their properties are distinguishing for many important water-based applications. Moreover, in many embodiments, the components of the hydrogel network (the polymer and the cucurbituril) are available from inexpensive and renewable resources.

Many of the hydrogels described herein have an exceptionally low total polymer concentration. The high water content of the hydrogel makes it highly attractive for biomedical applications, for example due to improved biocompatibility. The inventors have established that certain polymers for use in the hydrogel, which polymers are suitably functionalised with cucurbituril guest functionality, have low toxicity, for example as measured against a fibroblast cell line. The present inventors have also shown that the integrity of the hydrogels is not substantially altered on heating to 75° C.

In addition, rigid polymer chains with pendant phenylalanine or tryptophan amino acids have the ability to form hydrogels when in the presence of CB[8]. It has been determined that the phenylalanine unit affords much stronger hydrogel materials than its tryptophan counterpart. The worked described herein demonstrates the potential for improved biomedical systems for drug delivery as gel formation can now be achieved using biologically relevant, such as biologically compatible, guest moieties for the CB[8] based crosslinking. This bypasses limitations of potentially toxic polymer and guest metabolites. Where such guests are attached to biocompatible, such as natural, polymers it is clear that the system may be suitable for use in 3D cell culture, drug delivery and regenerative medicine. In these systems, the material properties of the hydrogel may be altered by appropriate changes in the host concentration (or equivalency) and/or the nature of the guests pendant to the polymer.

Some of the present inventors have previously described a hydrogel based on a network of polymers linked together by CB[8] (see Appel et al. *J. Am. Chem. Soc.* 2010, 132, 14251-14260). Typically, the hydrogels described herein are based on polymers having low functionality, high molecular weight and low polydispersity values. In contrast at least one of the polymers described in the inventors' previous work has high functionality, low molecular weight and/or a high polydispersity value. As discussed in the background section above, the materials described in previous work do not display dominant G' values across the entire oscillatory range. Additionally, the materials do not have high viscosity values at low shear rates.

Comparative examples provided herein also show that hydrogels prepared from a low molecular weight ($M_n$=ca. 10 kDa) and high polydispersity (PDI ca 2.2) polymer have a loss modulus (G") that dominates the storage modulus (G') at higher frequencies.

Hydrogel

The hydrogel of the invention is a three-dimensional cross-linked polymer network that holds water, optionally together with a component. In the present case, the network is obtainable or obtained from the complexation of cucurbituril hosts with suitable guest molecule functionality provided on one or more polymers. Thus, the hydrogel comprises this network and entrapped water.

In one aspect of the invention there is provided a hydrogel having a supramolecular cross-linked network obtainable or obtained from the complexation of an aqueous composition comprising cucurbituril and one or more polymers having suitable cucurbituril guest functionality. The aqueous composition comprises a polymer having a molecular weight of 50 kDa or more. The hydrogel of this aspect of the invention may find use in the first aspect of the invention, for holding a component.

In one embodiment, a network is obtainable from the complexation of (a) an aqueous composition comprising cucurbituril and (1) or (2); or (b) a composition comprising a plurality of covalently linked cucurbiturils and (1), (2) or (3).

In one embodiment, the network is obtainable from the complexation of (a) an aqueous composition comprising cucurbituril and (1) or (2); or (b) an aqueous composition comprising a plurality of covalently linked cucurbiturils and (1), (2) or (3).

In one embodiment, the network is obtainable from the complexation of an aqueous composition comprising cucurbituril and (1) or (2).

In one embodiment, the network is obtainable from the complexation of an aqueous composition comprising cucurbituril and (2).

In one embodiment, the network is obtainable from the complexation of an aqueous composition comprising cucurbituril and (1).

In one embodiment, a composition as described above further comprises a component, which component is held in the resulting hydrogel.

(1) comprises a first polymer covalently linked to a plurality of first cucurbituril guest molecules and a second polymer covalently linked to a plurality of second cucurbituril guest molecules, wherein a first guest molecule and a second guest molecule together with cucurbituril are suitable for forming a ternary guest-host complex. The first and second guest molecules may be the same or different.

(2) comprises a first polymer covalently linked to a plurality of first cucurbituril guest molecules and a plurality of second cucurbituril guest molecules, wherein a first and a second guest molecule together with cucurbituril are suitable for forming a ternary guest-host complex. The first and second guest molecules may be the same or different. Optionally the composition further comprises a second polymer covalently linked to one or more third cucurbituril guest molecules, one or more fourth cucurbituril guest molecules or both, wherein a third and a fourth molecule together with cucurbituril are suitable for forming a ternary guest-host complex, and/or the first and fourth molecules together with cucurbituril are suitable for forming a ternary guest-host complex, and/or the second and third molecules together with cucurbituril are suitable for forming a ternary guest-host complex.

(3) comprises a first polymer covalently linked to a plurality of first cucurbituril guest molecules, wherein the first guest molecule together with the cucurbituril are suitable for forming a binary guest-host complex. Optionally the composition further comprises a second polymer covalently linked to one or more second cucurbituril guest molecules, wherein the second guest molecule together with the cucurbituril are suitable for forming a binary guest-host complex.

In one embodiment, the water content of the hydrogel is at least 90 wt %, at least 95 wt %, at least 97 wt %, at least 98 wt %, at least 99 wt %, at least 99.5 wt %.

Where the water content is at such amounts, the present inventors have found that the hydrogels may be diluted, for example with a volume of water equivalent to the volume of the hydrogel, with only a slight reduction in mechanical properties.

In one embodiment, the total amount of polymer present in the hydrogel is at most 20 wt %, at most 10 wt %, at most 7.0 wt %, at most 5.0 wt %, at most 2.5 wt %, at most 2.0 wt %, at most 1.5 wt %, at most 1.0 wt %, at most 0.5 wt % or at most 0.4 wt %.

In one embodiment, the total amount of polymer present in the hydrogel is at least 0.05 wt %, at least 0.1 wt %, at least 0.2 wt %, at least 0.3 wt %.

In one embodiment, the total amount of polymer present in the hydrogel is in a range where the minimum and maximum amounts are selected from the embodiments above. For example, the total amount of polymer present is in the range 0.3 to 2.0 wt %.

In one alternative embodiment, a polymer present in the hydrogel is present in the amounts or ranges indicated above.

Where only one polymer is present in the hydrogel, the total amount of polymer present in the hydrogel refers to the amount of that polymer. Where two or more polymers are present in the hydrogel, the total amount is the sum of the amounts of each of the two or more polymers present.

In some embodiments, the hydrogel comprises a first polymer and a second polymer, such as a composition comprising cucurbituril and (1) as discussed above.

The two polymer system provides scope for making relatively easy changes to the hydrogel structure by varying the ratio of the polymers to one another and/or to the cucurbituril.

In one embodiment, the weight amount of the first polymer in the hydrogel is substantially the same as the weight amount of the second polymer in the hydrogel.

In one embodiment, the weight amount of the second polymer in the hydrogel is at least 2 times, at least 3 times, at least 4 times, at least 5 times, at least 10 times or at least 20 times the weight amount of the first polymer in the hydrogel.

In one embodiment, the mole amount of the second polymer in the hydrogel is substantially the same as the mole amount of the first polymer in the hydrogel.

In one embodiment, the mole amount of the second polymer in the hydrogel is at least 2 times, at least 3 times, at least 4 times, at least 5 times, at least 10 times, at least 20 times or at least 25 times the mole amount of the first polymer in the hydrogel.

In alternative embodiments, the first polymer may be present in weight excess and/or mole excess of the second polymer by the amounts specified above.

During the preparation of the hydrogel, the concentration and volumes of polymer in the aqueous preparation mixtures may be selected so as to provide the desired amounts of the first and second polymers in the hydrogel product. Thus the weight amounts referred to above may refer to the weight amounts in the aqueous compositions comprising the first and second polymers, from which the network is obtained or obtainable.

The references above to the amount of polymer present in the hydrogel refer to the amount of polymer including its guest functionality.

In one embodiment, the total amount of cucurbituril present in the hydrogel is equal to amount, by weight, of a polymer present in the hydrogel. For example, where a polymer is present at 0.1 wt %, the cucurbituril may also be present at 0.1 wt %. For convenience, this may be referred to as 1 equivalent.

In one embodiment, the cucurbituril is present at least at 0.9, at least at 0.8, at least at 0.5, at least at 0.2 or at least at 0.1 equivalents to a polymer present in the hydrogel. In one embodiment, the cucurbituril is present at most 10, at most 5, at most 4, at most 3 or at most 2 equivalents to a polymer present in the hydrogel.

In one embodiment, the amount of cucurbituril present in the hydrogel is in a range where the minimum and maximum amounts are selected from the embodiments above. For example, the amount of cucurbituril present is in the range 0.5 to 2 equivalents, for example 0.7 to 1.5 equivalents.

In one embodiment, the cucurbituril is present at about 1 equivalent.

Where, two polymers are present, for example a first and second polymer, the amount of cucurbituril may be with reference to either the first or the second polymer.

In one embodiment, the amount of crosslinking within the hydrogel is at most 10%, at most 8% or at most 5%.

In one embodiment, the amount of crosslinking within the hydrogel is at least 0.1%, at least 0.5%, at least 1% or at least 2%.

In one embodiment, the amount of crosslinking is in a range where the minimum and maximum amounts are selected from the embodiments above. For example, the amount of crosslinking is in the range 1 to 8%.

Crosslinking refers to the % of monomer units participating in cross-link formation and is determined by the molar equivalent addition of the cucurbituril with reference to the functionality of a polymer. Thus, the addition of 0.5 equivalents of cucurbituril relative to a polymer having 10% functionality present, gives a network having a crosslink value of 5%. Thus, 5% of all available monomers in the polymer participate in a crosslink. The crosslink value therefore assumes that all the available polymer guests participate in a complex with cucurbituril.

Where, two polymers are present, for example a first and second polymer, the crosslinking value may be expressed with reference to either the first or the second polymer.

In one embodiment, the hydrogel has a complex viscosity in a strain amplitude sweep measurement of at least 5, at least 7, or at least 10 Pa s.

In one embodiment, the hydrogel has a complex viscosity in a strain amplitude sweep measurement of at most 1,000, at most 500, or at most 100 Pa s.

In one embodiment, the complex viscosity value is the recorded at a strain in the range 9 to 90 Pa s or in the range 9 to 500 Pa s.

The complex viscosity value may be the value recorded at 37° C. from a strain amplitude sweep measurement and is the value taken at a strain value in the range 0.1 to 10%.

In one embodiment, the complex viscosity value in a strain amplitude sweep measurement is substantially the same across the strain range 0.1 to 100%, 0.1 to 10% or 1 to 10%.

In one embodiment, the hydrogel has a complex viscosity in a frequency sweep measurement of at least 10, at least 100, at least 200 or at least 300 Pa s.

The complex viscosity value may be the value recorded at 37° C. from a frequency sweep measurement and is the value taken at a frequency value in the range 0.1 to 10 rad/s, preferably the value recorded at 0.1 rad/s.

In one embodiment the complex viscosity values for the hydrogel decreases substantially linearly with increasing frequency in the frequency sweep measurement.

In one embodiment, the hydrogel has a viscosity of at least 60, at least 70, at least 80, at least 90 or least 100 Pa s.

In one embodiment, the hydrogel has a viscosity of at most 2,000, at most 3,000, or at most 5,000 Pa s.

In one embodiment, the hydrogel has a viscosity in the range 90 to 2,000 Pa s. The viscosity value may be the value recorded at low shear rates, for example at a shear rate in the range 0.1 to 0.5 1/s, for example 0.1 to 0.3 1/s. The viscosity value may be the value recorded at 25° C. in a steady shear measurement.

In one embodiment, the hydrogel exhibits a shear thinning behaviour across the range 0.3 to 10 1/s or in the range 1 to 10 1/s. Thus, the viscosity of the hydrogel reduces over this range of shear values. In contrast, the hydrogels of the prior art do not exhibit such behaviour. Rather, the viscosity of the prior art hydrogel remains substantially constant in these ranges, and exhibits a rapid collapse in viscosity at higher shear rates, for example at shear rates in excess of 30 1/s.

The storage modulus value (G') of the hydrogel may be the value recorded at 37° C. from a strain amplitude sweep measurement and is the value taken at a strain value in the range 0.1 to 100%, for example in the range 0.1 to 10%.

In one embodiment, the hydrogel has a storage modulus (from a strain amplitude sweep measurement) of at least 5 Pa, at least 10 Pa, at least 20 Pa, at least 50 Pa, or at least 100 Pa.

In one embodiment, the hydrogel has a storage modulus (from a strain amplitude sweep measurement) of at most 2,000 Pa, at most 1,500 Pa, or at most 1,000 Pa. In one embodiment, the hydrogel has a storage modulus (from a strain amplitude sweep measurement) in a range where the minimum and maximum amounts are selected from the embodiments above. For example, the storage modulus is in the range 10 to 1,000 Pa, for example 50 to 1,000 Pa.

Alternatively, the storage modulus value of the hydrogel may be the value recorded at 37° C. from a frequency sweep measurement and is the value taken at a frequency value in the range 0.1 to 100 rad/s, for example in the range 0.1 to 10 rad/s.

In one embodiment, the hydrogel has a storage modulus (from a frequency sweep measurement) of at least 4 Pa, at least 9 Pa, at least 10 Pa, or at least 20 Pa.

In one embodiment, the hydrogel has a storage modulus (from a frequency sweep measurement) of at most 500. At most 800 Pa, or at most 1,000 Pa.

In one embodiment, the hydrogel has a storage modulus (from a frequency sweep measurement) in a range where the minimum and maximum amounts are selected from the embodiments above. For example, the storage modulus is in the range 4 to 1,000 Pa, for example 10 to 1,000 Pa.

The loss modulus value (G") of the hydrogel may be the value recorded at 37° C. from a strain amplitude sweep measurement and is the value taken at a strain value in the range 0.1 to 100%, for example in the range 0.1 to 10%.

In one embodiment, the hydrogel has a loss modulus (from a strain amplitude sweep measurement) of at least 5 Pa, at least 10 Pa or at least 20 Pa.

In one embodiment, the hydrogel has a loss modulus (from a strain amplitude sweep measurement) of at most 200 Pa, at most 500 Pa, or at most 1,000 Pa.

In one embodiment, the hydrogel has a loss modulus (from a strain amplitude sweep measurement) in a range where the minimum and maximum amounts are selected from the embodiments above. For example, the loss modulus is in the range 10 to 1,000 Pa, for example 20 to 1,000 Pa.

Alternatively, the loss modulus value of the hydrogel may be the value recorded at 37° C. from a frequency sweep measurement and is the value taken at a frequency value in the range 0.1 to 100 rad/s, for example in the range 0.1 to 10 rad/s.

In one embodiment, the hydrogel has a loss modulus (from a frequency sweep measurement) of at least 1 Pa, at least 5 Pa, at least 10 Pa, or at least 20 Pa.

In one embodiment, the hydrogel has a loss modulus (from a frequency sweep measurement) of at most 200 Pa, at most 500 Pa, or at most 1,000 Pa.

In one embodiment, the hydrogel has a loss modulus (from a frequency sweep measurement) in a range where the minimum and maximum amounts are selected from the embodiments above. For example, the loss modulus is in the range 1 to 1,000 Pa, for example 10 to 500 Pa.

In one embodiment, the storage modulus and/or the loss modulus value is substantially the same across the strain range 0.1 to 100%, 0.1 to 10% or 1 to 10%. The present inventors have found that the hydrogels of the invention have an extremely broad linear viscoelastic region. Only where the total polymer content in the hydrogel is high (for example at 1.5 wt % or greater) does the hydrogel begin to show a deviation from linear viscoelasticity, for example at a strain value of 10% or more.

In one embodiment, the loss modulus is not greater than the storage modulus for any frequency value in the range 0.1 to 100 rad/s for a hydrogel analysed by frequency sweep measurement at 37° C. Thus, the storage modulus for the hydrogels is dominant.

Figure 2:
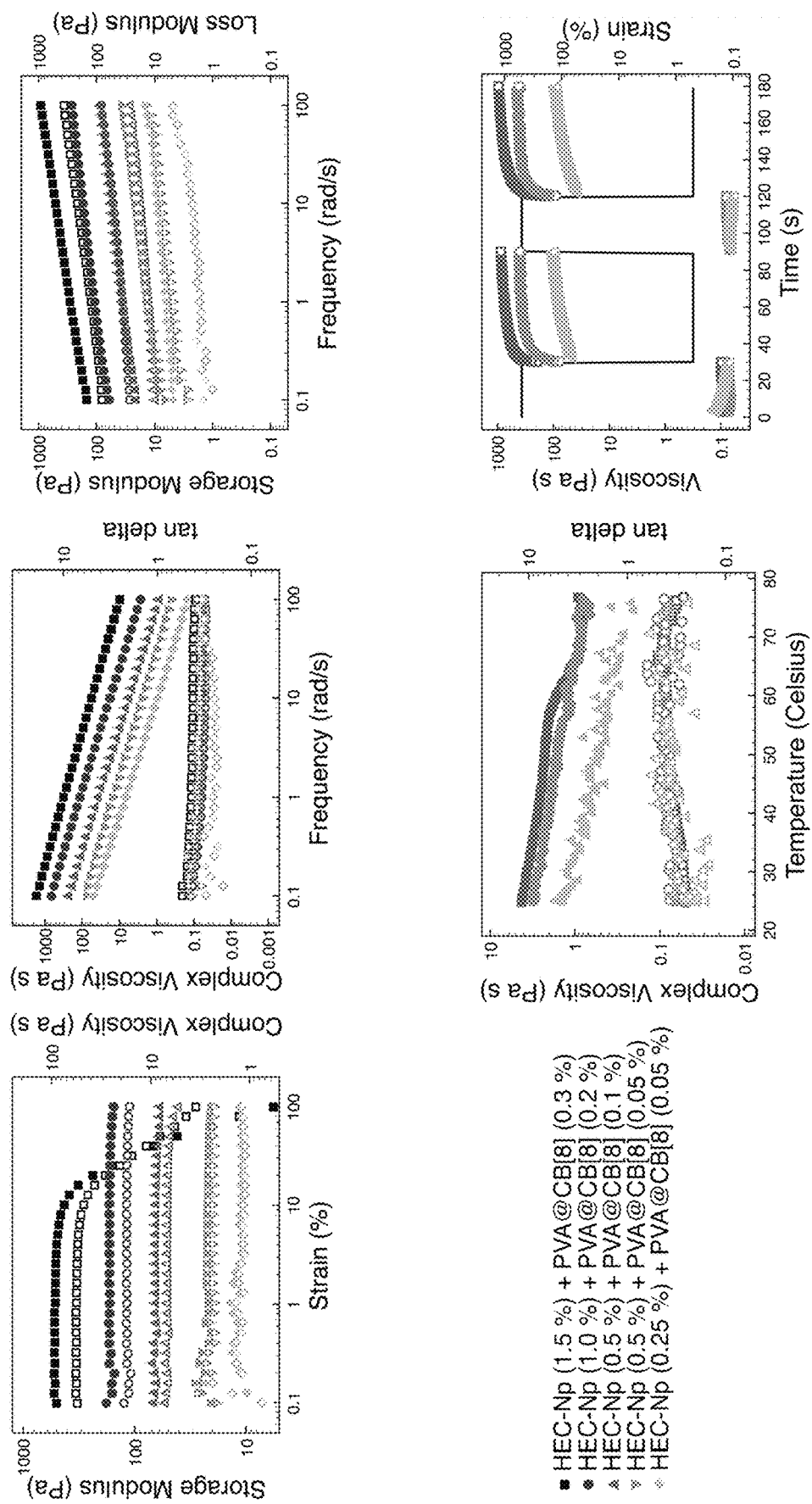
FIG. 2 shows the recorded data relating to the rheological analysis of the hydrogels of the invention. The graphs in the top row show the effect of HEC-Np loading and the relative loading of HEC-Np and PVA-MV@CB[8] (i.e. 1:1 ratio of PVA-MV to CB[8]) on storage modulus, loss modulus. complex viscosity and tan delta; The graphs in the bottom row show the thermal stability of hydrogels determined by a dynamic oscillatory temperature sweep test (bottom left); and step rate time sweep measurements displaying recovery of hydrogel structure following high magnitude deformation (bottom right). Symbol denotations are as follows: HEC-Np (1.5 wt %)/PVA-MV (0.3 wt %) (■), HEC-Np (1.0 wt %)/PVA-MV (0.2 wt %) (•), HEC-Np (0.5 wt %)/PVA-MV (0.1 wt %) (▲), HEC-Np (0.5 wt %)/PVA-MV (0.05 wt %) (▼), HEC-Np (0.25 wt %)/PVA-MV (0.05 wt %) (◆). The filled symbols refer to the parameter on the left axis, and the unfilled versions of the symbols refer to the parameter on the right axis.

In one embodiment, the changes in storage and loss values with change in frequency (in a frequency sweep experiment) are substantially the same. Thus, the storage and loss moduli may be said to be parallel. The parallel nature of the modulus values is apparent in a frequency sweep experiment, where the strain (as %) and the modulus (as Pa) are both expressed on a logarithmic scale. Such is as shown in FIG. 2 of the present case.

Where a strain amplitude sweep measurement is recorded, the frequency may be set to 10 rad/s.

Where a frequency sweep measurement is recorded, the strain amplitude may be set at 5% strain. Alternatively, the strain amplitude may be set at 10% strain. The skilled person will choose a strain value that is appropriate for the material under investigation. The skilled person will understand that the strain values are selected such that the frequency sweeps are performed in the linear viscoelastic regions for the material.

The tan δ value of the hydrogel is recorded at 37° C. from a frequency sweep measurement and is the value taken at a frequency value in the range 1 to 100 rad/s.

In one embodiment, the hydrogel has a tan δ value (from a frequency sweep measurement) of at least 0.1, at least 0.2, or at least 0.3.

In one embodiment, the hydrogel has a tan δ value (from a frequency sweep measurement) of at most 0.4, at most 0.5 or at most 1.0.

In one embodiment, the hydrogel has a tan δ value (from a frequency sweep measurement) in a range where the minimum and maximum amounts are selected from the embodiments above. For example, the tan δ value is in the range 0.1 to 0.5, for example 0.2 to 0.5.

Alternatively, the tan δ value may be the value recorded at 37° C. from a strain amplitude sweep measurement and is the value taken at a strain value in the range 0.1 to 10%.

In one embodiment, the hydrogel has a tan δ value (from a strain amplitude sweep measurement) of at least 0.1, at least 0.2 or at least 0.4.

In one embodiment, the hydrogel has a tan δ value (from a strain amplitude sweep measurement) of at most 0.5, at most 0.1, or at most 2.0.

In one embodiment, the hydrogel has a tan δ value (from a strain amplitude sweep measurement) in a range where the minimum and maximum amounts are selected from the embodiments above. For example, the tan δ value is in the range 0.1 to 0.5, for example 0.2 to 0.4.

In one embodiment, the tan δ value is substantially the same across the strain range 0.1 to 100%, 0.1 to 10% or 1 to 10%.

The inventors have found that the hydrogels of the invention are highly elastic and have recorded tan δ values of approx. 0.3, as measured from a frequency sweep measurement.

The hydrogels of the invention may be heated without significant loss of mechanical integrity.

In one embodiment, a hydrogel heated to a temperature of 30° C., 40° C., 50° C., or 60° C. has a complex viscosity of 1 Pa s or more.

In one embodiment, a hydrogel heated to a temperature of 30° C., 40° C., 50° C., or 60° C. has a complex viscosity of 2 Pa s or more.

In one embodiment, a hydrogel heated to a temperature of 30° C., 40° C., 50° C., or 60° C. has a tan δ value of 0.30 or less.

In one embodiment, a hydrogel heated to a temperature of 30° C., 40° C., 50° C., or 60° C. has a tan δ value of 0.35 or less.

In one embodiment, a hydrogel heated to a temperature of 30° C., 40° C., 50° C., or 60° C. has a tan δ value of 0.40 or less.

The complex viscosity and tan values set out above may be recorded in a dynamic oscillatory temperature sweep test.

As the temperature of the hydrogel increase, the bulk material properties generally decrease, as the association complex, for example for a network based on cucurbituril ternary complexes, the association constant decreases.

The hydrogels of the present invention have excellent reforming characteristics when deformed. A hydrogel that is exposed to a high magnitude shear rate, for example where 'γ' is 500 s$^{-1}$, reassembles quickly and completely. Thus, the original viscosity properties of the original hydrogel may be re-obtained upon reassembly of the hydrogel following the perturbation.

In one embodiment, a rheological property of the hydrogel remains substantially the same following at least one cycle of deformation and reassembly, such as two cycles of deformation and reassembly. The rheological property may be one or more properties selected from the group consisting of complex viscosity, storage modules, loss modulus, and tan δ.

The response of the hydrogel to the deformation cycle demonstrates the strength of a cucurbituril-based network to reversibly form strong hydrogel structures.

The physical properties of a hydrogel, as described above may refer to a hydrogel that does not hold a component. In other embodiments, the properties may refer to the hydrogel holding a component, though this is less preferred.

In one embodiment, the hydrogel has a correlation length in the range 150 to 250 Å, such as 170 to 230 Å, such as 180 to 220 Å. These values may be obtained by a combination of Debye-Bueche and Ornstein-Zerniche models, as described herein.

In one embodiment, the correlation length of the frozen-in hydrogel structure, Ξ, is in the range 500 to 1000 Å, such as 600 to 900 Å. These values may be obtained from the results of a SANS analysis, such as described below.

The correlation length values typically differ from those reported elsewhere for other polymeric gel structures. However, this difference is believed to be as a result of the unusually low total polymer amounts that are typically used in the hydrogels of the present invention. The correlation length values are consistent with the calculated mesh size, which is based on the distances between guest molecule functionality along a polymer.

In one embodiment, the hydrogel is transparent to light having a wavelength in the visible range, for example a wavelength in the range 380 to 740 nm.

Generally, the shape, dimensions and volume of the hydrogel are not particularly limited.

In one embodiment, the hydrogel has a largest cross-section of at most 100 cm, at most 50 cm, at most 35 cm, at most 10 cm.

In one embodiment, the hydrogel has a smallest cross-section of at least 100 nm, at least 1.0 μm, at least 10 μm, at least 100 μm, at least 1 mm, or at least 10 mm.

In one embodiment, the hydrogel has a cross-section where the minimum and maximum values are selected from the embodiments above. For example, the hydrogel has a cross-section in the range 1 mm to 10 cm.

The dimensions and the shape of the hydrogel may be dictated by the dimensions of the vessel in which the hydrogel is formed. For example, a hydrogel having a largest cross-section of around 1 cm is obtainable from a complexable composition held in a vial, such as a 15×45 mm vial. Examples of hydrogels formed in such vials are exemplified herein.

In one embodiment, a hydrogel of the invention is obtainable or obtained by the methods for the preparation of hydrogels as described herein.

The hydrogel is not a supramolecular capsule. Such capsules have a shell that is a supramolecular cross-linked network. A capsule has a substantial internal cavity that is free of the supramolecular cross-linked network. The hydrogels of the invention do not take the form of a capsule. The hydrogels of the invention have an extensive network of inter- and intra-linked polymers. This network does not provide for substantial internal cavities that are free of the supramolecular cross-linked network. The hydrogels of the invention may be further distinguished over supramolecular capsules by virtue of their beneficial rheological properties, such as those properties described above.

Complex

The hydrogel is a network that is held together by a supramolecular handcuff. The complex that forms this supramolecular handcuff is based on a cucurbituril hosting one guest (binary complex) or two guests (ternary complex). The cucurbituril forms a non-covalent bond to each guest. The present inventors have established that complexes of cucurbituril are readily formed and provide robust non-covalent linkages between polymer building blocks. The formation of the complex is tolerant of many functionalities within the polymers. One of the present inventors has demonstrated that polymer networks, including a basic hydrogel, may be prepared using a cucurbituril handcuff. However, until now, the formation of cucurbituril-based hydrogels having useful physical characteristics has not been described. The formation of cucurbituril-based hydrogels that are capable of holding a component within have also not apparently been described.

As noted above, the complex of cucurbituril with one or two guests is the non-covalent link that links and/or interlinks the polymers to from a supramolecular network of material.

In one embodiment, the hydrogel is a network having a plurality of complexes, wherein each complex comprises cucurbituril hosting a first guest molecule and a second guest molecule. The first and second guest molecules are covalently linked to a first polymer, or to a first polymer and a second polymer.

Where the complex comprises two guests within the cucurbituril cavity, the association constant, $K_a$, for that complex is at least $10^3$ $M^{-2}$, at least $10^4$ $M^{-2}$, at least $10^5$ $M^{-2}$, at least $10^6$ $M^{-2}$, at least $10^7$ $M^{-2}$, at least $10^8$ $M^{-2}$, at least $10^9$ $M^{-2}$, at least $10^{10}$ $M^{-2}$, at least $10^{11}$ $M^{-2}$, or at least $10^{12}$ $M^{-2}$.

Where a cucurbituril hosts two guest molecules, the guest molecules may be the same or they may be different. A cucurbituril that is capable of hosting two guest molecules may also be capable of forming a stable binary complex with a single guest. The formation of a ternary guest-host complex is believed to proceed via an intermediate binary complex. Within a hydrogel of the invention, there may be present a binary complex formed between a guest molecule and a cucurbituril. The binary complex may be regarded as a partially formed ternary complex that has not yet formed a non-covalent bond to another guest molecule.

In one embodiment, the hydrogel is a network having a plurality of complexes, wherein each complex comprises cucurbituril hosting one guest molecule, and each cucurbituril is covalently linked to at least one other cucurbituril. The guest molecules are covalently linked to a first polymer, or to a first polymer and a second polymer.

Where the complex comprises one guest within the cucurbituril cavity, the association constant, $K_a$, for that complex is at least $10^3$ $M^{-1}$, of at least $10^4$ $M^{-1}$, of at least $10^5$ $M^{-1}$, of at least $10^6$ $M^{-1}$, of at least $10^7$ $M^{-1}$, of at least $10^8$ $M^{-1}$, of at least $10^9$ $M^{-1}$, of at least $10^{10}$ $M^{-1}$, of at least $10^{11}$ $M^{-1}$, or of at least $10^{12}$ $M^{-1}$.

In one embodiment, the guest is a compound capable of forming a complex which has an association constant in the range $10^4$ to $10^7$ $M^{-1}$.

In one embodiment the formation of the complex is reversible. The separation of a guest from the cucurbituril host, thereby to sever a link or crosslink with a polymer, may be referred to as decomplexation.

The decomplexation of the complex to separate the guest or guests may occur in response to an external stimulus, including, for example, a competitor guest compound, light, an oxidising or reducing agent, electrochemical potential, and temperature changes amongst others. Such decomplexation may be induced in order to provide additional or larger pores in the hydrogel through which a component that is held in the hydrogel may pass. Decomplexation may also be used to disrupt the entire network and bring about the breakdown of the hydrogel.

As described herein, a competitive guest for use in the decomplexation of a CB[8]-based network is 2,6-dihydroxynapthalene or toluene. The competitor guest may be used in excess to the amount (mole amount) of guest molecules present on the polymers of the network. In one embodiment, the competitive guest has a higher association constant than a guest of the complex.

In other embodiments, decomplexation of the network, and therefore the hydrogel, is achieved by the oxidation or reduction of a guest in a complex. The change in oxidation state of a guest may be achieved using a chemical oxidising or reducing agent, or the application of an electrochemical potential. As described herein, a complex comprising a viologen, such as a methyl viologen, may be decomplexed by treatment with a reducing agent, such as a dithionite.

In one embodiment, the decomplexation reaction is reversible. Thus, a hydrogel may be converted to a low viscosity, decomplexed form, then returned to a high viscosity, hydrogel form, as appropriate, which may be the same or different to the original hydrogel.

Network Structure

As noted above, the hydrogels of the present invention are based upon a network that is formed from the complexation of cucurbituril, as a host, together with a guest (binary complex) or two guests (ternary complex). The guest or guests are covalently attached to polymers, which provide the gross network structure. The nature of the network depends on the form of complex used (binary or tertiary), which in turn is based on the cucurbituril and the guests employed. The number and nature of the polymer is also relevant.

Two types of network are provided. The first type is based on the formation of a plurality of ternary complexes, each complex comprising a cucurbituril host with a first guest molecule and a second guest molecule. The second type is based on the formation of a plurality of binary complexes, each complex comprising a cucurbituril host with a first guest molecule. In this second type, each cucurbituril is covalently linked to a least one other cucurbituril. These types of network may be combined within a hydrogel of the invention.

Where a polymer is provided with a plurality of guest molecules, all of the guest molecules need not participate in a complex with cucurbituril. Where the network is based on linking between ternary structures, a guest molecule of a building block (polymer) may be in a binary complex with a cucurbituril. The binary complex may be regarded as a partially formed ternary complex that has not yet combined with a further guest molecule to generate the ternary form.

Throughout the description references are made to a polymer, a first polymer and a second polymer. It is understood that a reference to such is a reference to a collection of the individual polymers etc. that are the building blocks (polymers). Where a reference is intended to an individual polymer molecule, the term single is used in reference to the building blocks e.g. a single first polymer.

The networks described below are the basic networks that are obtainable from the compositions described. It is understood that the present inventions extends to more complex networks that are obtainable from compositions comprising further polymers.

Network of Ternary Complexes Based on Cucurbituril

This network is obtainable from the complexation of a first guest molecule and a second guest molecule together with a cucurbituril host. The guest molecules may be provided on one or two (or more) polymers as described below. As described herein a network may be formed using only one polymer. That polymer may have guest molecules that are different (the first and second guests are not the same) or the same (the first and second guests are the same).

In one embodiment, a network is obtainable or obtained from the complexation of a composition comprising a cucurbituril, a first polymer covalently linked to a plurality of first cucurbituril guest molecules and a second polymer covalently linked to a plurality of second cucurbituril guest molecules, wherein a first guest molecule and a second guest molecule together with cucurbituril are suitable for forming a ternary guest-host complex.

The ternary complex serves to non-covalently link the first and second polymers. A single first polymer may form a plurality of non-covalent links to a plurality of second polymers. Similarly, a single second polymer may form a plurality of non-covalent links to a plurality of first polymers. In this way, a network of material is established.

It is noted that in some embodiments, the first and second guest molecules may be identical. Therefore the first and second polymers may differ in their compositions. In some embodiments, the first and second polymers may be identical. In this case, the first and second guest molecules are different.

Figure 26:
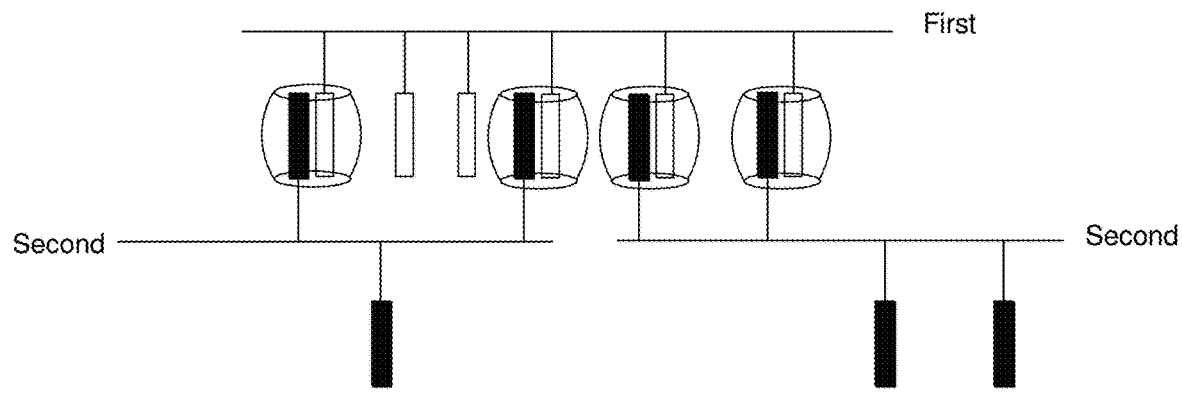
FIG. 26 is an illustration of a schematic structure of a basic network formed between cucurbituril, a single first polymer and two single second polymers. In the schematic, the guest molecules are depicted as rectangles which are covalently linked (vertical line) to a building block (horizontal line). The vertical line may depict a direct covalent bond or a linker to the polymer. Some of the first guest molecules (unshaded rectangles) of the first polymer are in complex with cucurbituril hosts (barrels) and second guest molecules (shaded rectangles) of the second polymers.

FIG. 26 is an illustration of a schematic structure of a basic network formed between cucurbituril, a single first polymer and two single second polymers. In the schematics included in this text, the guest molecules are depicted as rectangles which are covalently linked (vertical line) to a building block (horizontal line). The vertical line may depict a direct covalent bond or a linker to the polymer.

In FIG. 26, some of the first guest molecules (unshaded rectangles) of the first polymer are in complex with cucurbituril hosts (barrels) and second guest molecules (shaded rectangles) of the second polymers.

It is apparent that not all guest molecules present need participate in a complex in the final network. Each of the first and second polymers may form complexes with other second and first polymers respectively. The guest molecules are shaded for ease of understanding. However, as explained herein, the guest molecules of the first and second building blocks may be the same.

In an alternative embodiment, a network is obtainable or obtained from the complexation of a composition comprising a cucurbituril and a first polymer covalently linked to a plurality of first cucurbituril guest molecules and a plurality of second cucurbituril guest molecules, wherein a first and a second guest molecule together with cucurbituril are suitable for forming a ternary guest-host complex. As noted above, the first and second guest molecules may be the same or different.

The ternary complex serves to non-covalently link and/or interlink the first polymer. A single first polymer may form a plurality of non-covalent links to a plurality of other first polymers. Additionally, or alternatively, a single first polymer may form a plurality of non-covalent interlinks with itself, thereby to crosslink the single first building block. As before, the first and second guest molecules may be identical.

Figure 27:
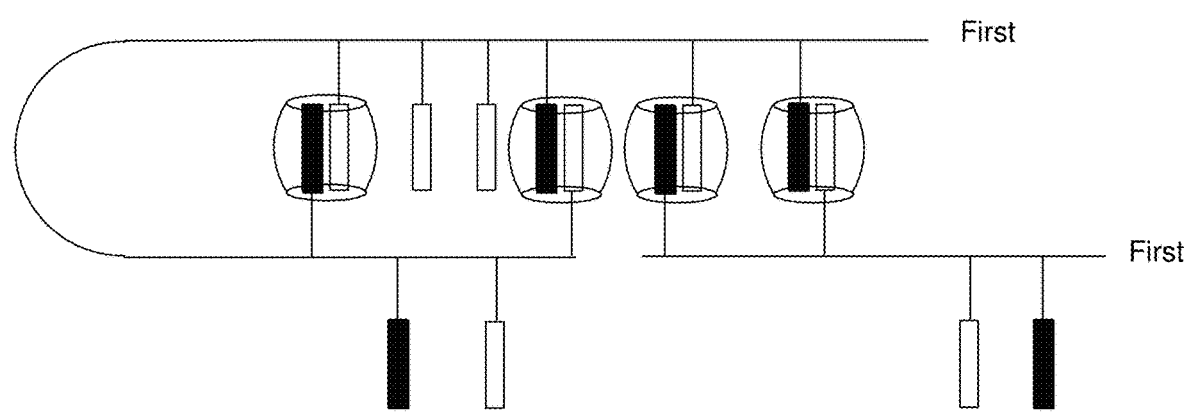
FIG. 27 is an illustration of a schematic structure of a basic network formed between cucurbituril and two single first polymers each having a plurality of first and second guest molecules. Some of the first guest molecules (unshaded rectangles) of the first polymer are in complex with cucurbituril hosts (barrels) and second guest molecules (shaded rectangles) of another first polymer. It can be seen from the network illustrated that a first building block may form intramolecular complexes, thereby crosslinking a single first polymer.

FIG. 27 is an illustration of a schematic structure of a basic network formed between cucurbituril and two single first polymers each having a plurality of first and second guest molecules. Some of the first guest molecules (unshaded rectangles) of the first polymer are in complex with cucurbituril hosts (barrels) and second guest molecules (shaded rectangles) of another first polymer. It can be seen from the network illustrated that a first building block may form intramolecular complexes, thereby crosslinking a single first polymer.

It is apparent that not all guest molecules present need participate in a complex in the final network. Each of the first building blocks may form complexes with other first polymer, or with other parts of the same polymer. As explained herein, the first and second guest molecules may be the same.

Optionally, the composition further comprises a second polymer covalently linked to one or more third cucurbituril guest molecules, one or more fourth cucurbituril guest molecules or both, wherein a third and a fourth molecule together with cucurbituril are suitable for forming a ternary guest-host complex, or the first and fourth guest molecules together with cucurbituril are suitable for forming a ternary guest-host complex, or the second and third guest molecules together with cucurbituril are suitable for forming a ternary guest-host complex.

Where the second polymer is provided with a plurality of third and fourth guest molecules, the ternary complex serves to non-covalently link and/or interlink the second polymer. A single second polymer may form a plurality of non-covalent links to a plurality of other second polymer. Additionally, or alternatively, a single second polymer may form one or more non-covalent interlinks with itself, thereby to crosslink the single second polymer.

The third and fourth guest molecules may be suitable for forming complexes with the first and second guest molecules of the first polymer. In one embodiment, the first and third guest molecules are the same. In one embodiment the second and fourth guest molecules are the same. Here, the ternary complex serves to non-covalently link the first and second polymers, for example through a complex of the first and fourth guest molecules and/or through a complex of the second and third guest molecules.

Thus, a single first polymer may form a plurality of non-covalent links to a plurality of second polymers. Similarly, a single second polymer may form a plurality of non-covalent links to a plurality of first polymers. In this way, a network of material is established. The polymers may also form intermolecular non-covalent bonds as described previously.

Where a second polymer is covalently linked to one or more third guest molecules or one or more fourth guest molecule, the first and fourth molecules together with cucurbituril are suitable for forming a ternary guest-host complex, and the second and third molecules together with cucurbituril are suitable for forming a ternary guest-host complex.

Thus, the ternary complex serves to non-covalently link the second polymer to the first polymer.

Figure 28:
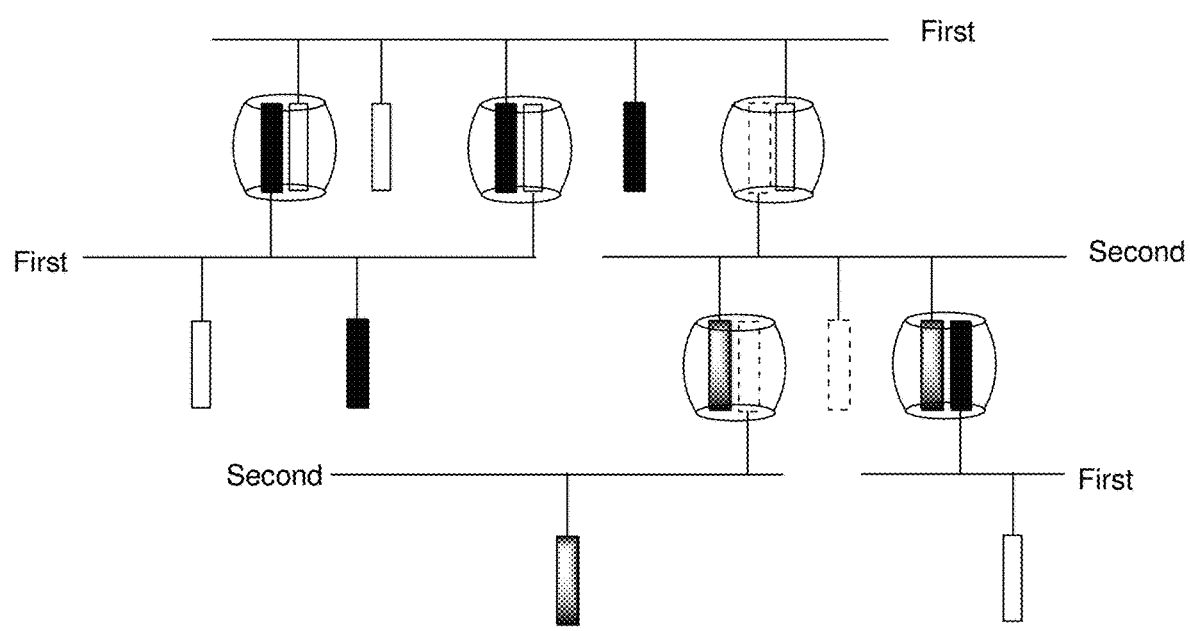
FIG. 28 is an illustration of a schematic structure of a basic network formed between cucurbituril, three single first building blocks each having a plurality of first and second guest molecules, and two second building blocks each having a plurality of third and fourth guest molecules. Some of the first guest molecules (unshaded rectangles) of the first building block are in complex with cucurbituril hosts (barrels) and second guest molecules (shaded rectangles) of another first building block. Some of the third guest molecules (partially shaded rectangles) of the second building block are in complex with cucurbituril hosts (barrels) and fourth guest molecules (dashed rectangles) of another second building block. A the first guest molecule of the first building block is in complex with a cucurbituril host and a fourth guest molecule (dashed rectangles) of a second building block. A second guest molecule of the first building block is in complex with a cucurbituril host and a third guest molecule of a second building block.

FIG. 28 is an illustration of a schematic structure of a basic network formed between cucurbituril, three single first building blocks each having a plurality of first and second guest molecules, and two second building blocks each having a plurality of third and fourth guest molecules. Some of the first guest molecules (unshaded rectangles) of the first building block are in complex with cucurbituril hosts (barrels) and second guest molecules (shaded rectangles) of another first building block. Some of the third guest molecules (partially shaded rectangles) of the second building block are in complex with cucurbituril hosts (barrels) and fourth guest molecules (dashed rectangles) of another second building block. A the first guest molecule of the first building block is in complex with a cucurbituril host and a fourth guest molecule (dashed rectangles) of a second building block. A second guest molecule of the first building block is in complex with a cucurbituril host and a third guest molecule of a second building block.

The first and third guest molecules may be the same. The second and fourth guest molecules may be the same.

Network of Binary Complexes Based on a Plurality of Covalently Linked Cucurbiturils This network is obtainable from the complexation of a first guest molecule with a cucurbituril host, which host is covalently linked to one or more other cucurbiturils. The guest molecules may be provided on one, or two (or more) polymers as described herein.

The covalently linked cucurbiturils serve to link polymer molecules through the plurality of complexes that are formed within each of the covalently linked cucurbiturils.

Figure 29:
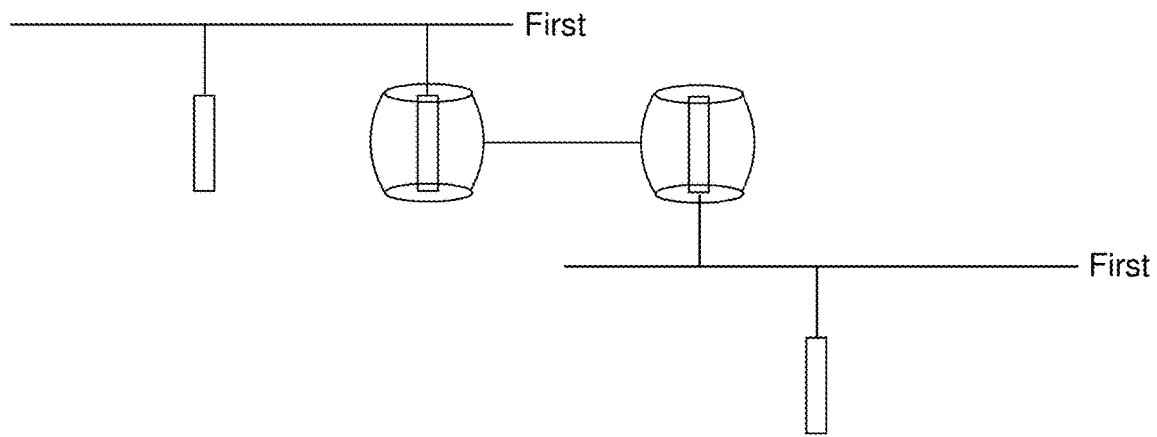
FIG. 29 is an illustration of a schematic structure of a basic network formed between a plurality of covalently linked cucurbiturils and two single first polymers each having a plurality of first guest molecules. Some of the first guest molecules (unshaded rectangles) of each of the single first polymer are in a binary complex with cucurbituril hosts (barrel). The cucurbiturils are covalently linked, thereby to form a link between each of the first building blocks. The cucurbiturils may be covalently linked via a polymer.

FIG. 29 is an illustration of a schematic structure of a basic network formed between a plurality of covalently linked cucurbiturils and two single first polymers each having a plurality of first guest molecules. Some of the first guest molecules (unshaded rectangles) of each of the single first polymer are in a binary complex with cucurbituril hosts (barrel). The cucurbiturils are covalently linked, thereby to form a link between each of the first building blocks. The cucurbiturils may be covalently linked via a polymer.

It is apparent that not all guest molecules present need participate in a complex in the final network. Each of the single first building blocks may form complexes with other first polymers respectively, or may form an intramolecular crosslink with another portion of the same polymer. As explained herein, the guest molecules of the first and second polymers may be the same. In the schematic above, one of the first polymers may be replaced with a second polymer which is covalently linked to a second guest molecule. The second guest molecule is one that is capable of forming a binary complex with the cucurbituril. The second guest molecule may be the same as the first guest molecule.

In the schematic two cucurbiturils are shown linked together. The present invention encompasses the use of systems where more than two cucurbiturils are linked together. For example, multiple cucurbiturils may be pendant to a polymer, such as a polymer described herein.

Network of Ternary Complexes Based on a Plurality of Covalently Linked Cucurbiturils It will be apparent from the description of the networks above, that each of the cucurbituril hosts in the plurality of covalently linked cucurbiturils may be suitable for forming ternary complexes. Thus, the plurality of covalently linked cucurbiturils may be used in place of the cucurbituril described for use in the network of ternary complexes based on cucurbituril.

Figure 30:
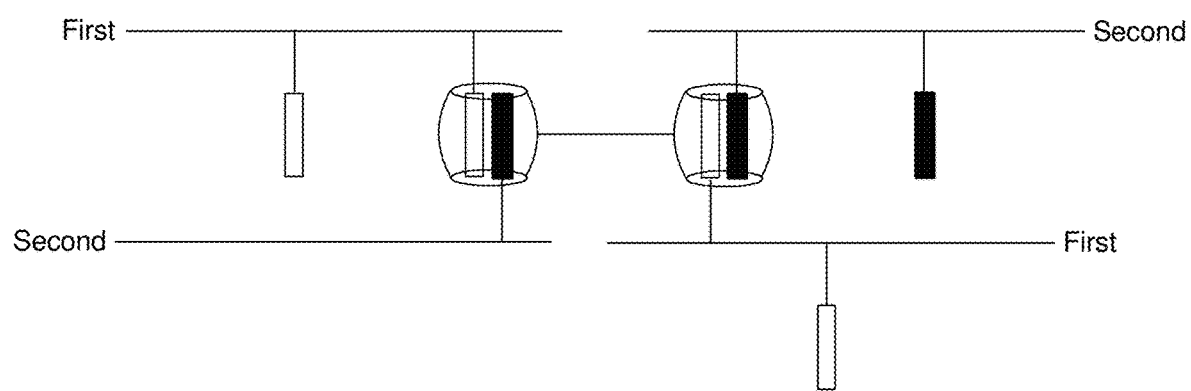
FIG. 30 is an illustration of a structural schematic of a basic network formed between a plurality of covalently linked cucurbiturils, two single first polymers each having a plurality of first guest molecules, and two single second polymers each having a plurality of second guest molecules. Some of the first guest molecules (unshaded rectangles) of the first polymer are in tertiary complex with a cucurbituril host (barrel) and the second guest molecules (shaded rectangles) of the second polymer. The cucurbiturils are linked, thereby to form a link between each of the first and second polymers.

FIG. 30 is an illustration of a structural schematic of a basic network formed between a plurality of covalently linked cucurbiturils, two single first polymers each having a plurality of first guest molecules, and two single second polymers each having a plurality of second guest molecules. Some of the first guest molecules (unshaded rectangles) of the first polymer are in tertiary complex with a cucurbituril host (barrel) and the second guest molecules (shaded rectangles) of the second polymer. The cucurbiturils are linked, thereby to form a link between each of the first and second polymers.

As before, the first and second guest molecules may be the same. Each of the first and second polymers may form complexes with other second and first polymers respectively. Other permutations are possible, for example, where the plurality of covalently linked cucurbiturils has greater than two cucurbiturils.

Other Networks

Described above are the basic networks of the invention that are obtained or obtainable from the compositions described. It will be clear to one of skill in the art that the compositions described may include further building blocks, for example third and fourth polymers, each linked to one or more cucurbituril guest molecules. The present invention also covers networks comprising a mixture of any one of the networks described above. Such are obtainable from compositions comprising an appropriate selection of cucurbituril, covalently linked cucurbiturils, first polymer and second polymer as appropriate.

The invention also relates to a network comprising different cucurbiturils. Different cucurbiturils may be chosen in order to obtain a network that is based on ternary and binary complexes. Different cucurbiturils may be chosen in order to generate networks that result from the selective complexation of each cucurbituril for different guest molecules, which may be present on the same or different polymers.

Cucurbituril

The present invention provides use of cucurbituril as a supramolecular handcuff to link and/or crosslink polymers. The cucurbituril may be used to form ternary complexes with first and second guest molecules present on one or more polymers. The formation of such complexes links individual polymer molecules thereby to form a network of material. Together with water, this network forms the hydrogel.

Recent work has shown that cucurbituril compounds have high in vitro and in vivo biocompatibility and have extremely low toxicity (see Uzunova et al. *Org. Biomol. Chem.* 2010, 8, 2037-2042). Thus, when used together with non-toxic polymer components, the present hydrogels are also suitable for use in biological systems.

In one embodiment, the cucurbituril is capable of forming a ternary complex. For example, CB[8], is capable of forming a ternary complex. As too are CB[9], CB[10], CB[11] and CB[12] compounds.

In one embodiment, the cucurbituril is capable of forming a binary complex. For example, CB[7], is capable of forming a ternary complex. As too is CB[8] with the appropriate guest molecule.

In one embodiment, the cucurbituril is a CB[8], CB[9], CB[10], CB[11] or CB[12] compound.

In one embodiment, the cucurbituril is a CB[8] compound.

References to a cucurbituril compound are references to variants and derivatives thereof.

In one embodiment, the cucurbituril compound has a solubility of at least 0.01 mg/mL, at least 0.02 mg/mL, at least 0.05 mg/mL, or at least 0.10 mg/mL.

In one embodiment, the solubility refers to aqueous solubility.

Cucurbit[8]uril (CB[8]; CAS 259886-51-6) is a barrel shaped container molecule which has eight repeat glycoluril units and an internal cavity size of 479A$^3$ (see structure below). CB[8] is readily synthesised using standard techniques and is available commercially (e.g. Sigma-Aldrich, Mo. USA).

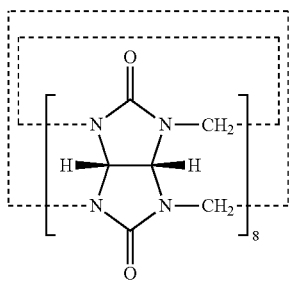

In other aspects of the invention, CB[8] variants are provided and find use in the methods described herein.

A variant of CB[8] may include a structure having one or more repeat units that are structurally analogous to glycoluril. The repeat unit may include an ethylurea unit. Where all the units are ethylurea units, the variant is a hemicucurbituril. The variant may be a hemicucurbit[12]uril (shown below, see also Lagona et al. *Angew. Chem. Int. Ed.* 2005, 44, 4844).

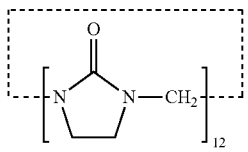

In other aspects of the invention, cucurbituril derivatives are provided and find use in the methods described herein. A derivative of a cucurbituril is a structure having one, two, three, four or more substituted glycoluril units. A substituted cucurbituril compound may be represented by the structure below:

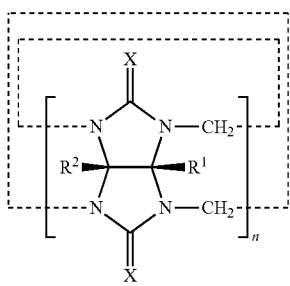

wherein:
n is an integer of at least 5;
and for each glycoluril unit
each X is O, S or NR$^3$, and
—R$^1$ and —R$^2$ are each independently selected from —H and the following optionally substituted groups: —R$^3$, —OH, —OR$^3$, —COOH, —COOR$^3$, —NH$_2$, —NHR$^3$ and —N(R$^3$)$_2$ where —R$^3$ is independently selected from C$_{1-20}$alkyl, C$_{6-20}$carboaryl, and C$_{5-20}$heteroaryl, or where —R$^1$ and/or —R$^2$ is —N(R$^3$)$_2$, both —R$^3$ together form a C$_{5-7}$ heterocyclic ring; or together —R$^1$ and —R$^2$ are C$_{4-6}$alkylene forming a C$_{6-8}$carbocyclic ring together with the uracil frame.

In one embodiment, one of the glycoluril units is a substituted glycoluril unit. Thus, —R$^1$ and —R$^2$ are each independently —H for n−1 of the glycoluril units.

In one embodiment, n is 5, 6, 7, 8, 9, 10, 11 or 12.
In one embodiment, n is 5, 6, 7, 8, 10 or 12.
In one embodiment, n is 8, 10 or 12.
In one embodiment, n is 8.
In one embodiment, n is 7.
In one embodiment, each X is O.
In one embodiment, each X is S.
In one embodiment, R$^1$ and R$^2$ are each independently H.
In one embodiment, for each unit one of R$^1$ and R$^2$ is H and the other is independently selected from —H and the following optionally substituted groups: —R$^3$, —OH, —OR$^3$, —COOH, —COOR$^3$, —NH$_2$, —NHR$^3$ and —N(R$^3$)$_2$. In one embodiment, for one unit one of R$^1$ and R$^2$ is H and the other is independently selected from —H and the following optionally substituted groups: —R$^3$, —OH, —OR$^3$, —COOH, —COOR$^3$, —NH$_2$, —NHR$^3$ and —N(R$^3$)$_2$. In this embodiment, the remaining glycoluril units are such that R$^1$ and R$^2$ are each independently H.

Preferably —R$^3$ is C$_{1-20}$alkyl, most preferably C$_{1-6}$ alkyl. The C$_{1-20}$alkyl group may be linear and/or saturated. Each group —R$^3$ may be independently unsubstituted or substituted. Preferred substituents are selected from: —R$^4$, —OH, —SH, —SR$^4$, —COOH, —COOR$^4$, —NH$_2$, —NHR$^4$ and —N(R$^4$)$_2$, wherein —R$^4$ is selected from C$_{1-20}$ alkyl, C$_{6-20}$ carboaryl, and C$_{5-20}$ heteroaryl. The substituents may be independently selected from —COOH and —COOR$^4$.

In some embodiments, —R$^4$ is not the same as —R$^3$. In some embodiments, —R$^4$ is preferably unsubstituted.

Where —R$^1$ and/or —R$^2$ is —OR$^3$, —NHR$^3$ or —N(R$^3$)$_2$, then —R$^3$ is preferably C$_{1-6}$alkyl. In some embodiments, —R$^3$ is substituted with a substituent —NHR$^4$ or —N(R$^4$)$_2$.

Each —R$^4$ is C$_{1-6}$ alkyl and is itself preferably substituted.

In some embodiments of the invention there is provided the use of a plurality of covalently linked cucurbiturils. Such covalently linked cucurbiturils are suitable for forming networks based on the complexation of the cucurbituril with guest molecules of a building block (polymer). The complexes formed may be ternary or binary complexes.

A cucurbituril may be covalently linked to another cucurbituril via a linker group that is a substituent at position R$^1$ or R$^2$ at one of the glycoluril units in the cucurbituril as represented in the structure shown above. There are no particular limitations on the covalent link between the cucurbiturils. The linker may be in the form of a simple alkylene group, a polyoxyalkylene group or a polymer, such as a polymer described herein (absent the guest functionality). Where the linker is a polymeric molecule, the cucurbiturils may be pendant to that polymer. Where the cucurbiturils are covalently linker by a polymer, that polymer may have the characteristics of the polymers described herein. For example, the polymer may have a high molecular weight, and the polymer may by hydrophilic. Such preferences are set out below in relation to the polymers having guest functionality.

Polymers

The network of the hydrogel of the invention is formed from the complexation of one or more polymers with a cucurbituril handcuff. Each polymer is provided with suitable guest functionality to interact with the cucurbituril host.

Some of the present inventors have previously described hydrogels that are networks formed from the complexation of CB[8] with a suitably functionalised polystyrene-based polymer and a suitably functionalised polyacrylamide-based polymer (Appel et al. *J. Am. Chem. Soc.* 2010, 132, 14251-14260). The molecular weight of each polymer is relatively low, and the polydispersity of one of the polymers, typically the polystyrene-based polymer, is relatively high. Additionally, the functionality of the polymers is high.

The present hydrogels are distinguishable over this earlier work for at least the reason that one of the polymers has a high molecular weight and/or a low functionality. In some embodiments, the polydispersity of all the polymers in the network is low. In other embodiments, the polymers present in the hydrogel comprise monomers having hydroxyl functionality.

Cucurbituril is used as a supramolecular handcuff to join together one or more polymers. The formation of a complex of the cucurbituril with suitable guest components that are linked to the polymers forms a network of material. The complex non-covalently crosslinks a polymer or non-covalently links a polymer to another polymer.

It is understood from the above that the polymer is an entity that serves to provide structure to the formed network. The polymer also serves as the link between a plurality of guest molecules, and it may therefore also be referred to as a linker. In some embodiments, a polymer is provided for the purpose of introducing a desirable physical or chemical characteristic into the formed network. A polymer may include a functionality to aid detection and characterisation of the network, or to aid detection and characterisation of a component that is held in the hydrogel. Such polymers need not necessarily participate in a crosslink.

A polymer may be selected for its molecular weight, polydispersity, solubility, and/or its mechanical and physical characteristics.

A polymer, such as a first polymer, is covalently linked to a plurality of cucurbituril guest molecules. A building block (polymer) will therefore non-covalently link to a plurality of cucurbiturils, which cucurbiturils will non-covalently link to other polymers, thereby to generate a network of material.

A polymer, such as a first polymer or a second polymer, may be covalently linked to a plurality of cucurbituril guest molecules. In one embodiment, a polymer is covalently linked to at least 3, at least 4, at least 5, at least 10, at least 20, at least 50, at least 100, at least 500, at least 1,000, at least 2,000, at least 5,000 or at least 10,000 cucurbituril guest molecules.

In certain embodiments, polymers covalently linked to one or more cucurbituril guest molecules may be used. However, such polymers are used only in combination with other polymers that are covalently linked to at least two cucurbituril guest molecules.

The number of guest molecules present in a particular polymer molecule may be expressed as the percentage of monomers present in the polymer that are attached to guest molecules as a total of all the monomers present in the polymeric molecule. This may be referred to as the functionality percentage.

In one embodiment, the functionality of a polymeric molecule is at least 0.1%, at least 0.2%, at least 0.5% or at least 1.0%.

In one embodiment, the functionality of a polymeric molecule is at most 20%, at most 15%, at most 10%, at most 7%, at most 5%, or at most 2%.

In one embodiment, the functionality is in a range where the minimum and maximum amounts are selected from the embodiments above. For example, the functionality is in the range 1 to 10%.

The functionality percentage may be determined from proton NMR measurements of a polymer sample.

In one embodiment, the network comprises a first polymer and a second polymer. One or more additional polymers may be provided, each having guest molecules, within the hydrogel. These additional polymers may be provided to further tune the mechanical and physical properties of the hydrogel.

In one embodiment, the first polymer is covalently linked to a plurality of first guest molecules and the second polymer is covalently linked to a plurality of second guest molecules. The hydrogel network is formed by linking the first polymer to the second polymer via non-covalent interactions of cucurbituril with first and second guest molecules. This is a network based on ternary complexation. Optionally, the first and second polymers may be linked to additional guest molecules.

In an alternative embodiment, the hydrogel comprises a first polymer. This first polymer is covalently linked to a plurality of first and second guest molecules. The hydrogel network may be formed by linking and crosslinking the first polymer via non-covalent interactions. This is a network based on ternary complexation.

In another embodiment, the hydrogel comprises a first polymer. This first polymer is covalently linked to a plurality of first guest molecules. The hydrogel network may be formed by linking and crosslinking the first polymer via non-covalent interactions. This is a network based on binary complexation. Optionally, a second polymer may also be provided which is covalently linked to one or more second guest molecules.

Advantageously, a polymer may be provided with certain functionality to aid the formation of the hydrogel, or to improve its physical or chemical properties. This functionality may be provide as poly functionality.

In one embodiment, the polymer is provided with functionality to alter, or preferably improve, interaction of the network with water. The functionality may take the form of a solubilising group, particularly an aqueous solubilising group, such as a group comprising polyethylene glycol functionality. Other examples include groups comprising amino, hydroxy, thiol, and carboxy functionality. In one embodiment, one or each polymer, such as one or both of the first polymer and the second polymer, may have hydroxy functionality.

In one embodiment, the polymer is provided with functionality to aid detection or analysis of the polymer, and to aid detection or analysis of the formed network. Advantageously, such functionality may also aid the detection of material encapsulated within the hydrogel. The functionality may take the form of a detectable label, such as a fluorescent label.

A polymer is linked to a cucurbituril guest molecule or guest molecules by covalent bonds. The covalent bond may be a carbon-carbon bond, a carbon-nitrogen bond, or a carbon-oxygen bond amongst others. The bond may be part of a linking group such as an ester or an amide, and/or part of a group comprising an alkylene or an alkoxylene functionality.

Each guest molecule may be linked to the polymer using routine chemical linkage techniques. For example, guest molecules may be linked to the polymer by: alkylation of a polymer bearing an appropriate leaving group; esterification reactions; amidation reactions; ether forming reactions; olefin cross metathesis; or small guest molecule initiated reactions in which a polymer chain is grown off an initiating guest molecule. Suitably functionalised polymers may also be prepared from suitably functionalised monomers, which may be used in a polymerisable composition optionally together with other monomers Examples of linkers for forming connection between a polymer and a guest molecule are described herein.

In one embodiment, the network comprises a polymer having a molecular weight (Mw) of 50 kDa or more, 100 kDa or more, 200 kDa or more, 500 kDa or more, 1.0 MDa or more, 1.5 MDa or more, 2.0 MDa or more, or 3.0 MDa or more.

In one embodiment, the polymer molecule has a molecular weight in the range 50 kDa to 4.0 MDa, such as 500 kDa to 4.0 MDa, such as 1.0 MDa to 4.0 MDa.

The molecular weight may refer to the number average molecular weight or the weight average molecular weight. The number average and weight average molecular weights of a polymer may be determined by conventional techniques.

Where the network comprises first and second polymer, optionally with further polymers, one of the polymers has a molecular weight selected from the values or ranges given above. Alternatively, both the first and second polymers, optionally as well as the further polymers present, have a molecular weight selected from the values or ranges given above.

In one embodiment, a polymer is a synthetic polydisperse polymer. A polydisperse polymer comprises polymeric molecules having a range of molecular masses. The polydispersity index (PDI) (weight average molecular weight divided by the number average molecular weight) of a polydisperse polymer is greater than 1, and may be in the range 5 to 20. The polydispersity of a polymeric molecule may be determined by conventional techniques such as gel permeation or size exclusion chromatography.

Particularly suitable for use in the present invention are polymers having a relatively low polydispersity. Such polymers may have a polydispersity in the range selected from 1 to 5, 1 to 3, 1 to 2, or 1 to 1.5. Such polymers may be referred to as low- or monodisperse in view of their relatively low dispersity. In one embodiment, a polymer has a polydispersity index in the range 1 to 1.5, such as 1 to 1.4, such as 1 to 1.3.

The network may comprise a polymer having a PDI value selected from the ranges given above. Where there are two, or more, polymers present in the network, each polymer may have a PDI value selected from the ranges given above.

The use of low- or monodisperse polymeric molecules is particularly attractive, as the reactively of individual molecules is relatively uniform, and the products that result from their use may also be physically and chemically relatively uniform, and may be relatively low- or monodisperse. Methods for the preparation of low- or monodisperse polymers are well known in the art, and include polymerisation reactions based on radical initiated polymerisation, including RAFT (reversible addition-fragmentation chain transfer) polymerisation (see, for example, Chiefari et al. *Macromolecules* 1998, 31, 5559).

In one embodiment, a polymer is hydrophilic.

In one embodiment, a polymer is water soluble.

In one embodiment, a polymer has a solubility of at least 0.5 mg/mL, at least 1 mg/mL, at least 5 mg/mL or at least 10 mg/mL, at least 20 mg/mL, at least 50 mg/mL or at least 100 mg/mL.

Many polymers are known in the art and may be used to produce network material as described herein. The choice of polymer will depend on the particular application of the network. Suitable polymeric molecules include natural polymers, such as proteins, oligopeptides, nucleic acids, glycosaminoglycans or polysaccharides (including cellulose and related forms such as guar, chitosan chitosan, agarose, and alginate and their functionalised derivatives), or synthetic polymers, such as polyethylene glycol (PEG), cis-1, 4-polyisoprene (PI), poly(meth)acrylate, polystyrene, polyacrylamide, and polyvinyl alcohol. The polymer may be a homopolymer. Alternatively, the polymer may be a copolymer where the different monomeric units are arranged randomly, alternatively, in blocks or in another arrangement.

The polymeric molecule may comprise two or more natural and/or synthetic polymers. These polymers may be arranged in a linear architecture, cyclic architecture, comb or graft architecture, (hyper)branched architecture or star architecture.

In one embodiment, the polymer is a biopolymer.

Suitable polymeric molecules include those polymeric molecules having hydrophilic characteristics. Thus, a part of the polymer, which part may refer to, amongst others, a monomer unit, the backbone itself, a side chain or a grafted polymer, is hydrophilic. In one embodiment, the polymeric molecule is capable of forming hydrogen bonds in a polar solvent, such as water. The polymeric molecule is soluble in water to form a continuous phase.

Some of the example polymers given above may be provided with suitable functionality in order to provide hydrophilic characteristics to that polymer. Some of the present inventors have previously described the use of functionalised polystyrene and a polystyrene copolymer in the preparation of a hydrogel material (see Appel et al. *J. Am. Chem. Soc.* 2010, 132, 14251-14260). The polystyrene copolymer is a copolymer with acrylamide, which includes hydroxyl functionality.

In one embodiment, a polymer is provided with a plurality of monomer units having a functionality selected from hydroxyl, amino, amido, carboxy, and sulfonate, including the salt forms thereof. The amino group may be a tertiary or quaternary amino group. The amide group may be a tertiary amide.

In one embodiment, a polymer is a polymer having a plurality of hydroxyl-containing monomer units. A hydroxyl-containing monomer unit may have one or more hydroxyl groups, such as one, two or three hydroxyl groups.

In one embodiment, a polymer is a polymer having a plurality of alkyl ether-containing monomer units.

A monomer unit may have both hydroxyl groups and of alkyl ether groups present. Additionally or alternatively, a polymer may comprise monomer units having hydroxyl groups, monomer units having alkyl ether groups and/or units having both hydroxyl groups and alkyl ether groups.

The alkyl ether may be a $C_{1-6}$ alkyl ether.

In one embodiment, substantially all of the monomer units in the polymer have a hydroxyl group or an alkyl ether group.

In one embodiment, the mole fraction of hydroxyl- or alkyl ether-containing monomer units in a polymer is at least 0.50, is at least 0.60, is at least 0.70, is at least 0.80, is at least 0.90, or is at least 0.95. The mole fraction refers to the number of monomer units having hydroxyl or ether functionality as a fraction of the total number of monomer units in the polymer. The mole fraction may be obtained using standard analytical techniques, for example NMR spectroscopy.

In one embodiment, one polymer in the network is a polymeric polyol.

In one embodiment, one polymer has a hydroxyl functionality present in each monomer unit.

In one embodiment, where there are two or more polymers in the network, each polymer is a polymeric polyol. In contrast the networks described in earlier work by the present inventors include only one hydroxyl-containing polymer, and most often no hydroxyl-containing polymer.

In one embodiment, a polymer comprises a plurality of vinyl alcohol-derived monomer units.

In one embodiment, a polymer is or comprises a poly(vinyl alcohol) (PVA). In this embodiment, the guest molecules may be covalently linked to the polymer backbone via the hydroxy functionality. PVA is readily available from commercial sources, at a variety of different average molecular weights. The PVA may be functionalised as appropriate to include suitable guest functionality.

In one embodiment, one polymer in the network comprises a plurality of saccharide monomer units.

In one embodiment, a polymer is or comprises a polysaccharide. The polysaccharide may be cellulose or a related form such as alkylated cellulose, guar, chitosan, agarose, and alginate and their functionalised derivatives. In this embodiment, the guest molecules may be covalently linked to the polymer backbone via the hydroxy functionality of the polymer, typically the ring hydroxy functionality.

In one embodiment, the polysaccharide is a cellulose or a functionalised derivative.

In one embodiment, the polysaccharide is hydroxyethyl cellulose.

In one embodiment, in addition or as an alternative to the polysaccharides described above, the polysaccharide is carboxymethyl cellulose or hyaluronic acid.

In one embodiment, the network comprises first and second polymers, wherein the first polymer is a poly(vinyl alcohol) and the second polymer is a polysaccharide.

In one embodiment, the network comprises a first polymer only, and the first polymer is a polysaccharide, for example a cellulose, such as hydroxyethyl cellulose, carboxymethyl cellulose or hyaluronic acid.

The polymers in the network are functionalised with guest molecules that are suitable for interacting with cucurbituril. In some embodiments, a first polymer is provided with a plurality of first guests wherein the first guest is suitable for forming a ternary complex together with cucurbituril and a second guest of a second polymer molecule.

In other embodiment, a polymer is provided with a plurality of first and second guests, wherein the first guest is suitable for forming a ternary complex together with cucurbituril and a second guest of the same first polymer (cross link) or a second guest of another first polymer molecule. In this embodiment, the first and second guests may be the same or different.

A guest molecule is covalently connected to the polymer. The guest molecule may be connected directly to functionality present in the polymer, or the guest molecule may be connected indirectly via a linker to the functionality.

For example, hydroxyl, amino and carboxyl functionality present in a polymer may serve as attachment sites for the guest molecule or the linker The polymers for use in the present invention may be obtained from commercial sources, and these polymers may be suitably functionalised with guest molecules using standard organic chemistry techniques. In some embodiments, the polymer is a biopolymer, which may be sourced from renewable resources.

An example of the functionalisation of a polysaccharide and a polyvinyl alcohol is described herein. As examples of the polysaccharide there is shown the use of carboxymethyl cellulose and hyaluronic acid.

In other embodiments, a polymer having suitable cucurbituril guest functionality may be prepared directly from a polymerisable composition which comprises monomers having suitable guest functionality and unfunctionalised monomers. The amount of guest in the final product may be varied by appropriate changes in the monomer concentration and other reaction conditions, as will be apparent to one of skill in the art. The polymerisation conditions and polymerisations reagents may be selected so as to provide a desired molecular weight, polydispersity, solubility, and/or mechanical and physical parameters.

A polymer described herein may be additionally functionalised to provide useful properties to the polymer and the resulting hydrogel. For example, the polymer may comprise a detectable label to aid detection and analysis of the polymer in a hydrogel.

In one embodiment, the polymers having suitable cucurbituril guest functionality are non-toxic. Toxicity may be determined by exposure of a cell to an aqueous mixture, including a solution, of a functionalised polymer as described herein, and monitoring the cell viability over a period of time, for example 1, 2, 5, 10 or 30 days.

In one embodiment, a functionalised polymer, or a mixture of functionalised polymers, may be regarded as non-toxic if 60% or more, 70% or more, 80% or more, or 90% or more of the cell population is viable over the period of time for analysis.

The toxicity study may be repeated at different concentrations of the functionalised polymer in the aqueous mixture. For example, the total concentration of the polymer in the aqueous mixture may be 0.01 wt %, 0.02 wt %, 0.04 wt %, 0.1 wt %, 0.3 wt %, 0.5 wt %, 1.0 wt %, 2.0 wt % or 5 wt %.

The toxicity may be the cell viability as recorded at one of the concentrations mentioned above, over a specified time period, such as those mentioned above. In a toxicity test, all the polymers used in the hydrogel may be tested together in a combined test mixture. Thus, the concentration of the polymer referred to above may be the combined total concentration of the polymers in that test mixture.

Cucurbituril Guest

As noted above, the guest is a compound that is capable of forming a guest-host complex with a cucurbituril. The term complexation therefore refers to the establishment of the guest-host complex.

In some embodiments of the invention, the guest host complex is a ternary complex comprising the cucurbituril host and a first guest molecule and a second molecule. Typically such complexes are based around CB[8] and variants and derivatives thereof.

In principal, any compound having a suitable binding affinity may be used in the methods of the present invention. The compound used may be selected based on the size of the moieties that are thought to interact with the cavity of the cucurbituril. The size of these moieties may be sufficiently large to permit complexation only with larger cucurbituril forms.

Cucurbituril guest molecules are well known in the art. Examples of guest compounds for use include those described in WO 2009/071899, Jiao et al. (Jiao et al. *Org. Lett.* 2011, 13, 3044), Jiao et al. (Jiao et al. *J. Am. Chem. Soc.* 2010, 132, 15734), Rauwald et al. (Rauwald et al. *J. Phys. Chem.* 2010, 114, 8606) and WO 2011/077099.

The present inventors have investigated complexation of guest molecules when these molecules are attached to a polymer and when these molecules are unattached. The use of isothermal calorimeter has demonstrated that the attachment of a guest molecule to a polymer does not result in a reduction in the binding constant of the guest. Thus, there is no observable effect on binding from polymer steric hindrance.

In one embodiment of the invention, the cucurbituril is CB[8] and the guests are molecules suitable for forming a ternary complex with this host. In one embodiment, one guest is electron rich guest and one guest molecule is electron deficient.

A cucurbituril guest molecule may be derived from, or contain, a structure from the table below:

| Guest Molecules | |
|---|---|
| HO-naphthalene-OH | A1 |
| HO-naphthalene | A2 |
| phenylalanine structure | A3 |
| tyrosine structure | A4 |
| tryptophan structure | A5 |
| methyl-bipyridinium | B1 |
| bis-imidazoline naphthalene | A6 |
| HO-phenyl-CH2-piperazine-NH | A7 |
| H2N-stilbene-NH2 | A8 |
| naphthalene | A9 |
| methylenedioxyphenol | A10 |
| catechol | A11 |
| tetrathiafulvalene | A12 |
| dimethyl-diazapyrene (B2) | B2 |
| dimethyl-diazaanthracene (B3) | B3 |
| methyl viologen stilbene | B4 |
| indole | A13 |
| serotonin (5-hydroxytryptamine) | A14 |
| anthracene | A15 |

-continued
Guest Molecules
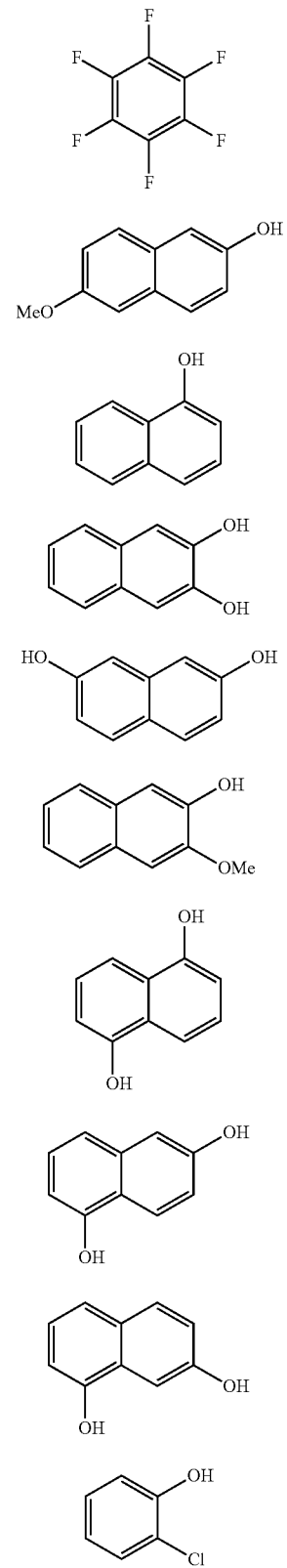
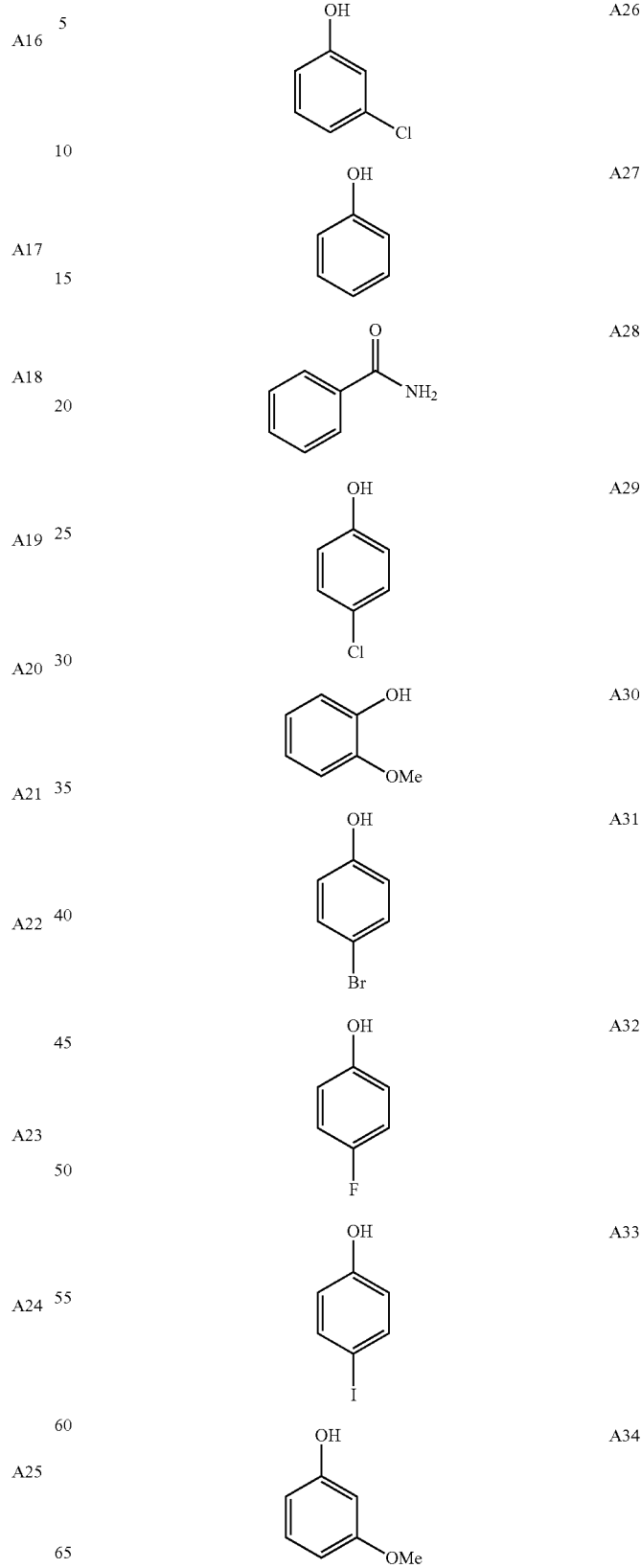

| Guest Molecules | |
|---|---|
| 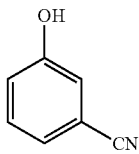 | A35 |
| 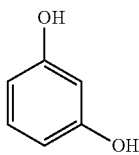 | A36 |
| 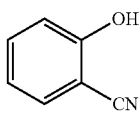 | A37 |
| 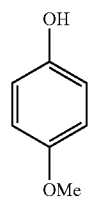 | A38 |
| 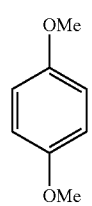 | A39 |
| 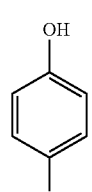 | A40 |
| 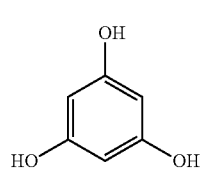 | A41 |
| 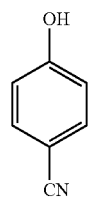 | A42 |
| 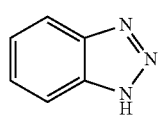 | A43 |

| Guest Molecules | |
|---|---|
| 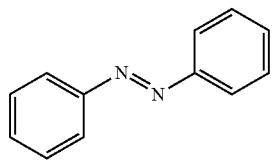 [SMILES: c1ccc(/N=N/c2ccccc2)cc1] | A44 |
| 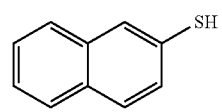 | A45 |
| 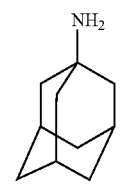 | A46 | where the structure may be a salt, including protonated forms, where appropriate. In one embodiment, the guest molecules are guest molecules for CB[8].

In one embodiment, the guest molecule is, or is derived from, or contains, structure A1-A43, A46 or B1-B4, in the table above.

In one embodiment, the guest molecule is, or is derived from, or contains, structure A1, A2, or A13 in the table above.

In one embodiment, the guest molecule is, or is derived from, or contains, structure B1.

In addition to, or as an alternative to, the guests in the table above, the following guest molecules may be selected:

| Guest Molecules | |
|---|---|
| 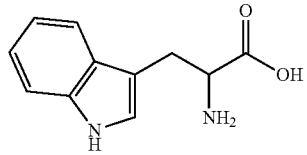 [SMILES: NC(Cc1c[nH]c2ccccc12)C(=O)O] | A47 |
| 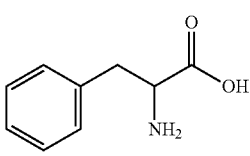 [SMILES: NC(Cc1ccccc1)C(=O)O] | A48 |

In one embodiment, the guest molecule is, or is derived from, or contains, structure A47 or A 48

Additionally, the guest molecule is or is derived from, or contains, adamantane, ferrocene or cyclooctane (including bicyclo[2.2.2]octane). Such are described by Moghaddam et al. (see *J. Am. Chem. Soc.* 2011, 133, 3570).

Other guest molecules suitable for use include pyrene, dibenzofuran and fluorine, and derivatives thereof. The derivative may be a compound where an aromatic ring atom is replaced with a heteroatom, such as nitrogen. Additionally or alternatively, the derivative may be a compound that is substituted with at a ring atom with a group such as halogen, alkyl, hydroxy, amino, alkoxy or the like.

In some embodiments, first and second guest molecules form a pair which may interact within the cavity of cucurbituril to form a stable ternary host-guest complex. Any guest pair that fits within the cavity of the cucurbituril may be employed. In some embodiments, the pair of guest molecules may form a charge transfer pair comprising an electron-rich and an electron-deficient compound. One of the first and second guest molecules acts as an electron acceptor and the other as an electron donor in the CT pair. For example, the first guest molecule may be an electron deficient molecule which acts an electron acceptor and the second guest molecule may be an electron rich molecule which acts as an electron donor or vice versa. In one embodiment, the cucurbituril is CB[8].

Suitable electron acceptors include 4,4'-bipyridinium derivatives, for example N,N'-dimethyldipyridyliumylethylene, and other related acceptors, such as those based on diazapyrenes and diazaphenanthrenes. Viologen compounds including alkyl viologens are particularly suitable for use in the present invention. Examples of alkyl viologen compounds include N,N-dimethyl-4,4-bipyridinium salts (also known as Paraquat).

Suitable electron donors include electron-rich aromatic molecules, for example 1,2-dihydroxybenzene, 1,3-dihydroxybenzene, 1,4-dihydroxybenzene, tetrathiafulvalene, naphthalenes such as 2,6-dihydroxynaphthalene and 2-naphthol, indoles and sesamol (3,4-methylenedioxyphenol). Polycyclic aromatic compounds in general may find use as suitable electron donors in the present invention. Examples of such compounds include anthracene and naphthacene.

In one embodiment, the guest is anthracene. In one embodiment, the guest is cinnamic acid.

Amino acids, such as tryptophan, tyrosine and phenylalanine may be suitable for use as electron donors. Peptide sequences comprising these amino acids at their terminus may be used. For example, a donor comprising an amino acid sequence N-WGG-C, N-GGW-C or N-GWG-C may be used.

In one embodiment, the guest is tryptophan or phenylalanine. In one embodiment the guest is phenylalanine.

In some embodiments, the guest molecules are a pair of compounds, for example first and second guest molecules, where one of the pair is an A compound as set out in the table above (e.g. A1, A2, A3 etc.), and the other of the pair is a B compound as set out in the table above (e.g. B1, B2, B3 etc.). In one embodiment, the A compound is selected from A1-A43 and A46. In one embodiment, the B compound is B1.

Other suitable guest molecules include peptides such as WGG (Bush, M. E. et al *J. Am. Chem. Soc.* 2005, 127, 14511-14517).

An electron-rich guest molecule may be paired up with any electron-deficient CB[8] guest molecule. Examples of suitable pairs of guest molecules for example first and second guest molecules, for use as described herein may include:
viologen and naphthol;
viologen and dihydroxybenzene;
viologen and tetrathiafulvalene;
viologen and indole;
methylviologen and naphthol;
methylviologen and dihydroxybenzene;
methylviologen and tetrathiafulvalene;
methylviologen and indole;
N,N'-dimethyldipyridyliumylethylene and naphthol;
N,N'-dimethyldipyridyliumylethylene and dihydroxybenzene;
N,N'-dimethyldipyridyliumylethylene and tetrathiafulvalene;
N,N'-dimethyldipyridyliumylethylene and indole;
2,7-dimethyldiazapyrenium and naphthol;
2,7-dimethyldiazapyrenium and dihydroxybenzene;
2,7-dimethyldiazapyrenium and tetrathiafulvalene; and
2,7-dimethyldiazapyrenium and indole.

In particular, suitable pairs of guest molecules for use as described herein may include 2-naphthol and methyl viologen, 2,6-dihydroxynaphthalene and methyl viologen and tetrathiafulvalene and methyl viologen.

In one embodiment, the guest pair is 2-naphthol and methyl viologen.

In one embodiment, the guest pair is a reference to a pair of guest molecules suitable for forming a ternary complex with CB[8].

In one embodiment, the guest molecule is preferably an ionic liquid. Typically, such guests are suitable for forming a complex with CB[7]. However, they may also form complexes with CB[8] in either a binary complex, or in a ternary complex together with another small guest molecule or solvent (see Jiao et al. *Org. Lett.* 2011, 13, 3044).

The ionic liquid typically comprises a cationic organic nitrogen heterocycle, which may be an aromatic nitrogen heterocycle (a heteroaryl) or a non-aromatic nitrogen heterocycle. The ionic liquid also typically comprises a counter-anion to the cationic organic nitrogen heterocycle. The nitrogen heteroaryl group is preferably a nitrogen $C_{5-10}$ heteroaryl group, most preferably a nitrogen $C_{5-6}$ heteroaryl group, where the subscript refers to the total number of atoms in the ring or rings, including carbon and nitrogen atoms. The non-aromatic nitrogen heterocycle is preferably a nitrogen $C_{5-6}$ heterocycle, where the subscript refers to the total number of atoms in the ring or rings, including carbon and nitrogen atoms. A nitrogen atom in the ring of the nitrogen heterocycle is quaternised.

The counter-anion may be a halide, preferably a bromide. Other counter-anions suitable for use are those that result in a complex that is soluble in water.

The guest is preferably a compound, including a salt, comprising one of the following groups selected from the list consisting of: imidazolium moiety; pyridinium moiety; quinolinium moiety; pyrimidinium moiety; pyrrolium moiety; and quaternary pyrrolidine moiety.

Preferably, the guest comprises an imidazolium moiety. An especially preferred guest is 1-alkyl-3-alkylimidazolium, where the alkyl groups are optionally substituted.

1-Alkyl-3-alkylimidazolium compounds, where the alkyl groups are unsubstituted, are especially suitable for forming a complex with CB[7].

1-Alkyl-3-alkylimidazolium compounds, where the alkyl groups are unsubstituted, are especially suitable for forming a complex with CB[6]

1-Alkyl-3-alkylimidazolium compounds, where an alkyl group is substituted with aryl (preferably napthyl), are especially suitable for forming a complex with CB[8].

The 1-alkyl and 3-alkyl substituents may the same or different. Preferably, they are different.

In one embodiment, the 3-alkyl substituent is methyl, and is preferably unsubstituted.

In one embodiment, the 1-alkyl substituent is ethyl or butyl, and each is preferably unsubstituted.

In one embodiment, the optional substituent is aryl, preferably $C_{5-10}$ aryl. Aryl includes carboaryl and heteroaryl. Aryl groups include phenyl, napthyl and quinolinyl.

In one embodiment, the alkyl groups described herein are linear alkyl groups.

Each alkyl group is independently a $C_{1-6}$ alkyl group, preferably a $C_{1-4}$ alkyl group.

The aryl substituent may itself be another 1-alkyl-3-substituted-imidazolium moiety (where the alkyl group is attached to the 3-position of the ring).

In another embodiment, the compound preferably comprises a pyridinium moiety.

The ionic liquid molecules describe above are particular useful for forming binary guest-host complexes. Complexes comprising two ionic liquid molecules as guests within a cucurbituril host are also encompassed by the present invention.

A cucurbituril may be capable of forming both binary and ternary complexes. For example, it has been previously noted that CB[6] compounds form ternary complexes with short chain 1-alkyl-3-methylimidazolium guest molecules, whilst longer chain 1-alkyl-3-methylimidazolium guest molecules form binary complexes with the cucurbituril host.

Preferred guests for use in the present invention are of the form $H^+X^-$, where $H^+$ is one of the following cations,

| Cation | Structure |
|---|---|
| A | 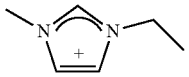 |
| B | 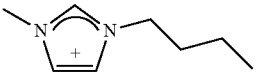 |
| C | 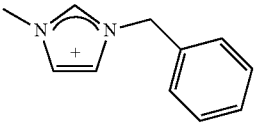 |
| D | 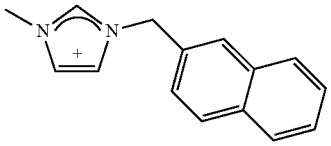 [SMILES: CN1C=CN(Cc2ccc3ccccc3c2)C1] |
| E | 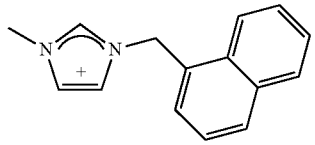 [SMILES: CN1C=CN(Cc2cccc3ccccc23)C1] |
| F | 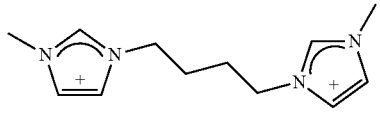 |
| G | 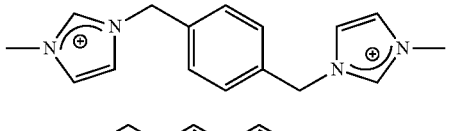 |
| H | 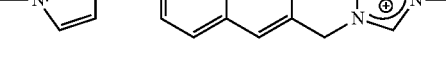 |

-continued

| Cation | Structure |
|---|---|
| I | 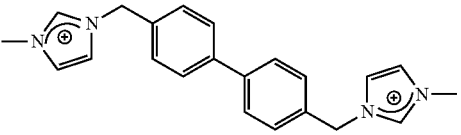 | and $X^-$ is a suitable counter-anion, as defined above. A preferred counter anion is a halide anion, preferably $Br^-$.

In a preferred embodiment, cation A or cation B may be used to form a complex with CB[7] or CB[6].

In a preferred embodiment, cation D or cation E may be used to form a complex with CB[8].

Cations A and B may be referred to as 1-ethyl-3-methylimidazolium and 1-butyl-3-methylimidazolium respectively.

Cations D and E may be referred to as 1-naphthalenylmethyl-3-methylimidazolium, where D is 1-naphthalen-2-ylmethyl-3-methylimidazolium and E is 1-naphthalen-1-ylmethyl-3-methylimidazolium.

Alternatively or additionally, the guest compounds may be an imidazolium salt of formula (I):

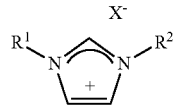

wherein $X^-$ is a counter anion;

$R^1$ is independently selected from H and saturated $C_{1-6}$ alkyl;

$R^2$ is independently $C_{1-10}$ alkyl which may optionally contain one or more double or triple bonds, and may be optionally interrupted by a heteroatom selected from —O—, —S—, —NH—, and —B—, and may be optionally substituted.

In one embodiment, $X^-$ is independently selected from the group consisting of $Cl^-$, $Br^-$, $I^-$, $BF_4^-$, $PF_6^-$, $OH^-$, $SH^-$, $HSO_4^-$, $HCO_3^-$, $NTf_2$, $C_2N_5O_4$, $AlCl_4^-$, $Fe_3Cl_{12}$, $NO_3^-$, $NMeS_2^-$, $MeSO_3^-$, $SbF_6^-$, $PrCB_{11}H_{11}^-$, $AuCl_4^-$, $HF_2^-$, $NO_2^-$, $Ag(CN)_2^-$, and $NiCl_4^-$. In one embodiment, $X^-$ is selected from $Cl^-$, $Br^-$, and $I^-$.

In one embodiment, $R^1$ is selected from H and linear saturated $C_{1-6}$ alkyl.

In one embodiment, $R^2$ is linear $C_{1-10}$ alkyl, which may optionally contain one or more double bonds, and may be optionally interrupted by a heteroatom selected from —O—, —S—, —NH—, and —B—, and may be optionally substituted.

In one embodiment, $R^2$ is linear $C_{1-10}$ alkyl, which may optionally contain one or more double bonds, and may be optionally substituted.

In one embodiment, where a double or triple bond is present, it may be conjugated to the imidazolium moiety. Alternatively, the double or triple bond may not be conjugated to the imidazolium moiety.

In one embodiment, the optional substituents are independently selected from the group consisting of halo, optionally substituted $C_{5-20}$ aryl, —$OR^3$, —$OCOR^3$, =O, —$SR^3$, =S, —$BR^3$, —$NR^3R^4$, —$NR^3COR^3$, —$N(R^3)CONR^3R^4$, —$COOR^3$, —$C(O)R^3$, —$C(=O)SR^3$, —$CONR^3R^4$, —$C(S)R^3$, —$C(=S)SR^3$, and —$C(=S)NR^3R^4$, where each of $R^3$ and $R^4$ is independently selected from H and optionally substituted saturated $C_{1-6}$ alkyl, $C_{5-20}$ aryl and $C_{1-6}$ alkylene-$C_{5-20}$ aryl.

or $R^3$ and $R^4$ may together may form an optionally saturated 5-, 6- or 7-membered heterocyclic ring which is optionally substituted with a group —$R^3$.

In one embodiment, the optional substituents are independently selected from the group consisting of halo, optionally substituted $C_{5-20}$ aryl, —$OR^3$, —$OCOR^3$, —$NR^3R^4$, —$NR^3COR^3$, —$N(R^3)CONR^3R^4$, —$COOR^3$, —$C(O)R^3$, and —$CONR^3R^4$, where $R^3$ and $R^4$ are defined as above.

Each $C_{5-20}$ aryl group may be independently selected from a $C_{6-20}$ carboaryl group or a $C_{5-20}$ heteroaryl group.

Examples of $C_{6-20}$ carboaryl groups include phenyl and napthyl.

Examples of $C_{5-20}$ heteroaryl groups include pyrrole (azole) ($C_5$), pyridine (azine) ($C_6$), furan (oxole) ($C_5$), thiophene (thiole) ($C_5$), oxazole ($C_5$), thiazole ($C_5$), imidazole (1,3-diazole) ($C_5$), pyrazole (1,2-diazole) ($C_5$), pyridazine (1,2-diazine) ($C_6$), and pyrimidine (1,3-diazine) ($C_6$) (e.g., cytosine, thymine, uracil).

Each $C_{5-20}$ aryl is preferably selected from optionally substituted phenyl, napthyl and imidazolium.

Each $C_{5-20}$ aryl group is optionally substituted. The optional substituents are independently selected from halo, $C_{1-6}$ alkyl, —$OR^3$, —$OCOR^3$, —$NR^3R^4$, —$NR^3COR^3$, —$N(R^3)CONR^3R^4$, —$COOR^3$, —$C(O)R^3$, and —$CONR^3R^4$, where $R^3$ and $R^4$ are defined as above.

In one embodiment, each $C_{5-20}$ aryl group is optionally substituted with $C_{1-6}$ alkyl.

Where the $C_{5-20}$ aryl group is an imidazolium, such is preferably substituted at nitrogen with a group $R^1$ (thereby forming a quaternary nitrogen).

The compound of formula (I) comprises an imidazolium moiety having a substituent $R^2$ at the 1-position and a substituent $R^1$ at the 3-position. In a further aspect of the invention, the compound of formula (I) may be optionally further substituted at the 2-, 4- or 5-positon with a group $R^4$, wherein $R^4$ has the same meaning as $R^1$.

The embodiments above are combinable in any combination, as appropriate.

Alternative Hosts and Guests

The hydrogels described herein may also be prepared using alternative host compounds. Thus cucurbituril may be replaced with a host that is capable of forming ternary or binary complexes such as described above. Alternatively, the hosts described below may be used in addition to a cucurbituril host in the hydrogels described herein.

In some embodiments, a host is selected from cyclodextrin, calix[n]arene, and crown ether, and the one or more building blocks have suitable host guest functionality for the cyclodextrin, calix[n]arene, or crown ether respectively.

In one embodiment, the host is cyclodextrin and the one or more building blocks have suitable cyclodextrin guest functionality.

The host may form a binary complex with a guest. In such cases, the host will be covalently linked to one or more other guest molecules to allow the formation of crosslinks between building blocks.

In one embodiment, a host is cyclodextrin. Cyclodextrin compounds are readily available from commercial sources. Many guest compounds for use with cyclodextrin are also known.

Cyclodextrin is a non-symmetric barrel shaped cyclic oligomers of D-glucopyranose. Typically, the cyclodextrin is capable of hosting hydrophobic uncharged guests. For example, guests include those molecules having hydrocarbon and aromatic functionalities such as adamantane, azobenzene, and stilbene derivatives. Other guest molecules for cyclodextrin include biomolecules such as xylose, tryptophan, estriol, esterone and estradiol.

In one embodiment, the cyclodextrin is an α-, β- or γ-cyclodextrin. In one embodiment, the cyclodextrin is a β- or γ-cyclodextrin. Typically larger guests are used together with a γ-cyclodextrin.

The cyclodextrin has a toroid geometry, with the secondary hydroxyl groups of the D-glucopyranose located at the larger opening, and the primary hydroxyl groups at the smaller opening. One or more of the hydroxy groups, which may be the secondary or the primary hydroxy groups, may be functionalised. Typically, the primary hydroxyl groups are functionalised. In one embodiment, references to a cyclodextrin compound are references to derivatives thereof. For example, one or two primary hydroxyl groups of the cyclodextrin is functionalised with a alkylamine-containing subsistent. In another example one, two or three of the hydroxyl groups within each D-glucopyranose unit is replaced with an alkyl ether group, for example a methoxy group. A plurality of covalently linked cyclodextrins may be connected via the hydroxyl groups.

Examples of unfunctionalised and functionalised cyclodextrins are set out in Chart 1 of Rekharsky et al. (*Chem. Rev.* 1998, 98, 1875), and examples of compounds for use as guests are set out over Tables 1 to 3 and Chart 2. Rekharsky et al. is incorporated by reference herein.

In the methods of preparation, the cyclodextrin may be present in the second phase, for example in an aqueous phase, as described herein.

In one embodiment, the host is calix[n]arene. Calix[n]arenes compounds are readily available from commercial sources, or may be prepared by condensation of phenol, resorcinol and pyrogallol aldehydes, for example formaldehyde.

Many guest compounds for use with calix[n]arenes are known. Typically, the calix[n]arene is capable of hosting amino-containing molecules. Piperidine-based compounds and amino-functionalised cyclohexyl compounds may find use as guests. Further examples of guests include atropine, crytand, phenol blue, and anthrol blue amongst others.

Examples of unfunctionalised and functionalised cyclodextrins are set out in Chart 1 of Danil de Namor et al. (*Chem. Rev.* 1998, 98, 2495-2525), which is incorporated by reference herein. Examples of compounds for use as guests are set out over Tables 2, 3, 5 and 10 of Danil de Namor et al.

In one embodiment, the calix[n]arene is a calix[4]arene, calix[5]arene or calix[6]arene. In one embodiment, the calix[n]arene is a calix[4]arene.

Suitably functionalised calix[n]arenes may be prepared through use of appropriately functionalised hydroxy aryl aldehydes. For example, the hydroxyl group may be replaced with an alkyl ether-containing group or an ethylene glycol-containing group. A plurality of covalently linked calix[n]arenes may be connected via the hydroxyl groups.

In the methods of preparation, the calix[n]arene may be present in the second phase, for example in an aqueous phase or a water immiscible phase, as described herein.

In one embodiment, the host is a crown ether. Crown ether compounds are readily available from commercial sources or may be readily prepared.

Many guest compounds for use with crown ether are also known. For example, cationic guests such as amino- and pyridinium-functionalized molecules may be suitable guest molecules.

Examples of unfunctionalised and functionalised cyclodextrins are set out throughout Gokel et al. (*Chem. Rev.* 2004, 104, 2723-2750), which is incorporated by reference herein. Examples of compounds for use as guests are described throughout the text.

In one embodiment, the crown ether is selected from the groups consisting of 18-crown-6, dibenzo-18-crown-6, diaza-18-crown-6 and 21-crown-7. In the present invention, larger crown ethers are preferred. Smaller crown ethers may have be capable of binding small metal ions only. Larger crown ethers are capable of binding functional groups and molecules.

In some embodiments, the host is a guest having crown ether and calix[n]arene functionality. Such hosts are referred to as calix[n]crowns.

In the methods of preparation, the crown ether may be present in the second phase, for example in a water immiscible phase, as described herein.

Other guest-host relationships may be used as will be apparent to a person of skill in the art. Other guest-host complexes for use in the present invention include those highlighted by Dsouza et al. (*Chem. Rev.* 2011, 111, 7941-7980) which is incorporated by reference herein, and in particular those hosts set out in Schemes 6 and 7, which includes cucurbituril, cyldoextrin, and calixerane as well as cyclophane AVCyc, calixpyridine C4P and squarimide SQAM.

The use of cyclodextrin is preferred over crown ether and calix[n]arene hosts.

Component

The hydrogel of the invention may be used to hold a component. In one aspect of the invention there is provided a hydrogel comprising a component. The hydrogel is suitable for storing a component, and this component may be later released as required at a chosen location.

In one aspect there is provided a hydrogel having a supramolecular cross-linked network obtainable from the complexation of an aqueous composition comprising cucurbituril and one or more polymers having suitable cucurbituril guest functionality, wherein the hydrogel holding a component. One polymer of the aqueous composition may have a molecular weight of 50 kDa or more.

It is understood that a reference to a component held by the hydrogel is not a reference to a solvent molecule. For example, the component is not water or an organic solvent. The component is therefore provided in addition to solvent that may be present within the hydrogel.

It is also understood that a reference to a component is not a reference to a cucurbituril or a polymer used in the preparation of the hydrogel, or an intermediary product formed from the complexation of cucurbituril with a suitably functionalised polymer. Otherwise, the component is not particularly limited.

In one embodiment, the encapsulated component has a molecular weight of at least 100, at least 200, at least 300, at least 1,000, at least 5,000 (1k), at least 10,000 (10k), at least 15,000 (15k), at least 20,000 (20k), at least 50,000 (50k), at least 100,000 (100k) or at least 200,000 (200k).

The present inventors have found that the hydrogels of the invention may usefully hold and deliver a component, such as a bioactive component, to a location. The activity of the component may be maintained throughout its incorporation into a hydrogel, throughout its storage in the hydrogel and after its subsequent delivery to the desired location.

In one embodiment, the component is a therapeutic compound.

In one embodiment, the component is or comprises a biological molecule, such as a polynucleotide (for example, DNA and RNA), a polypeptide or a polysaccharide.

In one embodiment, the component is a polymeric molecule, including biological polymers such as those biological molecules mentioned above.

In one embodiment, the component is a cell.

In one embodiment, the component has a detectable label. The detectable label may be used to quantify and/or locate the component. The label may be used to determine the amount of component contained with the hydrogel.

In one embodiment, the detectable label is a luminescent label. In one embodiment, the detectable label is a fluorescent label or a phosphorescent label.

In one embodiment, the detectable label is a visible label.

In one embodiment, the fluorescent label is a rhodamine or fluorescein label.

In one embodiment, the component is a polypeptide, such as a protein. The protein may be a serum albumin or a lysozyme. Examples of the former include bovine serum albumin.

In one embodiment, the component is a particle. The particle may be a metal particle.

In one embodiment, the component is selected from the group consisting of toxic molecules (such as nerve agents and heavy metals), hormones, herbicides, pesticides, antibodies, pathogens (such as viruses), adjuvants, gels, nanoparticles (including metal or non-metal particles), polymers (including synthetic and natural polymers), catalysts (organic, inorganic, and organometallic), adhesives and sealants.

The presence of a component within the hydrogel may be determined using suitable analytical techniques which are capable of distinguishing the network material and the component. Such techniques are well known to those of skill in the art.

Methods for the Preparation of Hydrogels

The polymers for use in the invention are functionalised with one or more guest molecules for forming a non-covalent interaction with a cucurbituril. The hydrogels of the present invention are simple and quick to prepare. The components of the hydrogel, one or more suitably functionalised polymers and a cucurbituril, may be mixed together, at appropriate concentrations, in water. Typically the supramolecular network and thus the hydrogel forms within seconds.

In one aspect of the invention there is provided a method of preparing a hydrogel, the method comprising the step of combining in an aqueous mixture a cucurbituril, a first polymer having a plurality of first guest molecules, and a second polymer having a plurality of second guest molecules, thereby to generate a hydrogel.

In one embodiment, the hydrogel is prepared from the complexation of (a) an aqueous composition comprising cucurbituril and (1) or (2); or (b) a composition comprising a plurality of covalently linked cucurbiturils and (1), (2) or (3). Each of (1), (2) and (3) is discussed above in the Hydrogel section.

The composition is prepared by combining in an aqueous mixture the cucurbituril and (1) or (2), or by combining in an aqueous mixture the plurality of covalently linked cucurbiturils and (1), (2) or (3).

The relative amounts of cucurbituril or plurality of covalently linked cucurbiturils to (1), (2) or (3) may be appropriately selected to yield a hydrogel having desired relative amounts of these components. The relative amounts of components used in the mixture prior to complexation will result in a hydrogel having the same relative amounts of components, as all components of the mixture are incorporated into the hydrogel. The amounts of water, cucurbituril and polymer present are described above in the Hydrogel section.

In the methods of the invention at least a cucurbituril and a suitably functionalised polymer are contacted only when the hydrogel is required to be prepared. The hydrogels of the present inventions form rapidly, typically in seconds under ambient conditions, when the complexable components are brought together in a complexable aqueous mixture. Thus, individual components of the complexable mixture may be stored separately, optionally as an aqueous mixture, until required. When required, the components may be brought together in order to form the hydrogel.

In one embodiment, a hydrogel may be formed using the steps as described above, and the resulting hydrogel diluted with water, thereby to obtain a hydrogel having a higher water content (lower polymer content). Such a dilution step may be performed in order to, for example, fine tune the mechanical properties of the hydrogel. After addition of the water, the mixture may be agitated.

Formation of the hydrogel may be apparent to the visible eye, and simple tests, such as vial tests (whereby a vial containing material is simply upended) are useful indicators of hydrogel formation. To fully analyse the hydrogel, more rigorous analysis steps may be performed during the hydrogel formation and/or after hydrogel formation. Methods suitable for analysing hydrogels of the invention are described below.

Also described herein are hydrogels holding a component. The component may be introduced into a hydrogel either during hydrogel formation, or the component may be added to a preformed hydrogel, which is then disturbed such as to allow the incorporation of the component therein. In particular the rheological properties of the hydrogel may be analysed and are useful for characterisation.

Where the component is incorporated into the hydrogel during hydrogel formation, the component simply needs to be mixed with the hydrogel components prior to hydrogel formation. The supramolecular network forms around the component thereby to provide a hydrogel holding a component.

Thus in another aspect of the invention there is provided a method for preparing a hydrogel holding a component, the method comprising the step of bringing into contact in an aqueous solution a mixture of cucurbituril, a component, and one or more polymers having suitable cucurbituril guest functionality, thereby to component thereby to generate a hydrogel holding a component.

In one embodiment the method comprises the step of combining in an aqueous solution a cucurbituril, a first polymer having a plurality of first guest molecules, a second polymer having a plurality of second guest molecules, and a component thereby to generate a hydrogel holding a component.

Alternatively, a method for preparing a hydrogel holding a component comprises the steps of providing a hydrogel of the invention and agitating that hydrogel in the presence of a component, thereby to incorporate the component into the hydrogel. The agitation step may be a mechanical agitation or disruption of the hydrogel.

The complexes of the present invention are reversible, and a complex that is disrupted is capable of reforming.

Analysis of Hydrogels

The hydrogel material may be analysed using techniques familiar to those of skill in the art.

During a hydrogel formation process, the formation of a complex may be monitored by analysis of a colour change in the reaction mixture. The formation of a complex, such as a ternary complex, may be associated with the formation of charge transfer bands that are associated with a formed complex. For example, viologen and napthyl guests may together form a ternary complex with CB[8] in water. The formation of this complex is apparent from the resulting orange colour of the mixture, which is derives from the formation of charge transfer between the viologen and napthyl guests.

Described herein, for example, is scanning electron microscopy (SEM). Such is useful for analysing and measuring pore shape and size within the hydrogel. Typically a hydrogel sample for analysis by SEM is dried and lyophilised prior to such analysis. For hydrogels having a very high water content (for example, having a water content of or more 0.95 wt %), SEM techniques may not be appropriate, as the hydrogel is observed to disintegrate during sample preparation. For such hydrogels other analytical techniques may be more appropriate, such as the techniques described below.

Small angle neutron scattering (SANS) may also be used to analysis the microstructure of the hydrogel. Correlations lengths may be established from SANS measurements, as described in detail herein.

Standard rheological techniques may be employed to establish the storage modulus, the loss modulus, the complex viscosity, the elasticity and the tan δ of the hydrogel. For example, strain amplitude sweep and frequency sweep measurements may be taken as part of the dynamic oscillatory rheological characterisation of the hydrogels. Such techniques are as described in detail herein, and the rheological properties of the hydrogel are defined in detail in the Hydrogel section above.

The formation of a hydrogel material may also be clearly visible from the reaction mixture. The formation of a gel from an aqueous mixture may be apparent from an inverted vial test and the like.

Use of Hydrogel

The hydrogels described herein may find use as materials in medical applications, by virtue of their low toxicity and high water content. The hydrogels of the invention, when suitably loaded with a component, may be used to deliver that component to a target location.

The present inventors have established that components held in the hydrogel of the invention may be released from the hydrogel at a chosen location. Thus, there is provided a method of delivering a component to a location, the method comprising the steps of:

(i) providing a hydrogel holding a component, as described herein;
(ii) making the hydrogel available at a target location;
(iii) releasing the component from the hydrogel.

In one embodiment, the target location is a location in vivo. Thus, the hydrogel may be placed at a target location in or on a subject. The subject may be a mammal, such as a human or a rodent, such as a rat or a mouse.

In this embodiment, the component may be a therapeutic for use in the treatment or prophylaxis of a disease. The hydrogel comprising the therapeutic compound is therefore suitable for use in methods of treatment of a human or animal body.

In other embodiments, the hydrogel is suitable for delivering a component to a location that is ex vivo, or in vitro.

In one embodiment, the hydrogel is capable of releasing at least 50%, at least, 60%, at least 70%, at least 80%, at least 90%, or at least 95% of a held component over a set time period. This amount may be a mole or weight amount, depending on the techniques used to measure release.

In one embodiment, the hydrogel is capable of releasing substantially all of the held component over a set time period.

In one embodiment, the time period may be a period of at least 1 day, at least 2 days, at least 5 days, at least 20 days, at least 40 days, or at least 90 days. The time period may be a period of at most 100 days, at most 150 days, or at most 200 days.

In one embodiment, the time period is selected from a range where the maximum and minimum values are selected from the values above. For example, the time period may a value in the range 20 to 150 days.

The time period for release may begin from the time at which the hydrogel holding the component is prepared. Alternatively, the time period may begin from the time at which the hydrogel is made available at a target location. In a further embodiment, the time period may begin from the time at which the hydrogel network is disrupted, for example by exposure to a competitor guest, a reducing agent or another external stimulus.

As noted above, the hydrogels described herein are capable of holding a component within. This component may be released from the hydrogel as and when required. The present inventors have found that changes to a hydrogel composition may be used to change the timing of component release from a hydrogel. Here, timing may refer to the rate at which the component is released, and additionally the timing may refer to change in that rate over time.

The present inventors have found that the hydrogels of the invention permit release of the component over a period of hours, days, weeks or months. The inventors have found that material may be released at a substantially constant rate over that time period. This may be referred to as a sustained release of the component from the hydrogel.

Typically, a sustained release of the component is obtainable where the total amount of polymer present in the hydrogel is 1.0 wt % or more, 1.1 wt % or more, 1.2 wt % or more, or 1.5 wt % or more.

Typically, a sustained release of the component is obtainable where the component has a molecular weight of at least 20,000, or at least 50,000.

The inventors have established that the component may also be released with changes in the rate of release over time. In one embodiment, a proportion of the component my be released over a first time period at a first rate of release, followed by the release of the component over a second time period at a second rate of release. In on embodiment, the first rate of release is greater than the second rate of release. Where the first rate of release is higher, the release may be referred to as a burst release. The first and second time period may be periods of hours, days, weeks or months.

Typically, a burst release of the component is obtainable where the total amount of polymer present in the hydrogel is less than 1.0 wt %, 0.9 wt % or less, 0.7 wt % or less, or 0.5 wt % or less.

Typically, a sustained release of the component is obtainable where the component has a molecular weight of at most 15,000 or at most 10,000.

In one embodiment, a component is released without the application of any external stimulus to the hydrogel. Thus, a hydrogel may be placed at a desired location and the component is simply permitted to leach out of the hydrogel.

In other embodiments, the release of the component may be associated with the at least partial decomplexation of the network. This decomplexation may be initiated by the application of an external stimulus to the hydrogel. Examples of decomplexation techniques are described above in the Complex section, and include the use of competitor guest molecules to disrupt the network, and the oxidation or reduction of a guest molecule, for example using an oxidising or reducing agent as appropriate.

Covalent Links and Cross-Links

As described above, the network of the hydrogel includes polymers that are linked or cross-linked by non-covalent bonding. For example, a host such as CB[8] may be used as a "handcuff" to hold first and second guest molecules from the same or different polymers in a ternary complex.

As an alternative to, or in addition to, the non-covalent links, the polymers may be linked or cross-linked by covalent bonding. The presence of covalent bonds within a network may provide a hydrogel having greater strength over those networks that are formed from non-covalent interactions only. In one embodiment, the covalent bonds are formed between the guest molecules of the polymers.

The present inventors have found that the formation of covalent bonds between building blocks may be achieved via a guest-host intermediate. Thus, in a first step a supramolecular polymer may be formed where a ternary complex having a host non-covalently holds first and second guest molecules from the same or different polymers. The first and second guest molecules are permitted to react, thereby to form a covalent bond linking the polymers. A supramolecular polymer is a polymer where two polymers are held together by a non-covalent complex.

In preferred embodiments of the invention the host in the ternary complex has a cavity that is a through channel in the molecule. Thus, guest molecules may enter the cavity from one of a plurality of channel openings. For example, cucurbituril compounds such as CB[8] have two openings to a central cavity and each opening is accessible.

Hosts having such a through channel may accommodate two guests in a ternary complex in a head-to-tail or head-to-head arrangement. In the head-to-head arrangement the two guests have entered occupy the same opening. In the head-to-tail arrangement the two guests have entered different openings in the host.

In one embodiment, the guests are held in a head-to-tail arrangement within the cavity of the host. It follows that the formation of a covalent bond between the guests thereby traps the host on the conjoined polymers. The host may continue to non-covalently bond to the guest formed from the reaction of the first and second guests.

The polymers, such as the polymer first and second guests, react in response to an external stimulus, such as light, heat or change in pH. In one embodiment, the reaction is initiated by light irradiation, for example UV light irradiation.

The first and second guests may participate in a pericyclic reaction, thereby to form a covalent bond.

The first and second guest molecules may participate in a cycloaddition reaction, thereby to form a covalent bond. For example, the cycloaddition reaction may be a [4+4] or a [2+2] cycloaddition reaction.

In one aspect there is provided a method of covalently linking or cross-linking a polymer, the method comprising the steps of:
(i) providing a non-covalently linked polymer or polymers, wherein the non-covalent linked is formed from a ternary complex of a host holding first and second guest molecules provided on the polymer or polymers;
(ii) permitting the polymer or polymers to react, thereby to form a covalent bond linking the polymer or polymers.

Thus, in one aspect, there is provided a method of preparing a hydrogel having a supramolecular cross-linked network, wherein the hydrogel is formed from the covalent crosslinking of a polymer and/or the covalent linking of a polymer to another polymer, the method comprising the steps of:
(i) providing a hydrogel having a supramolecular cross-linked network which is obtainable from the ternary complexation of an aqueous composition comprising a host, such as cucurbituril, and one or more polymers having suitable guest functionality, such as cucurbituril guest functionality;
(ii) permitting the polymer or polymers to react, thereby to form a covalent bond linking the polymer or the polymers.

In one embodiment step (i) provides a hydrogel having a supramolecular cross-linked network obtainable from the complexation of an aqueous composition comprising cucurbituril and one or more polymers having suitable cucurbituril guest functionality, wherein one or each polymer has a molecular weight of 50 kDa or more.

In step (ii) it is not necessary for all the polymers, such as first and/or second polymers, to react. The product may retain some ternary complexes where the host holds first and second guest molecules.

In one embodiment, the first and second guest molecules are held in a head-to-tail arrangement in the cavity of the host.

In one embodiment, the first and second guest molecules are capable or participating in a cycloaddition reaction.

In one embodiment, the first and second guest molecules are the same.

In one embodiment, the hydrogel provided in (i) is obtainable from the ternary complexation of an aqueous composition comprising a host, such as cucurbituril, and one polymer, which has first and second guest molecules, which may be the same or different.

In one embodiment, each of the first and second guest molecules includes an anthracene compound. As shown herein, two anthracene-containing guest molecules held by a host in a ternary complex may undergo a cycloaddition reaction, thereby to form a covalent link between the guest molecules. The product formed from the reaction of the first and second guest molecules may be referred to as the addition product.

In one embodiment, each of the first and second guest molecules includes a cinnamic acid compound.

The addition product may become a guest that that is non-covalently held in a binary complex together with the host. Thus, the addition product may be retained within the cavity of the host.

It will be appreciated that the addition product and the host may separate (dissociate). This does not result in the loss of structural integrity to the network. The formation of the covalent bond between first and second guest molecules provides a link between polymers. The host is therefore no longer required to link together the polymers.

The dissociation and movement of the host from the addition product may in practice be limited. The formation of the addition product effectively contains the host on the cross-linked polymers, and its movement may be limited or prevented by structural and functional features of the addition product, or other features of the polymer.

The formation of a covalent bond between first and second guest molecules yields a single guest, and a resulting complex may be referred to as a binary complex.

It is not necessary for the covalently linked first and second guest molecules to have a high association constant. Once the covalent link is made there is no requirement for the host to non-covalently bind to the addition product: the covalent bond provides a structural link between polymers that will not dissociate, and the host is no longer required to maintain the integrity of the link between the polymers.

In one embodiment, the reaction is a light- or a heat-initiated reaction.

Light may refer to UV or visible light. Heat refers to a reaction temperature that is above the reaction temperature for the preparation of the supramolecular cross-linked network. Heat may refer to a reaction temperature above room temperature. Heat may refer to a reaction temperature of 50° C. or above, 60° C. or above, or 70° C. or above.

The network is formed from the covalent crosslinking of a polymer and/or the covalent linking of a polymer to another polymer thereby forming the network.

Other Preferences

Each and every compatible combination of the embodiments described above is explicitly disclosed herein, as if each and every combination was individually and explicitly recited.

Various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above.

Experimental and Results $^1$H NMR (400 MHz) spectra was recorded using a Bruker Avance QNP 400. Chemical shifts are recorded in ppm ($\delta$) in $D_2O$ with the internal reference set to $\delta$ 4.79 ppm. ATR FT-IR spectroscopy was performed using a Perkin-Elmer Spectrum 100 series FT-IR spectrometer equipped with a universal ATR sampling accessory. UV-VIS studies were performed on a Varian Cary 4000 UV-Vis spectrophotometer. Gel permeation chromatography (GPC) was carried out in water ($H_2O$) on a Shodex glucose column with a Shimadzu SPD-M20A prominence diode array detector, Optilab refractive index detector and dynamic light scattering detector (both Wyatt). Samples were filtered over 0.2 mm PVDF filters before injection using a 0.6 mL/min flow rate.

ITC titration experiments were carried out on a VP-ITC from Microcal Inc. at 25° C. in 10 mM sodium phosphate buffer (pH=7). In a typical experiment, the host was in the sample cell at a concentration of 0.1 mM, and the guest was in the syringe at a 10 fold higher concentration. In the case of functional polymers, the concentration used is determined from the concentration of functional monomer units in solution and not the concentration of polymer. A titration consisted of 29 consecutive injections of 2-10 mL with at least 300 s intervals between injections. The first data point was removed from the data set prior to curve fitting. Heats of dilution were checked by titration well beyond saturation or by titration of the guest into a buffer solution and subtracted from the normalized enthalpies, but relatively small in all cases. The data were analyzed with Origin 7.0 software, using the one set of sites model.

Rheological characterization was performed using an ARES-LC controlled strain rheometer fitted with a water bath set to 25° C. Strain sweep measurements (dynamic oscillatory strain amplitude) were performed at a frequency of 10 rad/s. Frequency sweep measurements were performed at a 5% strain amplitude. Temperature sweep was performed on a temperature ramp from 25 to 75° C. at a rate of 10° C./min and performed at 5% strain and 10 rad/s. All measurements were performed using a 25 mm parallel plate geometry set to a gap height of 0.75 mm and analysed using TA Instruments TA Orchestrator software.

Small-angle neutron scattering measurements were performed on D11 at the Institut Laue Langevin (ILL) (Grenoble, France). A wavelength ($\lambda$) of 10 Å and either two configurations were used to cover a q range from $4.4\times10^{-3}$ Å$^{-1}$ to $3.1\times10^{-1}$ Å$^{-1}$, where q is the modulus of the scattering vector. The samples were measured in 1 mm quartz cells using $D_2O$ as a solvent and the data were recorded in a thermostatically controlled rack at 25° C. The scattering from each sample was corrected for the electronic background, detector deadtime, scattering from the empty cell and sample transmission. The intensity was converted to the differential scattering cross-section in absolute units (cm$^{-1}$) using the scattering from a water sample. Data reduction was performed using the software Lamp, the Large Array Manipulation Program (http://www.ill.fr/data_treat/lamp/lamp.html; D. Richard, M. Ferrand and G. J. Kearley, J. Neutron Research 4, 33-39, 1996).

Scanning electron microscopy (SEM) images were obtained using a Leo 1530 variable pressure SEM using and InLens detector. SEM samples were prepared by direct freezing of the supramolecular hydrogels in liquid nitrogen followed by lyophilization. The resulting cryo-dried materials were imaged after sputtering. It was not possible to take SEM images of the cryo-dried samples with lower loading (<0.5 wt %) as the hydrogel structures did not survive the lyophilization process and collapsed on account of their high water content.

Hydroxyethylcellulose (HEC) was purchased from Aldrich and dried overnight in a vacuum oven at 105° C. Poly(vinylalcohol) (PVA, 98% hydrolyzed) was purchased from Aldrich, dissolved in water at 5 wt %, precipitated from a 1:1 solution of acetone and methanol and dried overnight at 60° C. MVNCO and cucurbit[8]uril were prepared according to a literature procedures (Biedermann et al. *Macromolecules* 2011, 44, 4828-4835; Kim et al. *J. Am. Chem. Soc.* 2000, 122, 540-541). All other materials were purchased from Aldrich and used as received.

General Synthetic Protocol

A cellulose-based scaffold, hydroxyethyl cellulose (HEC), was easily functionalized using commercially available 2-naphthyl isocyanate (Np) in a one-step reaction performed at ambient temperature in N-methylpyrrolidone using dibutyltin dilaurate (TDL) as a catalyst (as described above). A viologen unit containing a reactive isocyanate group, prepared according to a facile literature preparation (Biedermann et al. *Macromolecules* 2011, 44, 4828-4835), was conjugated to commercially available poly(vinyl alcohol) PVA) using similar conditions. These synthetic protocols are facile, rapid and are easily scaled.

Synthesis of HEC-Np

HEC (1.00 g) was dissolved in N-methylpyrrolidone (NMP, 150 mL) at 110° C. The solution was cooled to room temperature and Np—NCO (29.7 mg, 0.18 mmol) and dibutyltin dilaurate (3 drops) were added and the mixture allowed to stir at room temperature overnight. The functional polymer was then purified by precipitation from acetone, filtered, and dried overnight under vacuum at 60° C. (1.01 g, 98%). $^1$H-NMR Spectroscopy (MeOD, 500 MHz) d (ppm)=7.99-7.29 (7H, br, Np—H), 4.60-2.75 (455H, br, cellulose backbone). Elemental: Found C, 47.14; H, 6.93; N, 0.68. $C_{85.5}H_{144.2}O_{60.6}N_1$ required C, 47.63; H, 6.74; N, 0.65. FT-IR (ATR) n=3410 (br), 2950 (br), 2910 (br), 1395, 1075 (s) cm$^{-1}$. GPC ($H_2O$): $M_n$, (PDI)=3.4 MDa (1.25).

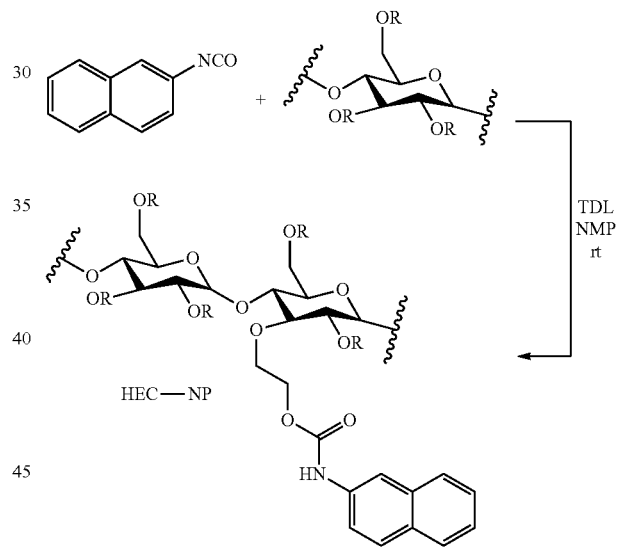

Synthesis of PVA-MV

PVA (1 g, $M_w$ of 195 kDa) was dissolved in N-methylpyrrolidone (NMP, 60 mL) and MV-NCO (0.63 g, 1.13 mmol) was added along with dibutyltin dilaurate (3 drops) and stirring overnight at room temperature. The functional polymer was then purified by precipitation from ethyl acetate, filtered, and dried overnight under vacuum at 60° C. (1.55 g, 95%). $^1$H-NMR Spectroscopy (D2O, 500 MHz) d (ppm)=9.18-8.88 (4H, br, MV aryl-H), 8.60-8.33 (4H, br, MV aryl-H), 4.51-4.45 (2H, br, MV-CH$_2$), 4.38 (3H, s, MV-CH$_3$), 4.20-4.05 (3H, br, MV-CH$_2$—CH$_2$—OCN— and —NCO—CH from the backbone), 3.21-3.08 (4H, br, —CH$_2$—NCO—), 1.95-1.32 (48H, br, polymer backbone and hexamethylene linker). Elemental: Found C, 49.77; H, 7.66; N, 3.24. $C_{61}H_{106}O_{23}N_4B_2F_8$ required C, 50.98; H, 7.43; N, 3.90. FT-IR (ATR) n=3320 (br), 2920 (br), 2900 (br), 1715, 1690, 1580, 1450, 1290, 1060 (s), 820 cm$^{-1}$. GPC ($H_2O$): $M_n$ (PDI)=1.5 MDa (1.26).

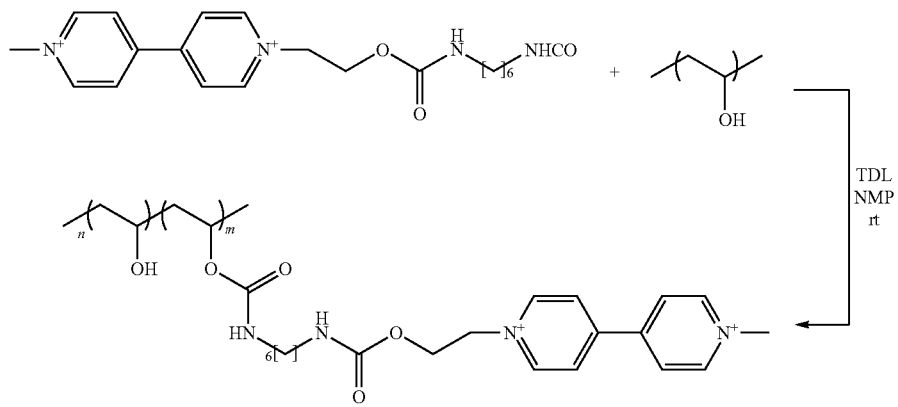

General Hydrogel Preparation

Hydrogels were prepared by first dissolving HEC-Np (5 mg) in water (0.5 mL) with stirring and mild heating. PVA-MV (0.1 mg) and CB[8] (0.1 mg) were then dissolved in water (0.5 mL) with some sonication (less than 5 min). The solutions were then mixed and shaken for approximately 1 s before hydrogel formation.

Figure 5:
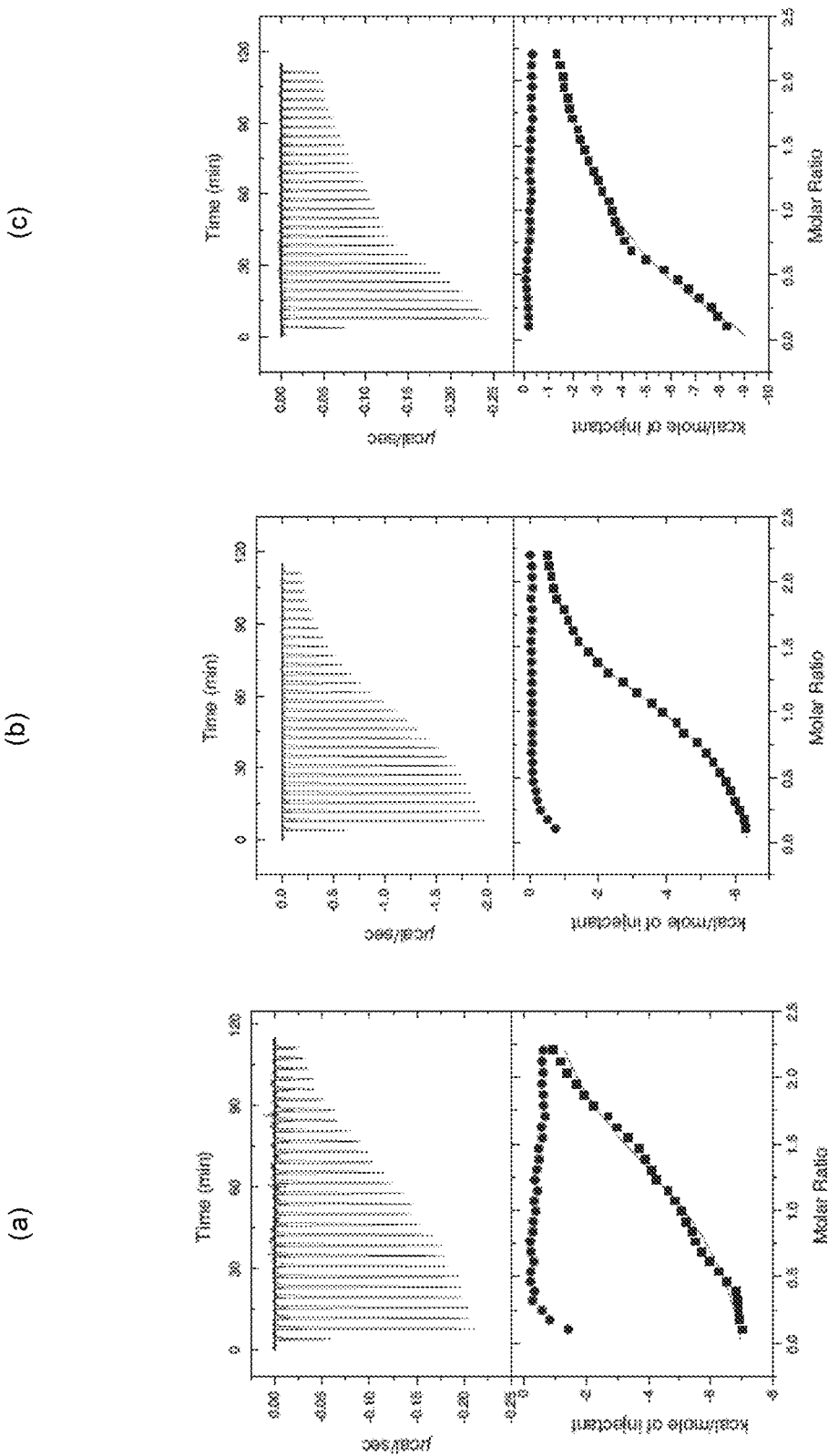
FIG. 5 shows the ITC data for (a) for binding of HEC-Np to PVA-MV with and without CB[8] present; (b) for binding of 2-naphthol (NpOH) to PVA-MV with and without CB[8] present; and (c) for binding of HEC-Np to M2V with and without CB[8] present.
Figure 6:
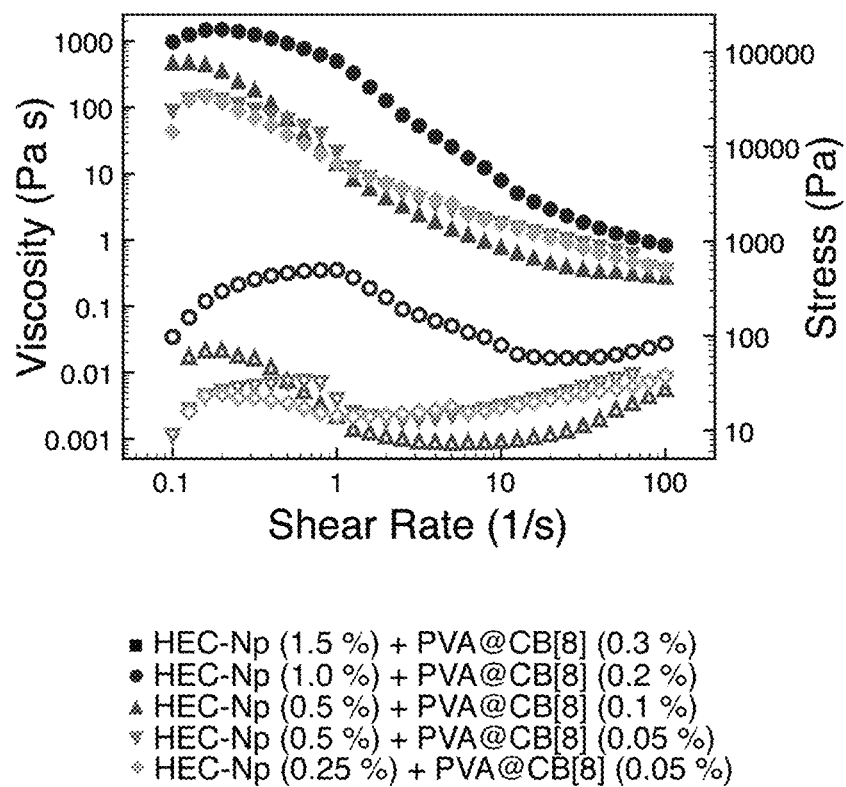
FIG. 6 shows the relationship between shear rate, viscosity and stress for prepared supramolecular hydrogels, where HEC-Np (1.5 wt %)/PVA-MV (0.3 wt %) (■), HEC-Np (1.0 wt %)/PVA-MV (0.2 wt %) (•), HEC-Np (0.5 wt %)/PVA-MV (0.1 wt %) (▲), HEC-Np (0.5 wt %)/PVA-MV (0.05%) (▼), and HEC-Np (0.25 wt %)/PVA-MV (0.05 wt %) (◆). The relative amount of CB[8] in each case was 1 equiv. relative to PVA-MV. The filled symbols represent viscosity values, and the unfilled versions of the symbols represent stress values.

Isothermal titration calorimetry (ITC) was used for quantitative investigation of the respective binding thermodynamics for the HEC-Np and PVA-MV with CB[8] (see Reczek et al. *J. Am. Chem. Soc.* 2009, 131, 2408-2415; Appel et al. *J. Am. Chem. Soc.* 2010, 132, 14251-14260; Biedermann et al. *Macromolecules* 2011, 44, 4828-4835; Heitmann et al. *J. Am. Chem. Soc.* 2006, 128, 12574-12581). Complete thermodynamic data for second-guest binding based on the concentration of functional units (i.e. not polymer concentration) is shown in FIG. 5. ITC measurements were carried out on PVA-MV with both a monovalent small molecule 2-naphthol and with HEC-Np in the presence of CB[8] in order to identify the effect on binding stemming from both steric hindrance and the explicit structure of the polymeric backbones. Likewise, measurements were carried out on HEC-Np with a monovalent small molecule viologen (M2V). No significant difference in binding constants was observed between polymeric entities and their corresponding small molecules, identifying that there is no observable effect on binding from steric hindrance.

three components of the ternary complex as only the system with Np, MV and CB[8] forms hydrogels. A lack of any one of the components, or the addition of CB[7] (whose cavity is only large enough to encapsulate MV alone) instead of CB[8] does not produce hydrogels.

Frequency dependent rheological characterization of a titration of PVA-MV@CB[8] into an aqueous solution of HEC-Np (0.5 wt %) is shown in FIG. 2 (top row, furthest right). Addition of only 0.05 wt % of PVA-MV@CB[8] is required for hydrogel formation and the relative loadings of HEC-Np to PVA-MV@CB[8] can produce materials with a large range of mechanical properties. Strain dependent oscillatory rheology (FIG. 2, top row, furthest left) displays an extremely broad linear viscoelastic region, indicating that these materials have a broad processing region. It is only at higher loading (1.5 wt %) that a deviation from linear viscoelasticity is observed as a breakdown of the hydrogel structure at strain amplitudes above 10% yield a large decrease in oscillatory shear moduli and complex viscosity.

The frequency dependence of the storage and loss oscillatory shear moduli (G' and G", respectively), clearly identifies hydrogel-like behaviour as the two are linear and parallel and G' is dominant across the whole range of frequencies observed (FIG. 2, top row, furthest right). In general, these hydrogels are soft (G'=0.5 kPa at 1.5 wt % loading of HEC-Np) and display linear 'shear-thinning' behaviour, yet the range of materials produced are highly

TABLE 1

Thermodynamic data for second guest binding of HEC-Np and PVA-MV

| Entry | MV | Np | $K_a$ $(M^{-1})^a$ | $\Delta G$ $(kcal/mol)^b$ | $\Delta H$ $(kcal/mol)^a$ | $-T\Delta S$ $(kcal/mol)^c$ |
|---|---|---|---|---|---|---|
| 1 | PVA-MV | HEC-Np | $(6.87 \pm 0.87) \times 10^5$ | $-33.3 \pm 0.1$ | $-7.6 \pm 0.2$ | $25.7 \pm 0.2$ |
| 2 | PVA-MV | NpOH | $(1.10 \pm 0.03) \times 10^5$ | $-28.8 \pm 0.1$ | $-6.8 \pm 0.2$ | $21.9 \pm 0.2$ |
| 3 | $M_2V$ | HEC-Np | $(1.07 \pm 0.16) \times 10^5$ | $-28.7 \pm 0.1$ | $-24.5 \pm 0.2$ | $4.2 \pm 0.2$ |

[a]Mean values measured from at least three ITC experiments at 25° C. in 10 mM PBS buffer at pH 7.0.
[b]Gibbs free energy values calculated from $K_a$ values.
[c]Entropic contributions to $\Delta G$ calculated from $K_a$ and $\Delta H$ values Simple mixing of a solution of HEC-Np (0.5 wt %) with a solution of PVA-MV (0.1 wt %) containing a 1:1 loading of MV:CB[8] (PVA-MV@CB[8]) instantaneously produced a lightly orange coloured, transparent hydrogel. The orange colour is inherent to the MV:Np:CB[8] ternary complex and is a product of the charge-transfer complex between the MV and Np moieties within the CB[8] cavity. There is a clear dependence of hydrogel formation on the presence of all elastic (tan δ=0.3). Highly elastic materials (tan δ=0.26) are obtained even at extremely high water content (99.7%). Moreover, the viscosity and mechanical properties can be tuned over two orders of magnitude (FIG. 2, top row, middle and right respectively). Temperature-dependent rheological behaviour was characterized up to 75° C. (FIG. 2, bottom row, left) and shows a decrease in material properties as some mechanical integrity is lost (Tan δ=0.26 to 0.4). The association constant of the ternary complex cross-links decreases with temperature, intuitively leading to a decrease in the bulk material properties.

Step rate measurements were performed in order to investigate the recovery of hydrogel material properties following deformation. A high magnitude shear rate ($\gamma=500$ s$^{-1}$) was applied to break down the hydrogel structure, followed by a low magnitude shear rate ($\gamma=0.05$ s$^{-1}$) to monitor the rate and extent of recovery of bulk material properties. FIG. 2f clearly demonstrates the exceptionally fast and complete recovery of viscosity. The rate and extent of recovery is unchanged over several cycles of breaking and reforming, highlighting the reversible nature of the non-covalently cross-linked hydrogel structure.

Figure 9:
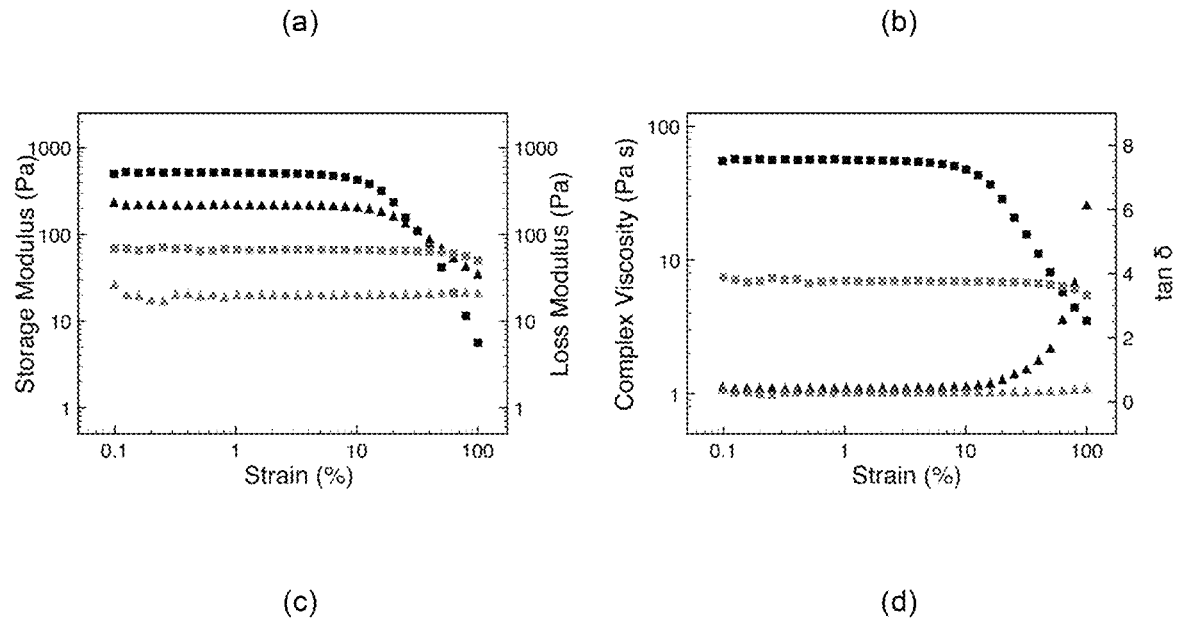
FIG. 9 is Dynamic oscillatory rheological characterization performed at 37° C. of the HEC-based hydrogels used in this study, where (a) is the storage and loss modulus and (b) is the complex viscosity and tan δ, from which these values are taken from strain amplitude sweep measurements. Further, (c) is the storage and loss modulus and (d) is the complex viscosity and tan δ, from which these values are taken from frequency sweep measurements. The black symbols represent refer to a hydrogel derived from an aqueous composition comprising HEC-Np 1.5 wt %, PVA-MV 0.3 wt % and CB[8] 1 eq. (black); whilst blue symbols represent HEC-Np 0.5 wt %, PVA-MV 0.1 wt % and CB[8] 1 eq. Squares refer to the left axis and triangles to the right axis.

Thus, in summary, strain dependent oscillatory rheology (see also FIG. 9a) displays an extremely broad linear viscoelastic region and it is only at higher loading (1.5 wt %) that a deviation from linear viscoelasticity is observed. The frequency dependence of the storage and loss oscillatory shear moduli (G' and G", respectively), clearly identifies hydrogel-like behaviour as the two are linear and parallel and G' is dominant across the whole range of frequencies observed (FIG. 9c). In general, the hydrogels are soft (G'=0:5 kPa at 1.5 wt % loading of HEC-Np) and display linear shear-thinning behaviour, yet they are highly elastic (tan δ=0.3).

Figure 3:
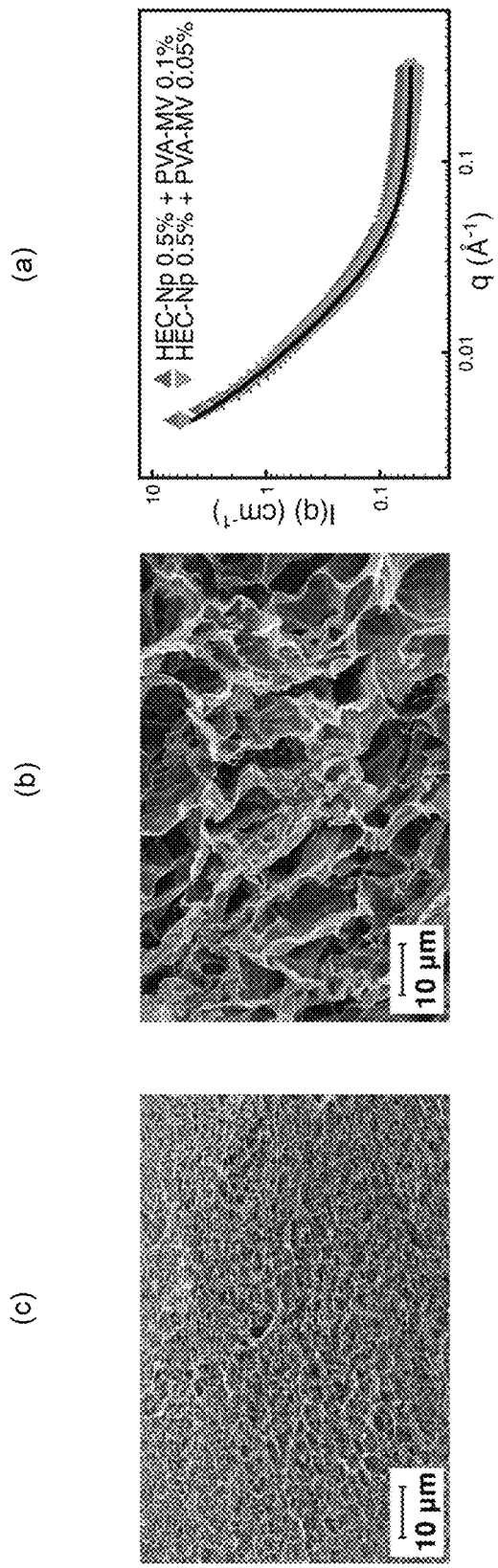
FIG. 3 (a) and (b) are scanning electron microscopic images of cryo-dried and lyophilized samples of (a) a hydrogel derived from an aqueous composition comprising HEC-Np (0.5 wt %)/PVA-MV (0.1 wt %)/CB[8] (1 eq.), and (b) a hydrogel derived from an aqueous composition comprising HEC-Np (0.5 wt %)/PVA-MV (0.05 wt %)/CB[8] (1 eq.).
Figure 4:
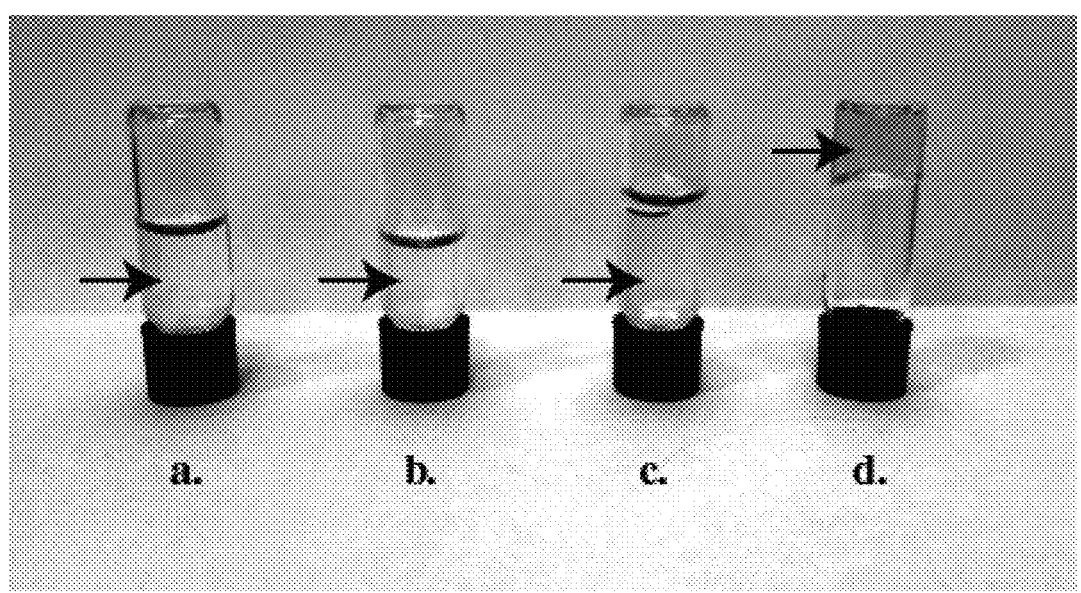
FIG. 4 is a photograph of an inverted vial test demonstrating the formation of the hydrogel from the aqueous mixture of PVA-MV (0.1 wt %), HEC-Np (0.5 wt %) and CB[8] (0.1 wt %) exclusively. (a) HEC-Np; (b) HEC-Np and PVA-MV; (c) HEC-Np and PVA-MV and CB[7]; and (d) HEC-Np, PVA-MV and CB[8].

The structure of the hydrogels formed at 0.5 wt % loading of HEC-Np were characterized by scanning electron microscopy (SEM) and small angle neutron scattering (SANS). FIG. 3 shows a large dependence of the observed microstructure for two cryo-dried and lyophilized samples on the relative loading of HEC-Np and PVA-MV@CB[8]. The higher loading of PVA-MV@CB[8] shown in FIG. 3a with the same loading of HEC-Np (0.5 wt %) yields much smaller pores than the analogous hydrogel in FIG. 3b. This is presumably on account of the higher cross-link density and agrees with previously observed trends (Appel et al. *J. Am. Chem. Soc.* 2010, 132, 14251-14260).

Figure 10:
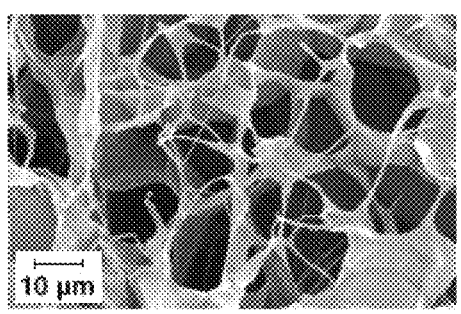
FIG. 10 is a scanning electron microscopy images of a cryo-dried and lyophilized samples of a hydrogel derived from an aqueous composition comprising HEC-Np 1.5 wt %, PVA-MV 0.3 wt % and CB[8] 1 eq.

SEM measurements were also taken for a hydrogel comprising HEC-Np 1.5 wt %, PVA-MV 0.3 wt % and CB[8] 0.3 eq. (see FIG. 10).

SANS Data Analysis

SANS experiments were conducted using the D11 instrument at the Institut Laue-Langevin high-flux reactor source in Grenoble, France. Neutrons are sensitive to the nm range of length-scales, thus a more refined picture of the molecular structure of the hydrogel could gained than that probed by SEM. The scattering data for the hydrogels superimpose, showing no major changes in the nanostructure with the amount of PVA-MV@CB[8]. The data can be appropriately described by a combination of the Debye-Bueche and Ornstein-Zerniche models which are widely used to account for the scattering from gels and polymeric solutions (Benguigui et al. *Euro. Phys. J. B.* 1999, 11, 439-444; Horkay et al. *Polymer* 2005, 46, 4242-4247). The correlation length could be fitted with values around 200 Å (±30 Å), which is rather large compared to reported values for polymeric gels, likely on account of the exceptionally low loading of polymeric material relative to previously reported systems, yet consistent with the calculated mesh size based on distances between guest moieties along an extended, well solvated polymer chain. The correlation length of the frozen-in structure, Ξ, could take a wide range of values, between 500 and 1000 Å. A high excess scattering was observed at low q, which followed a q$^{-4}$ Porod law, typical of a sharp interface, and suggesting the presence of very large size inhomogeneities in the sample. The scattering could therefore not be fully described by the Debye-Bueche and Ornstein-Zerniche models and a power law (q$^{-4}$) was needed to account for the full scattering curve. These inhomogeneities are likely resulting from insoluble pulp from the cellulose as the samples were not filtered before the scattering measurements were taken.

For gels composed of flexible polymer chains, the scattering intensity is usually described by the combination of two terms, a dynamic and a static component (see Horkay et al. *Macromolecules* 1991, 24, 2896-2902; Pezron et al. *Polymer* 1991, 32, 3201-3210). The dynamic term follows an Ornstein-Zernike law, as for polymer semi-dilute solutions in a good solvent, leading to a Lorentzian form of the scattering function given by:

$$I(q)_L = \frac{I(0)_L}{1+q^2\xi^2} \quad (1)$$

where $I_L(0)$ is the extrapolated structure factor at zero q and ξ, a thermal correlation term, which can be assimilated to a 'mesh size' of the gel network. The second term arises from frozen-in concentration fluctuations causing excess scattering at low q and is described by the Debye-Bueche term:

$$I(q)_{DB} = \frac{I(0)_{DB}}{\left(1+q^2\Xi^2\right)^2} \quad (2)$$

$I_{DB}(0)$ is the extrapolated structure factor at q=0 and Ξ the size of the inhomogeneities. This term accounts for a two density medium with a sharp interface. The combination of the Ornstein-Zernike (Lorentzian) and Debye-Bueche models gives the scattered intensity I(q) as follows:

$$I(q)=I(q)_L+I(q)_{DB} \quad (3)$$

Hydrogel Stimuli Responsiveness

Hydrogels prepared according to the above preparation method were placed into a small vial. In the case of liquids such as toluene or hexane, roughly an equivalent volume was added to the top of the hydrogel and the bilayer system mixed with a vortex for 10 seconds. In the case of solids such as 2,6-dihydroxynaphthalene and sodium dithionite, an excess (typically 3 equivalents) was added as a solid to the top of the hydrogel and the system mixed with a vortex for 10 seconds.

The CB[8] ternary complex, beyond providing a means for the preparation of self-assembled hydrogels, also imparts inherent stimuli-responsiveness to the resulting materials in a tunable manner. These hydrogels are highly sensitive to specific external stimuli, including competing second guests and reducing conditions. Addition of an excess of a competitive guest with mixing, i.e. 2,6-dihydroxynaphthalene or an equivalent volume of a solvent such as toluene, leads to dissociation of the polymer network and complete loss of bulk mechanical. In the case of toluene, partitioning of the toluene out of the aqueous layer after settling causes reformation of the hydrogel. On the contrary, when hexane was added instead of toluene, no alteration of the hydrogel properties was observed (hexane is not a suitable second guest for the CB[8] ternary complex). Additionally, dilution with an equivalent volume of H$_2$O only slightly reduced mechanical properties (see FIG. 2).

Another important advantage of this system is the one electron reduction of MV, which reversibly breaks the ternary complex on account of specific 2:1 MV':CB[8] complex formation (see Lee et al. *Chem. Commun.* 2002, 2692-2693; Coulston et al. *Chem. Commun.* 2011, 47, 164-166). Therefore, addition of sodium dithionite (a good reducing agent for MV) yields a low viscosity solution.

Toxicity Studies

Cells and media NIH 3T3 cells were cultivated in DMEM containing 10% fetal bovine serum (FBS) and 1% penicillin/streptomycin. Cells were grown as a monolayer and were passaged upon confluence using trypsin (0.5%, w/v in PBS). The cells were harvested from culture by incubating in trypsin solution for 10 min. The cells were centrifuged and the supernatant was discarded. Serum-supplemented DMEM (3 mL) was added to neutralize any residual trypsin. The cells were re-suspended in serum-supplemented DMEM at a concentration of 2×104 cells/mL. Cells were cultivated at 37° C. and 5% $CO_2$.

The toxicities of the hydrogel constituent polymers were assessed by determining their ability to affect the proliferation and viability of 3T3 cells cultured in DMEM. The polymers were incubated in 24-well multiplates at 1×104 cells per well for 24 h at 37° C. in 500 µL of medium. The different cell viabilities were evaluated using the MTT assay on the 3T3 cell lines. Here, 10 mL of sterile filtered MTT stock solution in PBS (5 mg/mL) was added to each well, reaching a final MTT concentration of 0.5 mg/mL. After 5 h, unreacted dye was removed by aspiration. The formazan crystals were dissolved in DMSO (100 mL per well), and the absorbance was measured using a microplate reader at a wavelength of 570 nm. Cell viability (%)=$[A]_{test}/[A]_{control}$× 100%, where $[A]_{test}$ is the absorbance of the wells with polymers and $[A]_{control}$ is the absorbance of the control wells. All experiments were conducted with six repetitions and averaged. The control group consists of cells incubated without polymers and cultured in DMEM.

Figure 11:
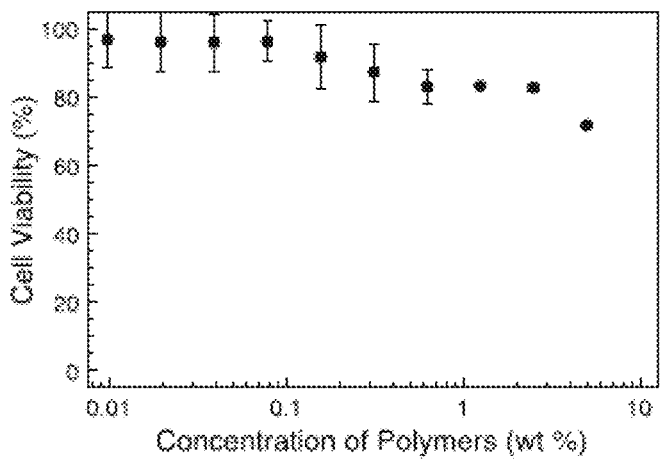
FIG. 11 is a graph showing the percentage viability of a 3TC cell population exposed to different concentrations of a mixture comprising the polymers HEC-Np and PVA-MV. The concentration is given as the total wt % of the polymers in an aqueous mixture.

In vitro cytotoxicity studies are of major importance when considering any biomedical application for such hydrogels and were performed using 3T3 cells. Toxicity studies were performed using only the polymer constituents in order to maximize the availability to the cells and limit increases in viscosity due to hydrogel formation in the presence of CB[8]. A recent study of both in vivo and in vitro toxicity of cucurbit[n]urils has recently been performed which demonstrates the biocompatibility and extremely low toxicity of macrocyclic hosts (Uzunova et al. *Org. Biomol. Chem.* 2010, 8, 2037-2042). The cytotoxicity of the polymers was tested at various concentrations ranging from 0.1 to 50 mg/mL and quantification of the cytotoxic response was done using the MTT assay. In general, the polymers do not show significant toxicity (FIG. 11). Additionally, the cytotoxicity of the leachable products from the copolymer gel was evaluated by incubating the gel in the cell culture medium over a period of 30 days at 37° C. to simulate the actual usage conditions. Quantification of the cytotoxic response was through the MTT assay. Aqueous extracts of the polymers do not show significant cytotoxicity against 3T3 cells, regardless of the incubation length. There was concern regarding the use of TDL as a catalyst in the polymer preparation described herein, particularly when TDL is a known cytotoxic chemical. However it has been shown that at very low concentrations (1 ppm), TDL does not elicit a cytotoxic response against L929 mouse broblast cells (Loh et al. *Biomaterials* 2007, 28, 4113-4123). From these studies, the polymeric constituents are not cytotoxic and there the resulting hydrogels are expected to be safe for biomedical applications.

Protein Release Studies from Hydrogels

Aqueous solutions of 1 and 3 wt % HEC-Np were mixed and left to equilibrate overnight at ambient temperature. Appropriate amounts of lysozyme or BSA solutions were loaded to a predetermined concentration of lysozyme or BSA in the polymer solution. Aqueous solution of PVA-MV (0.2 and 0.6 wt %) and CB[8] (0.2 and 0.6 wt %) were then prepared. In a typical example, 0.5 mL of protein-loaded HEC-Np polymer solution was injected into a sample vial and 0.5 mL of PVA-MV@CB[8] solution was added and the mixture shaken for approximately 1 s until the hydrogel formed. The sample vial was then placed in 7 mL of phosphate buffer release solutions in a test tube, which was incubated and shaken at 50 rpm in a water bath equilibrated at 37° C. The buffer solutions were replaced with fresh ones at predetermined time intervals, and the experiments were done in triplicate. The collected buffer solutions were lyophilized and kept at −80° C. for further analysis. The lysozyme and BSA contents were determined using the Pierce BCA Protein Assay kit. Quantization of lysozyme and BSA was based on a calibration curve, obtained using the fresh lysozyme and BSA standards, in the range of 20-2,000 mg/mL (see Loh et al. *J. Mater. Chem.* 2011, 21, 2246-2254).

The low polymer concentration and high water content of the gels of the invention are highly attractive for biomedical applications due to improved biocompatibility. Several methods for the preparation of protein loaded samples were investigated. Two model protein therapeutics were chosen for this study, Bovine Serum Albumen (BSA) and Lysozyme, on account of their difference in size, providing information the release of materials over a wide range of molecular sizes. As the hydrogels self-assemble rapidly at room temperature, it was possible to dissolve the protein with either of the polymeric solutions before mixing and in situ hydrogel formation. However, it was determined that the protein could easily be admixed with preformed hydrogel simply by mechanically stirring the protein as a solid into the hydrogel. The protein-loaded gels were formed and were incubated at 37° C. This form of protein loading method minimizes the risk of protein denaturation as it does not expose the protein to high heat or organic solvents during the formulation process. In this study, two factors affecting the protein release were studied, (1) the effect of polymer concentration (0.5 wt % versus 1.5 wt %) and (2) the effect of protein molecular weights (BSA, Mw: 67,000 g $mol^{-1}$ versus lysozyme, Mw: 14,000 g $mol^{-1}$).

Figure 12:
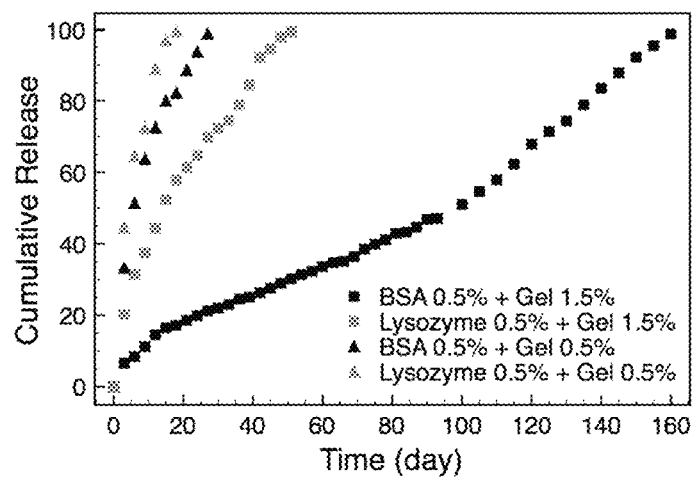
FIG. 12 is a graph showing the cumulative release of BSA and Lysozyme from two different hydrogels over time. The polypeptides are present at 0.5 wt % of the hydrogel, and the total polymer content of the hydrogel is 0.5 wt % or 1.5 wt %.

The proteins were released in a continuous fashion and their release profiles are shown in FIG. 12. For all the curves except for BSA-loaded 0.5 wt % gel, an initial burst release takes place before constant release is observed. When the polymer concentration is high, the rate of protein release is reduced and a more sustained release is observed. The burst release of the 0.5 wt % gel released approximately 50% of the BSA protein within the first 1 week whereas the 1.5 wt % gel managed to suppress this effect to approximately 10%. Moreover, BSA is a protein with a molecular weight of about 67,000 g $mol^{-1}$ whereas lysozyme has a molecular weight of about 14,000 g $mol^{-1}$. For BSA, the rate of release of the protein is slower when compared with lysozyme and a more sustained release is observed. The burst release is also effectively suppressed and the duration of sustained release is extremely promising. Previously, the extremely sustained protein release profile of up to 80 days was demonstrated by the poly(PEG/PPG/PHB urethane) thermogels reported by Loh et al. (Loh et al. Biomaterials 2007, 28, 4113-4123). When the protein is large, the rate of release becomes correspondingly slower as the mobility of the protein out of the gel is reduced. The release profile of all the polymers can be fitted to the following RitgerPeppas equation for drug release in the range of $M_t/M_\infty = 0.6$ (see Ritger et al. *J. Controlled Release* 1987, 5, 23; Ritger et al. *J. Controlled Release* 1987, 5, 37).

$$\frac{M_t}{M_\infty} = kt^n$$

Protein Bioactivity Studies

Esterase activity of BSA was determined by following the formation of p-nitrophenol from the synthetic substrate p-nitrophenyl acetate at 400 nm using a spectrophotometer. The reaction mixtures contained 50 µM p-nitrophenyl acetate and 20 µM protein in 0.1 M phosphate buffer, pH 7.4 at 37° C. A molar extinction coefficient for p-nitrophenol of $\varepsilon = 17{,}700$ M$^{-1}$ cm$^{-1}$ was used for all the calculation.

Activity of the lysozyme released from the gel was determined using EnzChek (RTM) Lysozyme Assay Kit (Molecular Probes, E-22013). The experimental protocols were performed as per the instructions provided in the kit.

Figure 13:
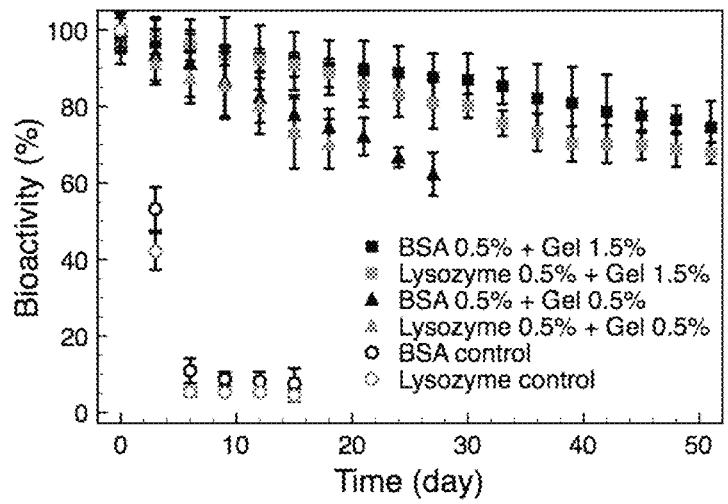
FIG. 13 is a graph showing the change in bioactivity of a BSA and Lysozyme released from a hydrogel over time. The polypeptides are present at 0.5 wt % of the hydrogel, and the total polymer content of the hydrogel is 0.5 wt % or 1.5 wt %.

The preservation of BSA activity is of great importance for any biological application involving gels. The biological activity of both the BSA and Lysozyme materials upon delivery from the hydrogel are shown in FIG. 13. The evaluation was performed using well established activity assays. Control experiments were performed whereby the proteins were kept in buffered solutions for the analogous time frames as the delivery. It is observed that BSA retains over 80% of its original activity when released from the gel even after 50 days, while only 2% of the activity is retained without any gel encapsulation. These results imply that BSA maintains most of its activity when retained within the gel structure, which is a reaction of the retention of the native structure by BSA.

Additional Experimental Results—Vinylbenzene Polymers

Additional experimental work described herein shows that using a polymer having a higher molecular weight, such as greater than 50 kDa, may be used to generate hydrogels.

Figure 14:
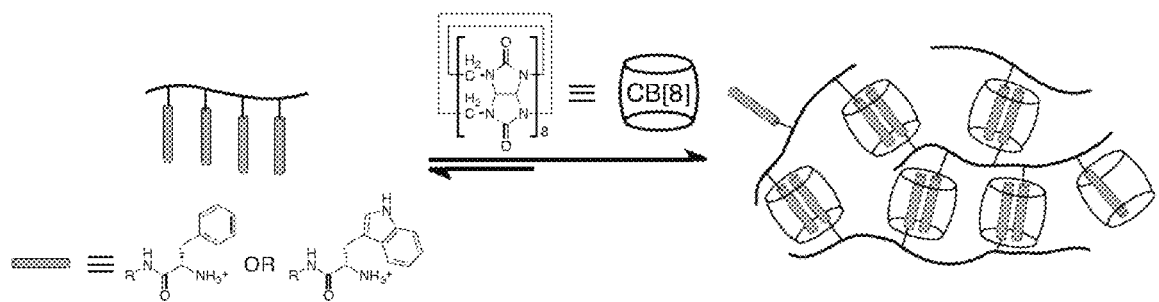
FIG. 14 is a schematic of hydrogel formation upon the mixture of CB[8] with a polymer having tryptophan or phenylalanine guests. The amino acids (represented by the shaded cylinders) bind in a 2:1 fashion with the host CB[8]. The R group of the amino acid is encapsulated within the hydrophobic cavity by non-covalent interactions. Further interactions occur between the protonated N-terminus of the amino acid unit and the CB[8] portal carbonyl groups.

The guest moieties used in the polymers are the commercially available and natural amino acids phenylalanine and tryptophan. The use of such amino acids reduces the potential toxicity profile of the system, but also simplifies the hydrogel from a three component system to a two component system (see FIG. 14). The well-known stimuli-responsive nature of the ternary complex and the ease of synthesis of the various components make this system well-suited for a variety of important biomedical and industrial applications.

The analytical and preparation techniques described above in relation to the cellulose polymers were also used to analyse and prepare the vinylbenzene polymers described below.

The work below shows that amino acids may be used as guests in a host, such as cucurbituril.

Water soluble styrenic monomers were copolymerised with synthetically derived aromatic amino acid monomers of phenylalanine and tryptophan. The resulting polymers are shown to form dynamic and self-healing physically cross-linked hydrogels via recognition and binding of the amino acids to cucurbit[8]uril. The work is described in detail below. The polymers used in this study had molecular weights of 10.9 kDa and 12.1 kDa. The hydrogels produced were found to have rheological properties where the loss modulus (G") is observed to dominate the storage modulus (G') at higher frequencies. The hydrogels of the present invention typically employ a polymer having a molecular weight that is 50 kDa or greater. It is found that the use of such polymers is associated with a hydrogel product having a dominant storage modulus (G') over loss modulus (G") for any frequency value in the range 0.1 to 100 rad/s.

The polymers used in this study have a molecular weight less than 50 kDa. As described herein, the hydrogels resulting from the complexation of the polymers do not have the desired rheological characteristics. As such, the experiments may be compared with the other examples, which relate to hydrogels that are formed from polymers with molecular weights of 50 kDa or greater. It will be appreciated that the hydrogels described in these examples is nevertheless capable of holding an encapsulant and therefore has a general use according to the broadest aspects of the present invention.

Design and Synthesis of Functional Polymers (Vinylbenzyl)trimethylammonium chloride-derived polymers are rigid and highly water soluble on account of their cationic charge, making this monomer ideal for copolymerisation with guest-functional monomers. Polymer rigidity is particularly important in order to enhance hydrogel strength by limiting intramolecular binding of the amino acid units on the same polymer chain. Rigid polymers are ideal as they promote intermolecular complex formation, leading to stronger materials.

For the purpose of copolymerisation, a compatible amino acid monomer was also required to ensure random distribution of the functional units. Therefore, synthesis of a styrene derived amino acid monomer was undertaken, as shown below. Coupling of the activated amino acids Boc-L-phenylalanine N-hydroxysuccinimide ester and Boc-L-tryptophan N-hydroxysuccinimide ester with (4-vinylbenzyl) amine in the presence of triethylamine afforded the Boc-protected amino acid monomers (StPhe, 3a and StTrp, 3b) to good yields.

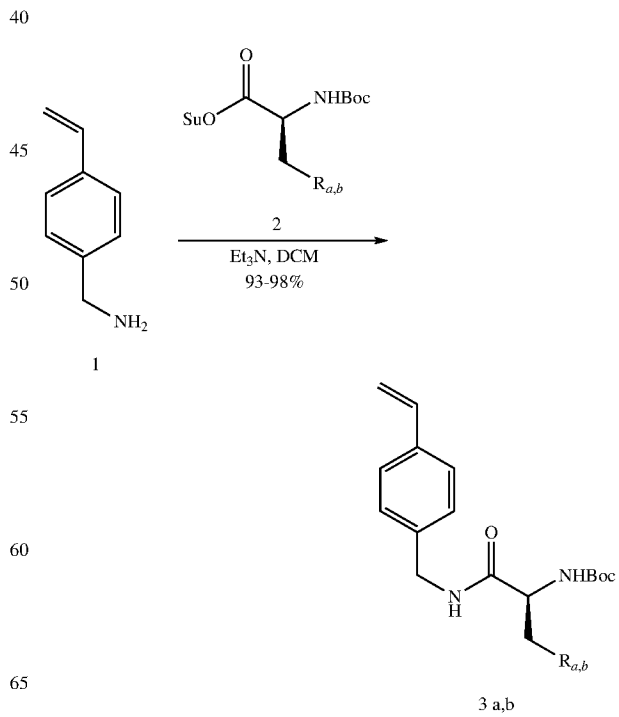

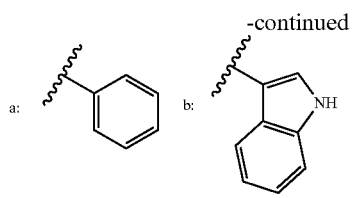

With the StPhe and StTrp monomers in hand, 'traditional' free radical copolymerisation with (vinylbenzyl) trimethylammonium chloride was performed using azobis cyanopentanoic acid (ACPA). Following acid treatment for Boc-deprotection, the cationic styrenic amino acid copolymers (5a, StPhe-StAm and 5b, StTrp-StAm) were afforded as HCl salts, which were highly water soluble and easily purified by dialysis. Proton NMR analysis of these copolymers determined that 7% of the monomers were functional with amino acids in both the phenylalanine and tryptophan cases (data not shown). By comparing the integration of the aromatic signal (7.5-6.0 ppm) with the integration of the trimethylammonium singlet (2.7 ppm), the excess of aromatic protons in the polymer was determined which directly correlated to the number of guest functional monomers incorporated into the final polymers.

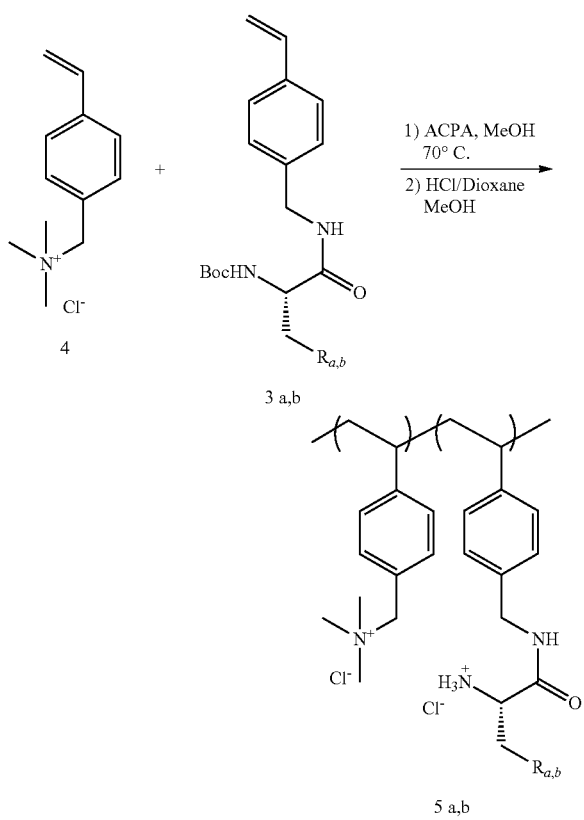

Synthesis of tert-butyl(1-oxo-3-phenyl-1-((4-vinylbenzyl)amino)propan-2-yl)carbamate (StPhe)

(4-Vinylbenzyl) amine (0.500 g, 3.75 mmol) was added dropwise to a solution of Boc-Phe-OSu (1.770 g, 4.88 mmol) in dichloromethane (DCM, 10 mL) at 0° C. Triethylamine (0.988 ml, 7.50 mmol) was then added dropwise to the cooled solution and the reaction was allowed to warm to room temperature and stirred for 24 hours. The reaction was quenched with saturated sodium carbonate solution and the product extracted with dichloromethane (DCM) (×3). The combined organic extracts were dried with magnesium sulfate, filtered and concentrated in vacuo. The crude residue was redissolved in a 50:50 mixture of hexane and ethyl acetate and washed through a pad of silica. Removal of the solvent in vacuo yielded the title compound as an amorphous white solid which was dried under a high vacuum overnight (1.324 g, 93%).

$^1$H-NMR Spectroscopy (CDCl3, 500 MHz) d (ppm)=7.35-6.95 (9H, m, Ar—H), 6.73-6.63 (1H, dd, J=17.5 Hz, 10.7 Hz, alkene-H), 6.10-6.02 (1H, br s, N—H), 5.78-5.68 (1H, dd, J=17.5 Hz, 0.8 Hz, alkene-H), 5.28-5.20 (1H, dd, J=10.7 Hz, 0.8 Hz, alkene-H), 5.10-4.95 (1H, br s, N—H), 4.40-4.37 (3H, m, CH2, CH), 3.16-2.99 (2H, m, CH$_2$), 1.39 (9H, s, CH3). $^{13}$C-NMR Spectroscopy (CDCl$_3$, 500 MHz) d (ppm)=170.98 (CO), 155.37 (CO), 137.19 (ArC), 136.87 (ArC), 136.63 (ArC), 136.32 (CH), 129.33 (ArCH), 128.72 (ArCH), 127.86 (ArCH), 126.95(ArCH), 126.41 (ArCH), 113.95 (CH$_2$), 56.08 (CH), 43.19 (CH$_2$), 38.53 (CH$_2$), 28.24 (CH$_3$). Elemental: Found C, 72.39; H, 7.51; N, 7.22. $C_{23}H_{26}O_3N_2$ calculated C, 72.60; H, 7.42; N, 7.36. FT-IR (ATR) n=3339 (m), 2983 (m), 1678 (s), 1658 (s), 1517 (s) cm$^{-1}$. HRMS: Found 381.2178 $[C_{23}H_{26}O_3N_2]^+$ calculated 381.2190.

Synthesis of poly(2-amino-3-phenyl-N-(4-vinylbenzyl)propanamide-co(vinylbenzyl)trimethylammoniumchloride) (StPhe-StAm)

StPhe (0.498 g, 1.31 mmol), (vinylbenzyl)trimethylammonium chloride (2.500 g, 11.81 mmol) and 4,4'-azobis(4-cyanopentanoic acid) (ACPA, 36.4 mg) were dissolved in methanol (MeOH, 7 mL) and degassed with nitrogen for 30 minutes. The reaction was heated to 70° C. and stirred for 24 hours. The product was precipitated with diethyl ether and collected by vacuum filtration. The crude residue was redissolved in MeOH (20 mL) and 4 N hydrogen chloride in dioxane solution (20 mL) added dropwise. The reaction was stirred for 8 hours and the deprotected polymer was precipitated with diethyl ether. The crude residue was purified by dialysis against water over 24 hours and the product lyophilised to yield an amorphous white solid (1.774 g, 62%) that was 7% StPhe and 93% StAm.

FT-IR (ATR) n=3374 (br), 3014 (m), 2923 (m), 1680 (m), 1614 (m), 1479 (s) cm$^{-1}$. GPC (H$_2$O): Mn=10.9 kDa, PDI=2.2.

Synthesis of tert-butyl(3-(1H-indol-3-yl)-1-oxo-1-((4-vinylbenzyl)amino)propan-2-yl)carbamate (StTrp)

(4-vinylbenzyl) amine (0.500 g, 3.75 mmol) was added dropwise to a solution of Boc-Phe-OSu (1.960 g, 4.88 mmol) in dichloromethane (DCM, 10 mL) at 0° C. Triethylamine (0.988 mL, 7.50 mmol) was then added dropwise to the cooled solution and the reaction was allowed to warm to room temperature and stirred for 24 hours. The reaction was quenched with saturated sodium carbonate solution and the product extracted with DCM (×3). The combined organic extracts were dried with magnesium sulfate, filtered and concentrated in vacuo. The crude residue was redissolved in a 50:50 mixture of hexane and ethyl acetate and washed through a pad of silica. Removal of the solvent in vacuo yielded the title compound as an amorphous white solid which was dried under a high vacuum overnight (1.541 g, 98%).

$^1$H-NMR Spectroscopy (CDCl$_3$, 500 MHz) d (ppm)=8.07 (1H, s, ArH), 7.70-7.62 (1H, d, J=7.8 Hz, Ar—H), 7.39-7.31 (1H, d, J=8.1 Hz, Ar—H), 7.30-7.20 (1H, m, Ar—H), 7.20-7.15 (1H, ddd, J=8.1, 6.9, 1.1 Hz, Ar—H), 7.15-7.10 (1H, ddd, J=8.1, 6.9, 1.1 Hz, Ar—H), 7.00-6.85 (3H, m, Ar—H), 6.71-6.61 (1H, dd, J=17.7, 10.9 Hz), 6.08-5.90 (1H, br s, N—H), 5.73-5.65 (1H, dd, J=17.7, 0.8 Hz, alkene-H), 5.27-5.20 (1H, dd, J=10.9, 0.8 Hz, alkene-H), 5.27-5.10 (1H, br s, N—H), 4.51-4.37 (1H, br s, CH), 4.32-4.18 (2H, m, CH$_2$), 3.39-3.25 (1H, dd, J=14.3, 5.2 Hz, HC—H), 3.25-3.10 (1H, dd, J=14.3, 7.5 Hz, HCH), 1.41 (9H, s). $^{13}$C-NMR Spectroscopy (CDCl$_3$, 500 MHz) d (ppm)=171.52 (CO), 155.45 (CO), 136.74 (ArC), 136.20 (CH$_2$), 136.05(ArC), 128.02 (ACH), 127.82 (ArC), 127.37 (ArCH), 126.32 (ArCH), 123.19 (ArCH), 123.03 (ArC), 122.35 (ArCH), 119.86 (ArCH), 113.92 (CH), 111.18 (ArCH), 110.67 (ArC), 55.31 (CH), 43.21 (CH$_2$), 28.43 (CH$_2$), 28.27 (CH$_3$). Elemental: Found C, 69.27; H, 6.98; N, 9.44. C25H29O3N3 calculated C, 71.57; H, 6.97; N, 10.02. FT-IR (ATR) n=3310 (br), 2978 (m), 2930 (m), 1693 (s), 1655 (s), 1494 (s) cm$^{-1}$. HRMS: Found 420.2303 [C$_{25}$H$_{30}$O$_3$N$_3$]$^+$ calculated 420.2287.

Synthesis of poly(2-amino-3-(3H-indol-3-yl)-N-(4-vinylbenzyl)propanamide-co-(vinylbenzyl)trimethyl-ammoniumchloride) (StTrp-StAm)

StTrp (0.550 g, 1.31 mmol), (vinylbenzyl)trimethylammonium chloride (2.500 g, 11.81 mmol) and ACPA (36.4 mg) were dissolved in MeOH (7 mL) and degassed with nitrogen for 30 minutes. The reaction was heated to 70° C. and stirred for 24 hours. The product was precipitated with diethyl ether and collected by vacuum filtration. The crude residue was redissolved in MeOH (20 mL) and 4N hydrogen chloride in dioxane solution (20 mL) added dropwise. The reaction was stirred for 8 hours and the deprotected polymer was precipitated with diethyl ether. The crude residue was purified by dialysis against water over 24 hours and the product lyophilised to yield an amorphous white solid (1.752 g, 60%).

FT-IR (ATR) n=3373 (br), 3012 (br), 2921 (br), 1679 (m), 1614 (m), 1478 (s) cm$^{-1}$. GPC (H$_2$O): Mn=12.1 kDa, PDI=2.4.

Hydrogel Preparation

Polymer solutions (20% w/v) were prepared and diluted with equivalent volumes of CB[8] solutions of various concentrations resulting in a final polymer concentration of 10% w/v. The combined solutions were mildly heated and shaken for a few seconds before allowing to cool to room temperature so the hydrogel could set. Phenylalanine and tryptophan bind within the CB[8] cavity in a 2:1 fashion (see Heitmann et al. *J. Am. Chem. Soc.* 2006, 128, 12574-12581). Therefore, 0.5 equivalents of CB[8] theoretically affords 100% crosslinking of the aromatic amino acid units. Initial CB[8] titrations into polymer solutions exemplified this well. Polymer solutions containing 20% by weight of the functional polymer were diluted with equivalent volumes of solutions containing various equivalents of CB[8], mildly warmed and shaken. As predicted, addition of CB[8] resulted in large increases in viscosity which was easily visualised by inverted vial tests (images not shown). It was observed that with no CB[8] the polymer solution remains transparent and the colourless solution flows. With 0.35 equivalents of CB[8] the solution is much more viscous but retains some flow. Addition of ≥0:5 equivalents of CB[8] caused the solution flow to slow dramatically upon vial inversion. Addition of 1 equivalent of CB[8] could in theory favour 100% formation of 1:1 amino acid⊂CB[8] complexes.

As strong hydrogels are still formed this is clearly not the case. As a control, 0.5 equivalents of CB[7] was also added to a polymer solution. CB[7] is large enough to bind only one Phe/Trp unit, thereby unable to promote crosslinking. With CB[7] addition no change in viscosity was observed, therefore 1:1 binding of Phe or Trp to a CB[n] molecule is not constructive for gel formation. As a second control non-functional poly[(vinylbenzyl)trimethylammonium chloride] (p-StAm) was also synthesised. Upon addition of CB[8] to a solution of the control StAm polymer at 10% by weight, no visible change in viscosity was observed. Hydrogel formation, therefore, arises exclusively from the 2:1 binding of the charged amino acids inside the CB[8] cavity and the cationic polymer backbone is not involved in the crosslinking process.

Rheological Characterisation of the Supramolecular Hydrogels

Supramolecular hydrogels have been successfully designed and prepared and rheological characterisation was performed to quantify their mechanical properties. Rheological analysis was carried out on supramolecular hydrogels prepared from the mixture of the 5a and 5b solutions with various molar equivalents of CB[8] (relative to amino acid functionalised units, e.g. 0, 0.05, 0.15, 0.35, 0.50, 0.70 equivalents) corresponding to various theoretical percentage crosslinking. Proceeding beyond the theoretical limit of 100% crosslinking (from 0.5 equivalents of CB[8] to 0.7 equivalents) are two possible outcomes: a) The gel properties, including viscosity, decrease. In the phenylalanine case 20% of the amino acid units would be bound in a 1:1 fashion and only 80% of the amino acid units in a 2:1 fashion leading to crosslinking. This is due to the first binding constant being equivalent to the second. In the tryptophan case, the second binding constant is weaker than the first and so 40% of the amino acids would be bound in a 1:1 fashion and 60% in a 2:1 fashion (Heitmann et al. J. Am. Chem. Soc. 2006, 128, 12574-12581). Therefore, at 0.7 equivalents of CB[8] the actual crosslinking would be either 80% or 60% dependant on the amino acids used. b) As 2:1 binding is more favourable than 1:1 binding (i.e. higher K$_{eq}$ value for the ternary complex in comparison with the binary complex) the excess CB[8] suspended in the solution would not prevent crosslinking as is case 'a' but instead increase viscosity by acting as a solid viscosity modulator. It is also possible that excess CB[8] in solution would promote formation of the ternary complex simultaneously enforcing 100% crosslinking and reducing the apparent rate of dissociation of the components.

Oscillatory Measurements

Figure 18A:
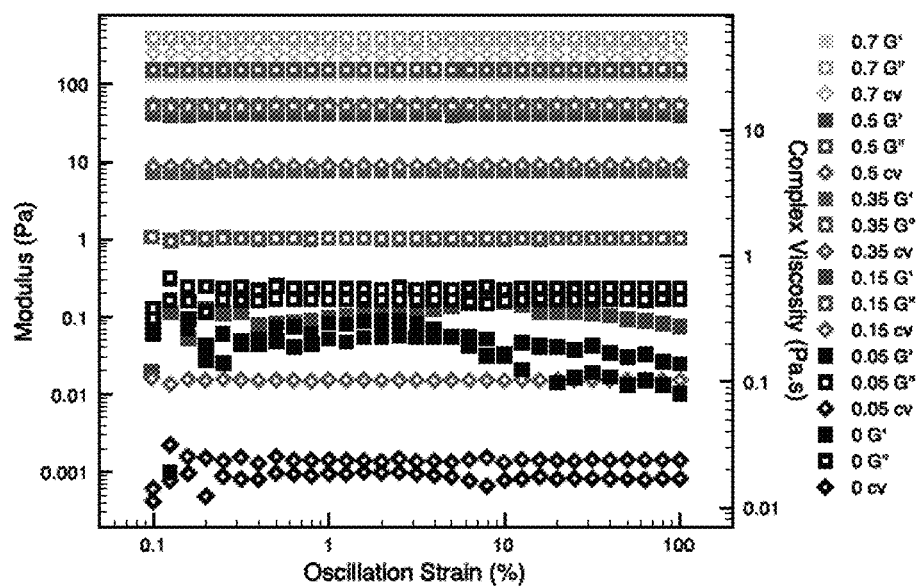
FIGS. 18(a) and 18(b) are graphs of the strain dependant oscillatory shear measurements for the hydrogel derived from StPhe-StAm (FIG. 18(a)) and StTrp-StAm (FIG. 18(b)). The values of G', G" and cv increase from bottom to top.
Figure 18B:
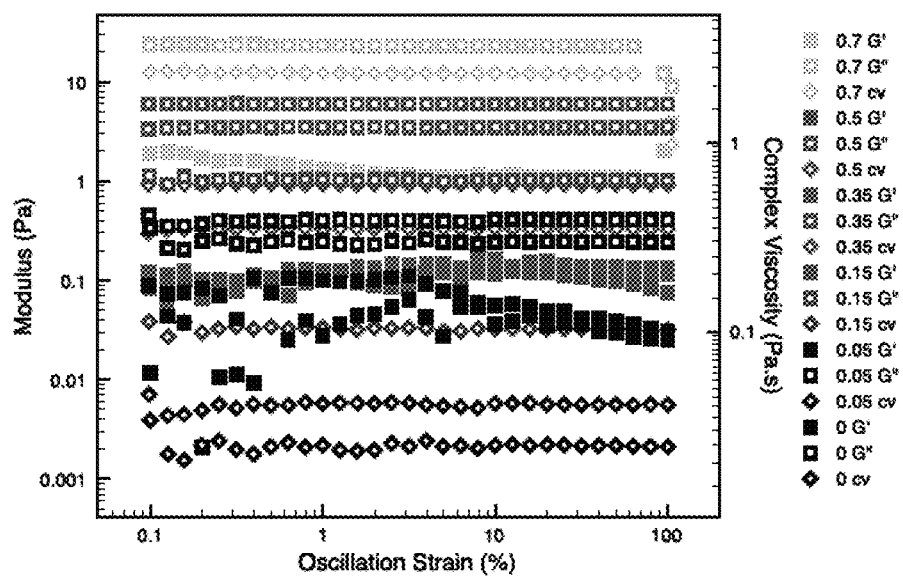

Strain-dependant oscillatory shear measurements at 20° C. were first performed in order to determine the linear viscoelastic properties of the material. Throughout the experiment all hydrogels were shown to have a broad viscoelastic window and no deviation from linearity was observed even at the highest oscillation strain, except for the StTrp-StAm gels containing 0.7 equivalents (see FIGS. 18a and 18b). Both materials, regardless of CB[8] concentration retained their broad viscoelastic regions. It was observed that, with increasing CB[8] concentration, the plateau modulus of the materials increased, the guest moieties. Interestingly, the moduli for the StPhe-StAm are distinctly larger than those of the StTrp-StAm gels by an order of magnitude.

Figure 15A:
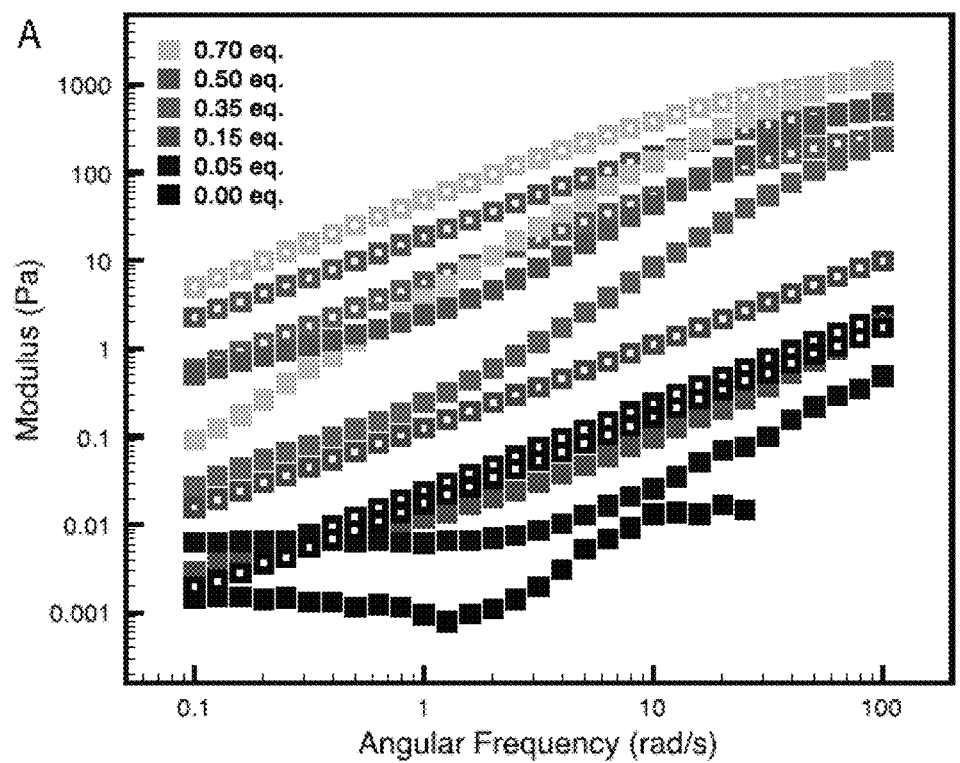
FIGS. 15(a) and 15(b) are graphs showing the frequency-dependent oscillatory rheology of StPhe-StAm (FIG. 15(a)) and StTrp-StAm (FIG. 15(b)) hydrogels with varying equivalents of CB[8]. The open symbols are loss moduli, G" and closed symbols are storage moduli, G'. The amount of CB[8] varies from 0.00 equiv. (bottom lines) to 0.70 equiv. (top lines).
Figure 15B:
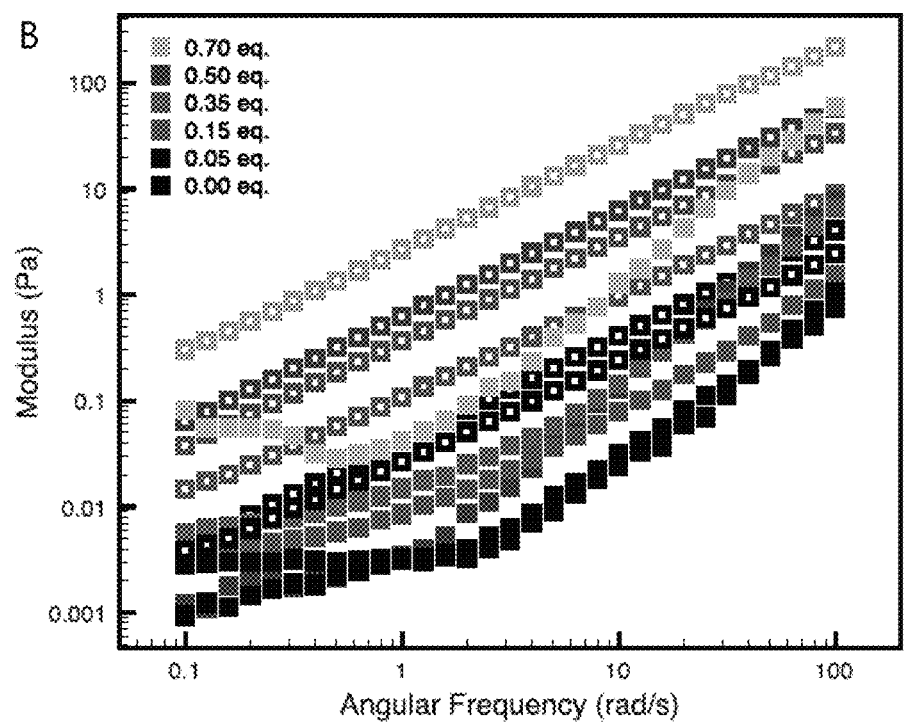

Frequency-dependant oscillatory rheological measurements were also performed on the materials within the linear viscoelastic regime (FIGS. 15A and 15B). As with the strain-dependant oscillatory measurements, the moduli of the StPhe-StAm gels are a magnitude higher than those of the StTrp-StAm materials. It is also worthwhile noting that the StPhe-StAm gels become elastically active at lower angular frequencies than the StTrp-StAm gels. In both cases, the more equivalents of CB[8] added caused not only an increase in both the storage and loss moduli of the gel but also a decrease in the angular frequency at which the storage modulus (G') becomes dominant over the loss modulus (G''). With more CB[8] present, at any one time there will be more crosslinks between the polymers, allowing the material to behave more elastically as the supramolecular network undergoes a higher energy penalty to break.

As the crossover point occurs at lower angular frequencies with greater CB[8] concentration we can infer that a greater degree of crosslinking has been achieved and that higher CB[8] concentrations (even beyond 0.5 equivalents) enforce 2:1 complexation. This leads to the conclusion that the equilibrium of ternary complex formation does not lie completely toward 2:1 complex formation. Instead it is envisaged that in this case the equilibrium between the free amino acid units and CB[8] and their respective 1:1 binary complex lies to the left. By increasing CB[8] concentration 1:1 complexation is enforced by Le Chateliers principle which then proceeds to ternary complex formation which is energetically favourable.

Steady Shear Measurements

Figure 16A:
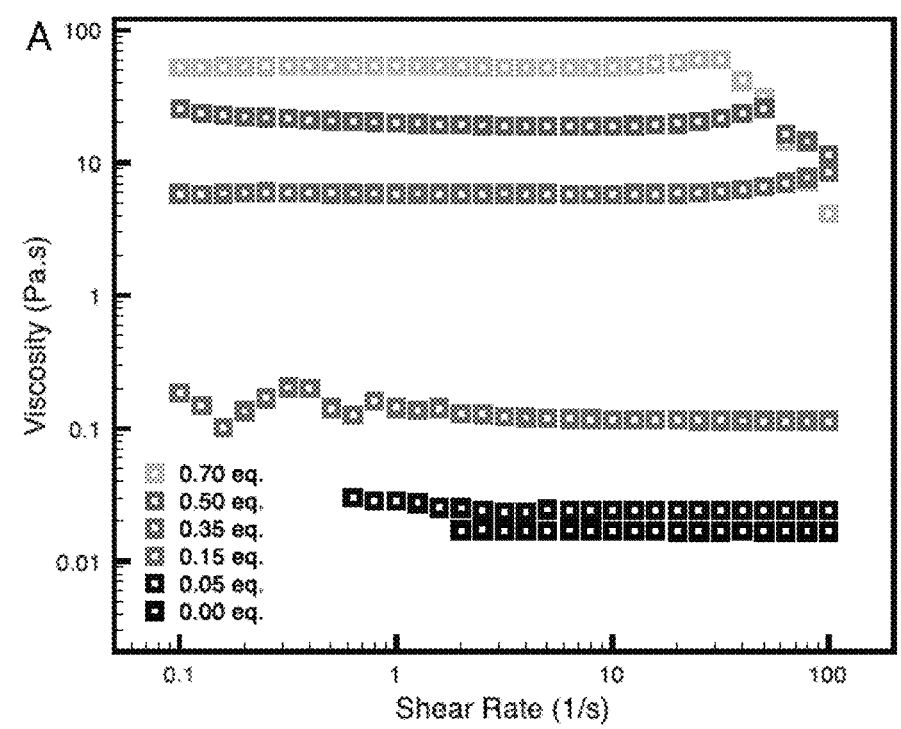
FIGS. 16(a) and 16(b) are graphs showing the steady shear rheological measurements of hydrogels formed with StPhe-StAm (10% w/v)(FIG. 16(a)) and StTrp-StAm (10% w/v)(FIG. 16(b)) with increasing quantities of CB[8]. The amount of CB[8] varies from 0.00 equiv. (bottom lines) to 0.70 equip (top lines).
Figure 16B:
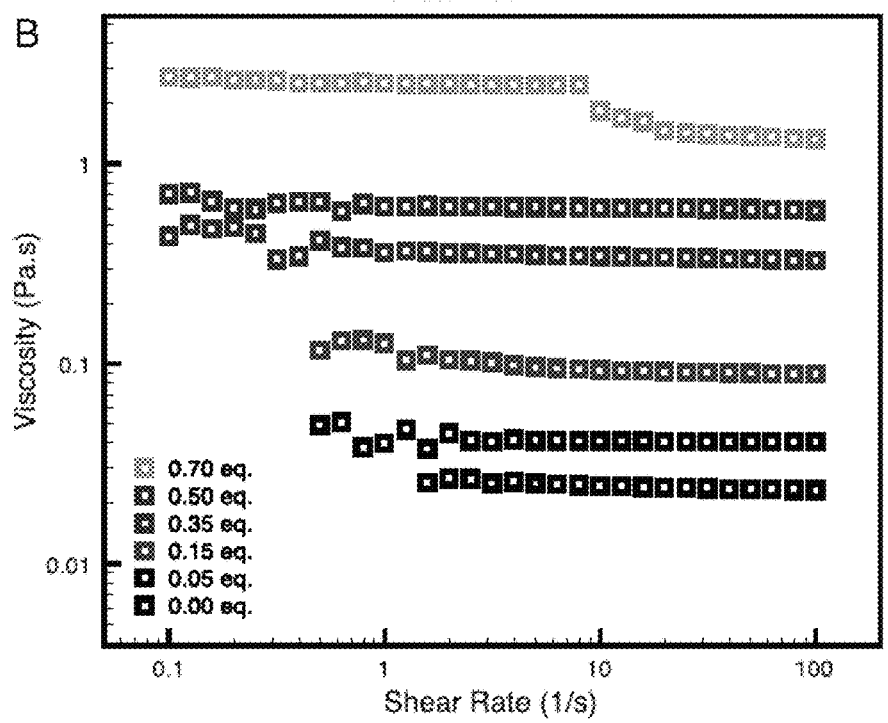

Steady shear rheological measurements were performed on both the StPhe-StAm and StTrp-StAm gels to determine the mechanical effect of varying amounts of CB[8] (FIGS. 16A and 16B). In both cases, the zero-shear viscosity of the materials increased with equivalents of CB[8] added, even beyond 0.5 equivalents. Initially the gels behaved as Newtonian materials with no change in viscosity. At high shear rates some gels with higher CB[8] loading displayed a slight degree of shear-thickening as shear rate increased. All materials displayed shear thinning behaviour under high shear conditions.

Figure 7:
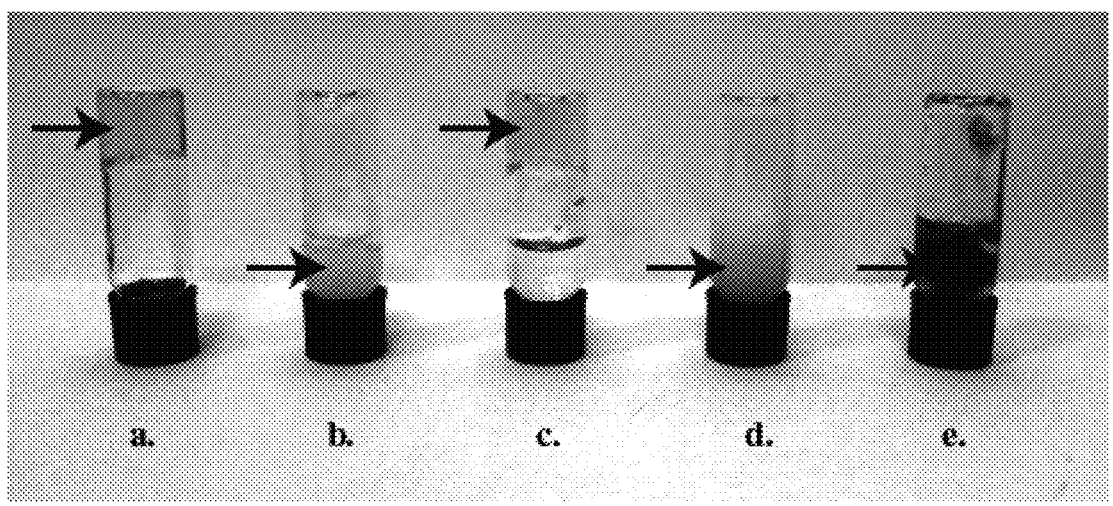
FIG. 7 is a photograph of an inverted vial test showing the stimuli responsivity of a hydrogel formed from HEC-Np 0.5%/PVA-MV 0.1%/CB[8] 1 eq. This hydrogel is shown in (a) and the hydrogel has a variable responsiveness to perturbation in the presence of (b) hexane; (c) toluene; (d) a competitive second guest 2,6-dihydroxynaphthalene; and (e) a sodium dithionite reducing agent. In the case of (c) the intact hydrogel can be seen with its original colour and is indicated by the arrow while the hexane layer has flowed to the bottom of the vial.
Figure 8:
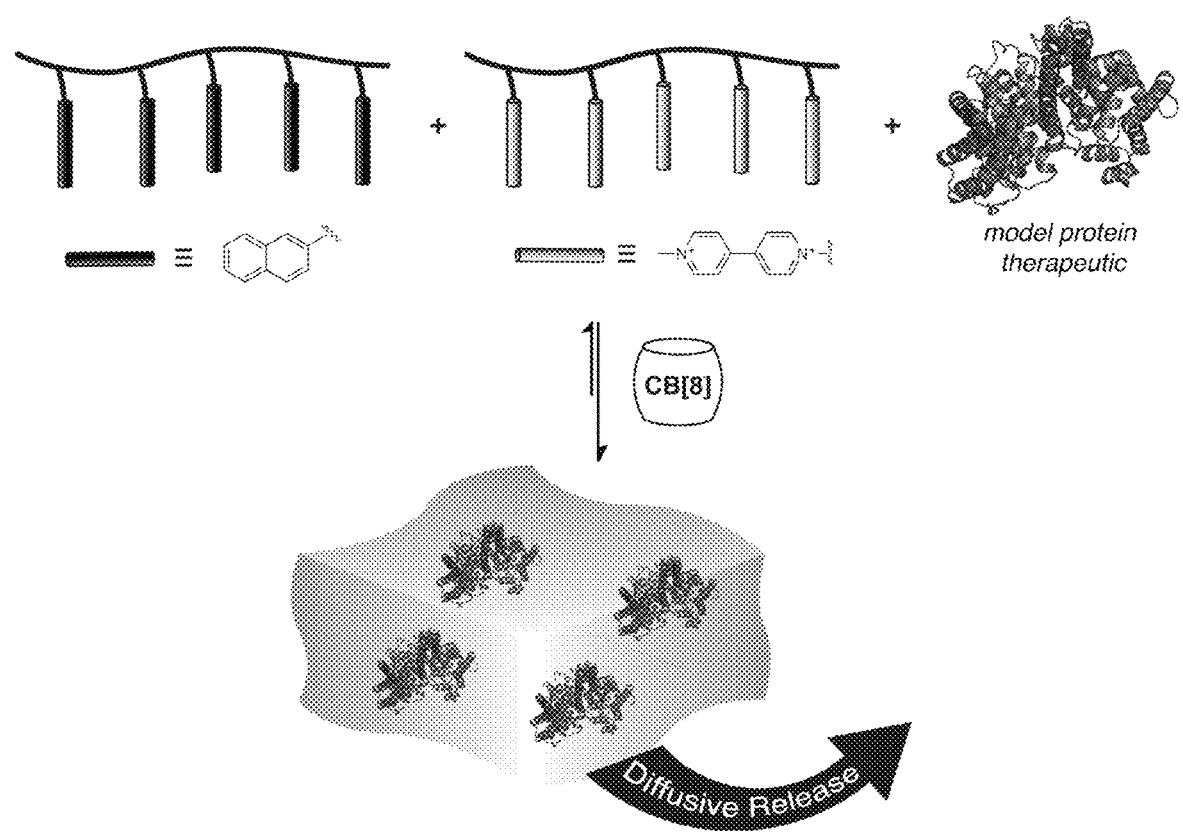
FIG. 8 is a schematic of the preparation of a hydrogel embodiment of the invention from napthyl and MV containing polymers in the presence of a model protein therapeutic.
Figure 17:
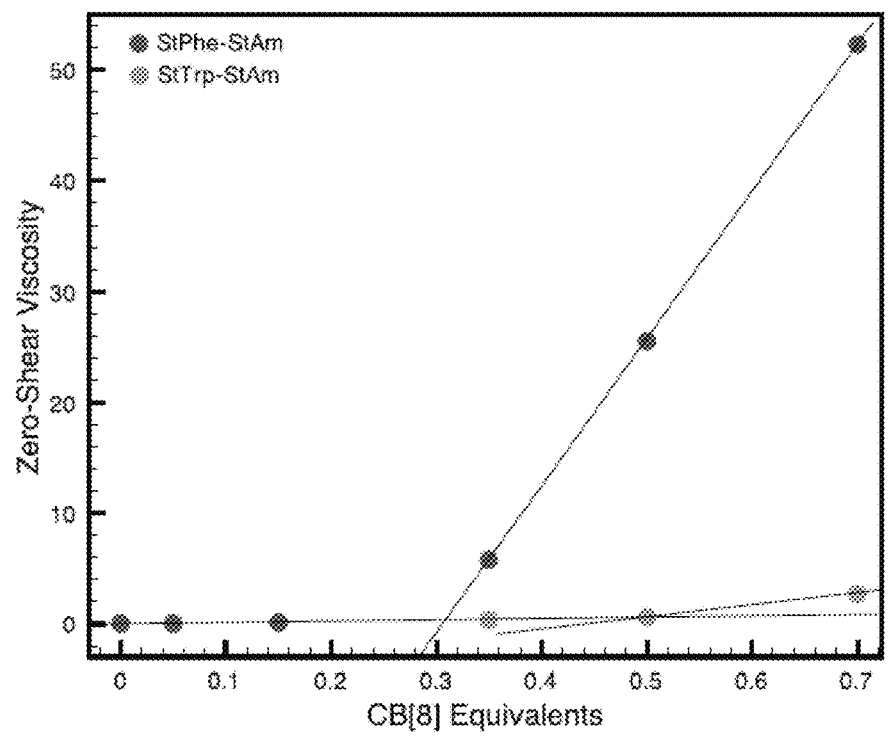
FIG. 17 is a graph showing the effect of CB[8] concentration on zero-shear viscosity at increasing shear rate for the hydrogels formed with StPhe-StAm and StTrp-StAm. The three data points for StTrp-StAm lies at ca. 0 zero shear viscosity for 0.35, 0.5 and 0.7 equivalents of CB[8]. The remaining six data points relate to the behaviour of StPhe-StAm.

Considering the zero-shear viscosities only, upon increasing addition of CB[8] both the StPhe-StAm and StTrp-StAm materials displayed an increase as would be expected (FIG. 7). Whilst initially at low CB[8] concentrations both materials have very low and similar viscosity, once beyond 0.15 equivalents of CB[8], the StPhe-StAm gel zero-shear viscosity increases at a much greater rate. This shows the ternary Phe2CB[8] complex is much stronger than the Trp2⊂CB[8] complex. FIG. 17 also exemplifies the equivalents of CB[8] required to induce gelation. Extrapolating lines of best fit for each material show gelation points for the two materials to be distinctly different. The StPhe-StAm polymer requires only 0.305 equivalents of CB[8] for gelation to begin whereas the StTrp-gel requires 0.5 equivalents. For the StTrp-StAm polymer viscosity is not dramatically altered with CB[8] concentration until surpassing the theoretical 100% crosslinking point. This is accountable for by the difference in association constants of the amino acids to CB[8] and how this may affect the dynamic equilibrium present.

Additional Experimental Results—Hyaluronic Acid and Cellulose Polymers

HA and cellulose polymers having phenylalanine guest compounds were prepared. The resulting polymers are shown to form dynamic and self-healing physically cross-linked hydrogels via recognition and binding of the amino acid to cucurbit[8]uril.

The molecular weights of the polymers were above 50 kDa. The experiments described below show that a hydrogel may be prepared from a biological polymer, such as a polysaccharide polymer, using biological guest molecules. The hydrogel formed therefore has a predominant biological component.

Preparation of Azide Phe

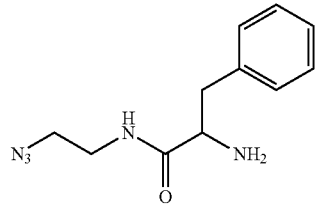 [SMILES: [N-]=[N+]=NCCNC(=O)C(N)Cc1ccccc1]

Sodium azide (11 g, 169 mmol) and 2-bromoethylamine hydrobromide (10 g, 49.0 mmol) were dissolved in water (150 mL) and heated at 75° C. for 24 hours. 50 mL of a 10% NaOH solution was added and product extracted into diethyl ether, dried with magnesium sulfate and filtered. Product concentrated to dryness in vacuo to yield 1.69 g of a yellow oil: 2-azidoethylamine.

The yellow oil was added to a solution of Boc-Phe-OSu (7.115 g, 19.7 mmol), in DMF (200 mL) and cooled in an ice bath. Triethylamine (2.72 mL) added dropwise and the reaction stirred for 12 hours before quenching with water. The product was extracted into ethylacetate and concentrated to dryness. The crude residue was dissolved in 20 mL of 2 M HCl in diethyl ether and stirred for 4 hours. The resulting precipitate was filtered off and washed with further diethyl ether yielding the product (azide-phe) as a white solid in the form of a HCl salt.

Preparation of Cellulose Polymer—CMC-Phe Polymer

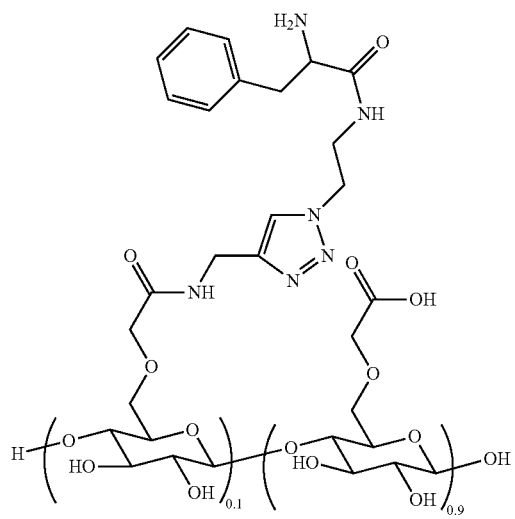

200 mg of carboxymethyl cellulose (CMC) sodium was dissolved in pH 4 buffer (16 mL). To this solution was added propargyl amine (172 uL, 2.68 mmol), N-hydroxysuccinimide (NHS, 187 mg, 1.625 mmol) and N-(3-Dimethylaminopropyl)-N'-ethylcarbodiimide hydrochloride (EDC, 312 mg, 1.625 mmol). The reaction mixture was stirred for 24 hours and the intermediate product purified by dialysis against brine (24 hours) then water (48 hours).

The intermediate polymer was isolated by lyophilisation. The amorphous product was redissolved in a 1:1 mixture of water and ethanol (20 mL). Azide-Phe (73.25 mg, 0.245 mmol) added followed by sodium ascorbate (16.3 mg, 0.0823 mmol) and copper (II) sulfate pentahydrate (21 mg, 0.0823 mmol). The reaction mixture was stirred overnight and the product was purified by dialysis against sodium hydrogencarbonate solution (48 hours) and then water (48 hours). The product was isolated by lyophilisation.

The Mw of the polymer was ca. 700 kDa.

Preparation of Cellulose Polymer—HA-Phe Polymer

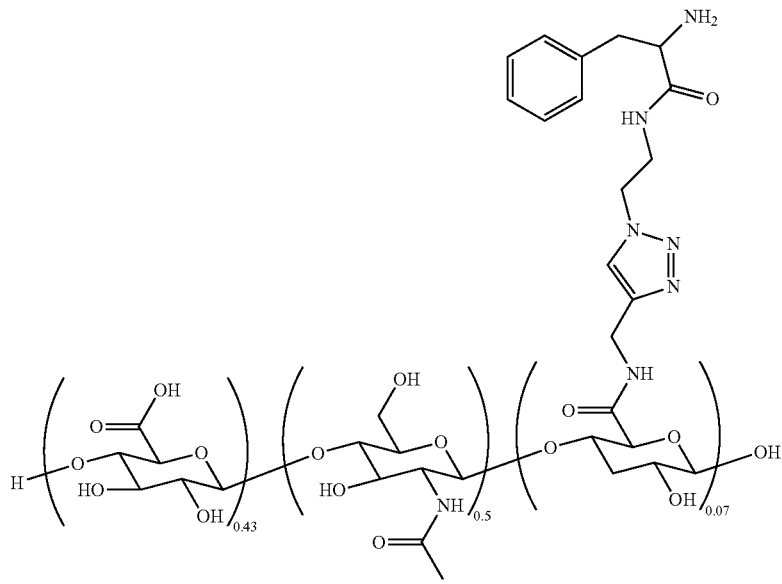

The polymer was prepared in the same manners as the cellulose polymer above, except that carboxymethyl cellulose was replaced with hyaluronic acid (200 mg).

The Mw of the polymer was ca. 200 kDa.

Hydrogel Preparation

Hydrogels based on the CMC-Phe and HA-Phe polymers described above were prepared in a similar manner to the vinylbenzene polymer hydrogels (also described above).

The CMC-Phe hydrogel was prepared from an aqueous solution comprising 2% w/v of the cellulose polymer and 0.5 equivalents of CB[8]. The formation of the hydrogel was apparent from an inverted vial test (images not shown). In the absence of CB[8] an aqueous solution comprising 2% w/v of the cellulose polymer does not form a hydrogel.

The HA-Phe hydrogel was prepared from an aqueous solution comprising 2% w/v of the HA-Phe polymer and 0.5 equivalents of CB[8]. The formation of the hydrogel was apparent from an inverted vial test (images not shown). In the absence of CB[8] an aqueous solution comprising 2% w/v of the HA polymer does not form a hydrogel. Where CB[7] was used in place of CB[8] (at similar equivalency), the HA polymer does not form a hydrogel.

Additional Experimental Results—Anthracene Hydrogels

Figure 19:
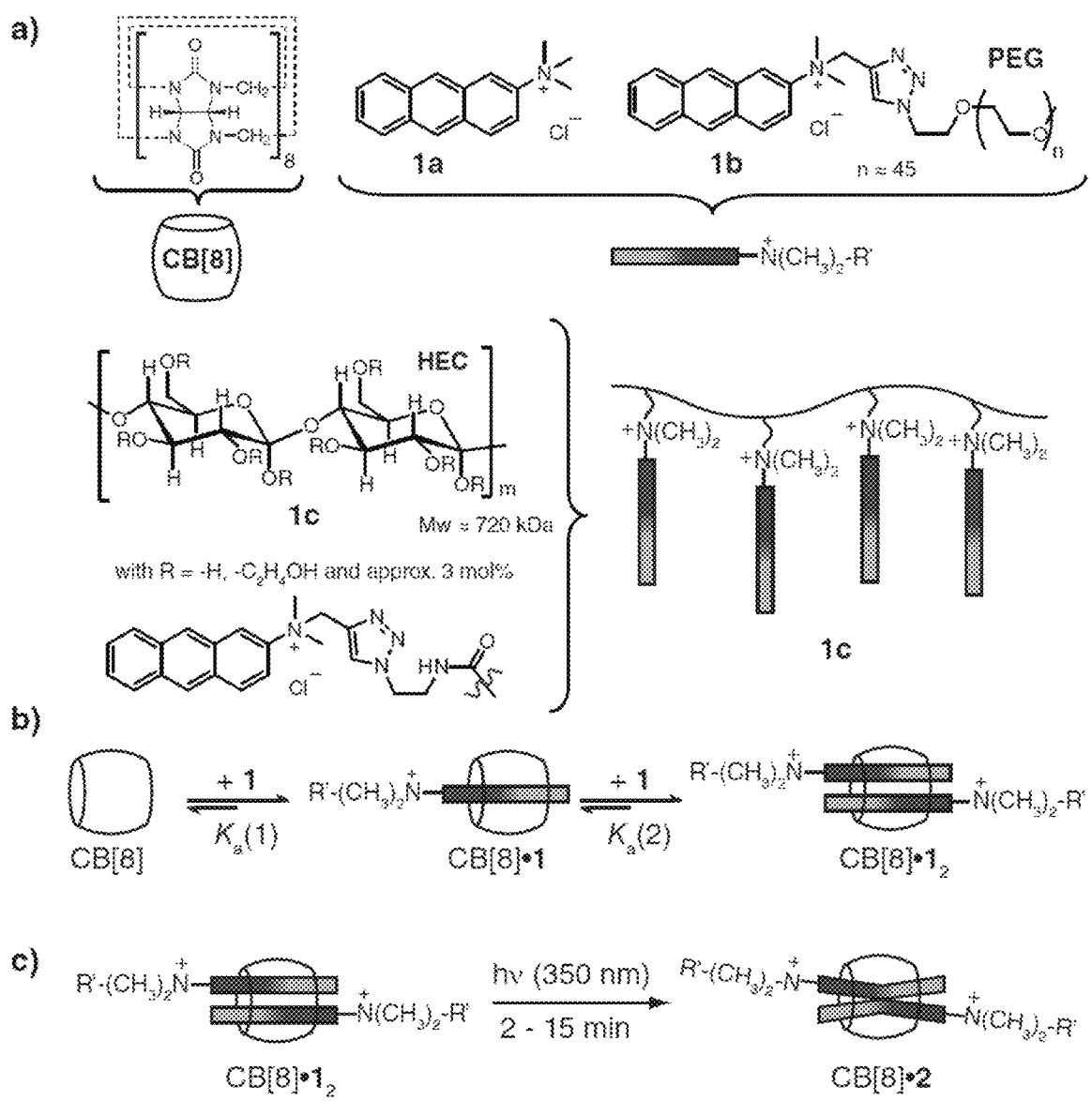
FIG. 19 shows (a) the chemical structures of compounds used in the dimerisation study: CB[8], small-molecule cationic anthracene-species 1a and its macromolecular analogues 1b (end-group functionalised poly(ethylene glycol) polymer, PEG) and 1c (side-chain functionalised hydroxyethyl cellulose, HEC); (b) a reaction schematic of CB[8] "handcuffing" together two anthracene-moieties in a face-to-face π-π-stack to form a 1:2 homoternary complex in water; and (c) a reaction schematic of the photoirradiation of the 1:2 ternary complex with a 350 nm light-source leads to nearly quantitative [4+4] photodimerisation within minutes.

Cucurbit[8]uril (CB[8]), can accommodate up to two aromatic guest molecules simultaneously inside its cavity as shown in FIG. 19(b), to form either 1:2 CB[8](guest)$_2$ homoternary complexes with monocationic guests or 1:1:1 heteroternary complexes with both a dicationic and a neutral guest. The preorganisation of two anthracenemoieties (see FIG. 19(a)) in the cavity of CB[8] in a face-to face π-π-stack dramatically increases the rate of photodimerisation between the two anthracenes and can be further utilised to photochemically ligate and cross-link polymers. This is discussed and exemplified below.

The anthracene-molecules were designed to carry a positive charge directly adjacent to the aromatic core in order to allow for strong cornplexation with CB[8]. For steric reasons, substitution of the 9-position of anthracene would impede the ability to form ternary complexes with CB[8]. Thus, anthracene derivatives carrying a substituent in the 2-position were used. Commercially available 2-amino-anthracene was subjected to reductive amination with paraformaldehyde and sodium cyanoborohydride which proceeded smoothly to yield N,N'-dimethyl-2-amino-anthracene in good yield and high purity without the need for further purification. Subsequently, quaternary ammonium salts were obtained employing powerful alkylating reagents such as methyl iodide (to yield 1a) and propagyl bromide (to yield a "click"-able precursor to 1b and 1c) with moderate yields.

Nevertheless, the purification steps (filtration) and ion-exchange to yield the chloride salt required only minimal effort. Labelling of macromolecules with such anthracene-moieties was achieved through copper-accelerated cycload-dition reactions from readily available end-group functional azidopoly(ethylene glycol) (PEG) and side-chain functional azidohydroxyethyl cellulose followed by purification through dialysis.

Host-Guest Complexation and Photodimerisation of Anthracene 1a

Initially, the binding characteristics of small molecule 1a with CB[8] were studied by $^1$H NMR, UV/vis and fluorescence spectroscopy, ESI-MS and isothermal titration calorimetry (ITC). In agreement with literature reports of other homoternary 1:2 CB[8]·(guest)$_2$ complexes (Jiao et al. *J. Am. Chem. Soc.*, 2010, 132, 15734; Liu et al. *Chem. Eur. J.*, 2011, 17, 9930), the characteristic shifts of the aromatic proton peaks were observed in the $^1$H NMR spectrum upon addition of CB[8]. UV/vis titration experiments (not shown) yielded evidence for a 1:2 complex stoichiometry, see FIG. 19(b). Furthermore, a strong excimer band emerged in the emission spectra of 1a when CB[8] was added, which is indicative of a face-to-face π-π-stack of anthracenemoieties in the host's cavity (Liu et al. Chem. Eur. J., 2011, 17, 9930). The dominant species in the ESI-MS spectra can be assigned to the CB[8]·1a$_2$ complex, which further confirms the suggested 1:2 homoternary complex formation of CB[8] with 1a.

Moreover, in ITC experiments the inflection point of the isotherm was observed at a 1:2 ratio of CB[8] to 1a, in agreement with the proposed 1:2 complex stoichiometry in solution. The overall aqueous ternary binding constant Ka(ternary)=(1.0±0.5)×10$^{12}$M$^{-2}$ is essentially identical to the Ka(ternary) of a recently reported anthracenepyridinium guest. A deconvolution of Ka(ternary) into the individual binding constants K$_a$(1) and K$_a$(2), albeit numerically somewhat uncertain (Heitmann et al. J. Am. Chem. Soc., 2006, 128, 12574), K$_a$(1)=(4±1)×10$^4$ M$^{-1}$ and K$_a$(2)=(2±1)×10$^7$ M$^{-1}$, clearly shows strong positive cooperativity, in contrast to previous reports of structurally similar guests (Heitmann et al. J. Am. Chem. Soc., 2006, 128, 12574; Jiao et al. J. Am. Chem. Soc., 2010, 132, 15734). Finally, the binding of 1a with CB[7], a smaller member of the cucurbit[n]uril family that can only form 1:1 complexes with aromatic guests (Kim et al. J. Am. Chem. Soc., 2000, 122, 540; Lagona et al. Angew. Chem. Int. Ed., 2005, 44, 4844) was also investigated with the aforementioned techniques and most importantly no excimer band was observed in the emission spectrum of an aqueous solution of CB[7] and 1a.

Figure 20:
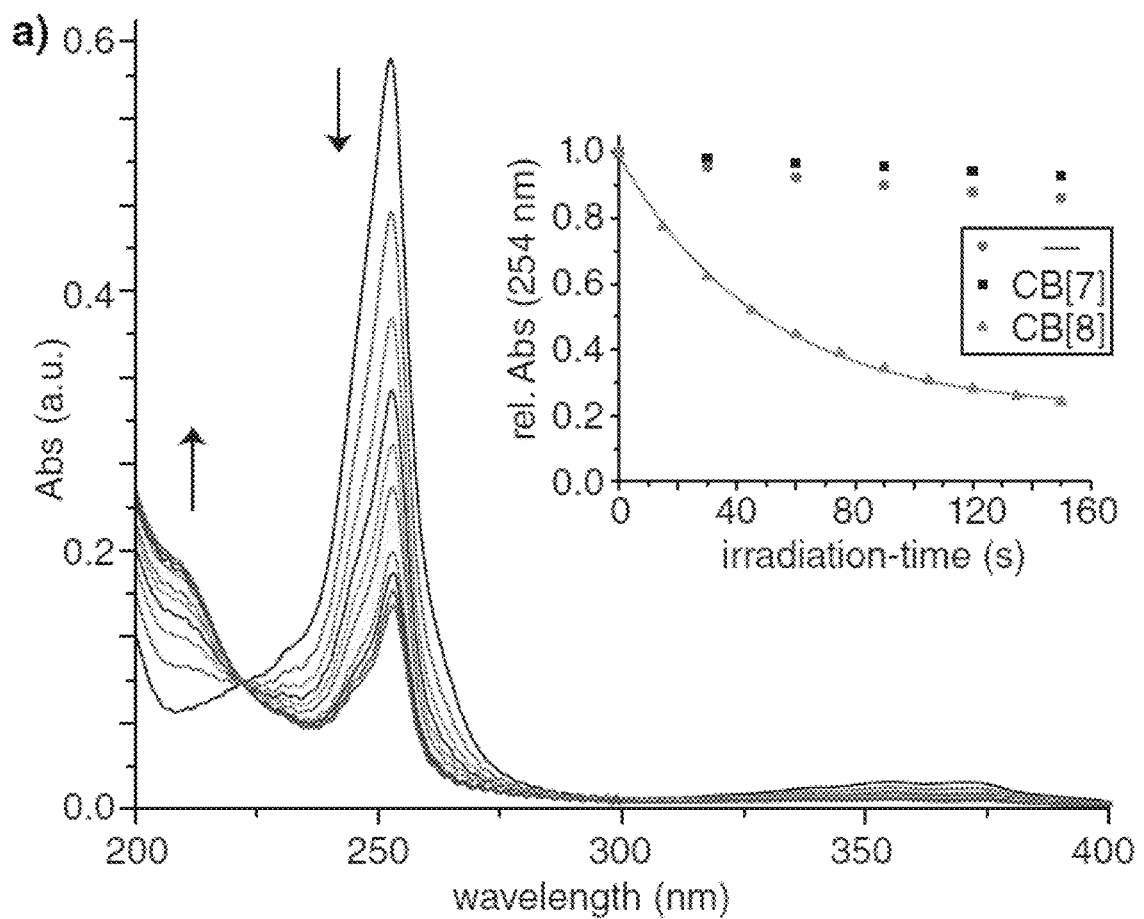
FIG. 20(a) is a UV/vis spectra of a 1a (10 μM) in presence of 0.5 equiv. CB[8] in $H_2O$ upon photoirradiation with a 350 nm light source, spectra taken 15 sec apart. The inset shows the kinetic data in comparison to the control experiments in the absence of the CB[8] host, and in the presence of CB[7]. The solid line shows the best monoexponential fit of the kinetic data.
FIG. 20(b) is a $^1$H NMR spectrum of CB[8]·1a$_2$ (500 μM in $D_2O$) prior to (bottom) and after (top) photoirradiation for 15 minutes. The insets show the aromatic peak region.
Figure 20:
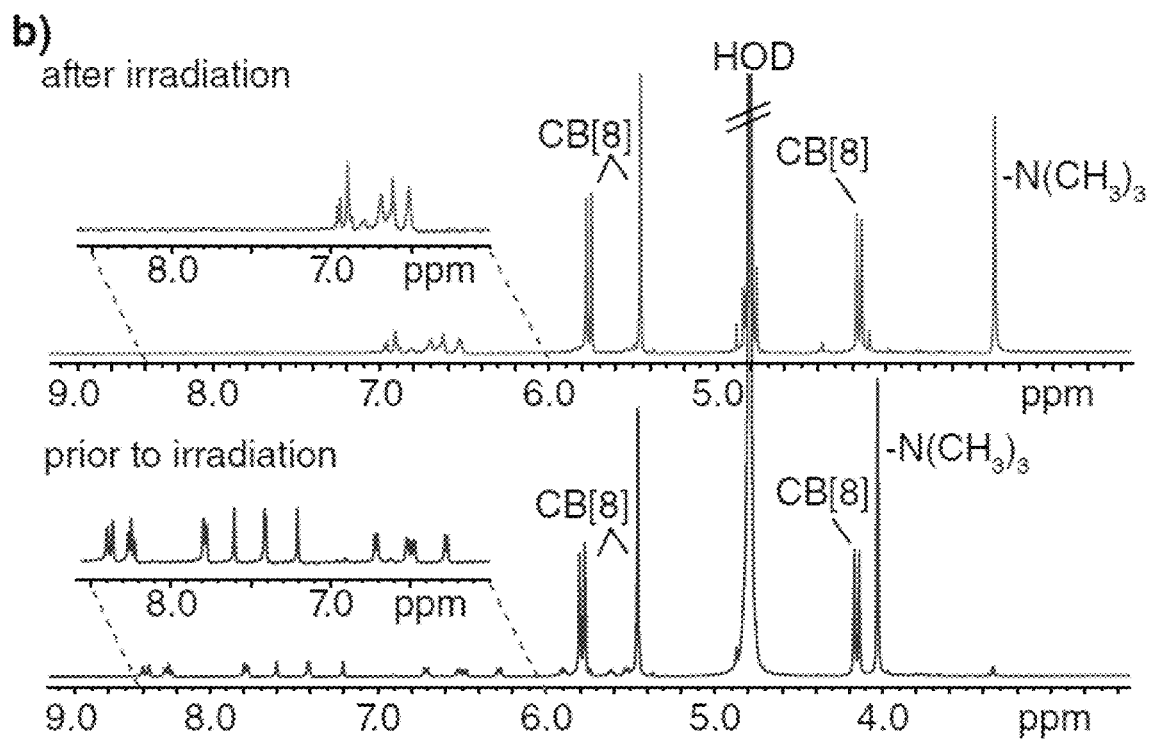

Having established that CB[8] efficiently π-π stacks the anthracene-units of 1a in its cavity, an investigation into the dimerisation of those moieties upon photoirradiation was carried out. It was previously demonstrated by Inoue et al. that the photodimerisation of anthracene-carboxylic acids and their g-cyclodextrin-appended esters in the presence of CB[8] yielded a completely different product distribution than in the absence of the CB[8] host (Yang et al. J. Am. Chem. Soc., 2008, 130, 8574). From the reported binding constants, K$_a$(1)=2.4×10$^5$ M$^{-1}$ and K$_a$(2)=1.4×10$^4$ M$^{-1}$, it is unlikely that the CB[8] host quantitatively preorganised both molecules of neutral or negatively charged anthracene at the experimental conditions used (50 μM of CB[8] and anthracene species) and much more likely that the 1:1 complex was the predominant species in solution. Additionally, no acceleration in the photodimerisation rates were reported in the presence of CB[8], in contrast to previous reports where cyclodextrins were employed as hosts (Tamaki Chem. Lett., 1984, 53; Nakamura et al. J. Am. Chem. Soc., 2003, 125, 966). More recently, a neutral, covalently linked anthracene-π-π-stack dimer was utilised by the same group and photodimerisation in the presence of CB[8] resulted in impressively high ee-values of the asymmetric dimers. We were hoping to shorten the photodimerisation time required for anthracene derivatives, previously reported to take ca. 1 h to reach full conversion through the non-covalent template effect that results from the cooperative binding of positively charged anthracene derivatives with CB[8] (Yang et al. J. Am. Chem. Soc., 2008, 130, 8574). Indeed, photoirradiation of a dilute aqueous solution of 1a (10 μM) and 0.5 equiv. CB[8] with a 350 nm light source led to a rapid decrease in the absorbance of the bands cen tered around 254 nm and 366 nm with an isosbestic point at 222 nm, reaching full conversion within 3 minutes (FIG. 20(a)).

Moreover, the fluorescence emission intensity decreased upon photoirradiation. Both the UV/vis and fluorescence kinetic data yielded an identical rate constant of 2×10$^{-2}$ s$^{-1}$ from mono-exponential fits. Control experiments carried out under identical conditions either in the presence of 1.0 equiv. of CB[7], or in the absence of any host, resulted in only 10% conversion on the same time scale and the rate constants in both cases were an order of magnitude lower than when the photodimerisation was carried out in the presence of CB[8] (see Table 1). The UV/vis spectral features of the product formed when 1a was photoirradiated in either the absence or presence of the CB[8] host were almost identical, suggesting that in both instances structurally similar products were formed. Additional confirmation for the proposed photodimerisation reaction came from ESI-MS measurements of the UV-light treated 1a and CB[8] mixture.

| Compound | Conc. of 1 (μM) | $k_{photo}^a$ ($10^{-3}$ s$^{-1}$) |
|---|---|---|
| 1a | 10 | 3 |
| 1a + CB[7] (1:1) | 10 | 2 |
| 1a + CB[8] (2:1) | 10 | 21 |
| 1a | 1 | 2 |
| 1a + CB[8] (2:1) | 1 | 17 |
| 1b | 10 | 2$^b$ |
| 1b + CB[8] (2:1) | 6 | 9 |
| 1c | 10 | 9$^b$ |
| 1c + CB[8] (2:1) | 6 | 13 |

$^a$Photoreaction rates (350 nm irradiation) were determined from monoexponential fits of the absorbance at 254 nm vs. irradiation time. Identical sample volume and geometry, cuvette and light source were used in all cases.
$^b$Side reactions occur After 15 minutes of photoirradiation only one species was observed in the ESI-MS spectrum, it possessed the correct m/z value and charge state and was identified as the [CB[8]·2a]$^{2+}$ complex; additional peaks including the 1:1 binary complex [CB[8]·1a]$^+$ were present prior to photoirradiation in the ESI-MS but were not observed after photoirradiation. Acetonitrile was subsequently added to the ESI-MS samples in order to release the anthracene-dimer from the ternary CB[8] complex. After photoirradiation the species at the m/z value 236 Da possessed a +2 charge, which is characteristic of the photodimer 2a whereas prior to photoirradiation, the monomeric 1a with a +1 charge was observed at the same m/z value.

Structural information was obtained from 1H NMR experiments (CB[8]: 1a=1:2; 500 μM in 1a). After 15 minutes of photoirradiation, a complete disappearance of the proton signals corresponding to the anthracene reactants in the CB[8] cavity were observed with the emergence of new peaks that can be assigned to a [4+4] anthracene cyclodimer (2a) as can be seen in the $^1$H NMR spectrum in FIG. 20(b). However, in the absence of the CB[8] host, only 50% reactant conversion was reached even after three hours of UV-light exposure. It is also important to note that a larger number of species were formed when 1a was photoirradiated in the absence of the CB[8] host. Subsequent NMR analysis of the uncomplexed photoreaction products further substantiated this finding. From the $^1$H and $^{13}$C NMR spectra of the products, it is clear that a [4+4]-type photoreaction of the anthracene moieties occurred, e.g. the 9- and 10-anthryl protons and carbons shifted upfield into the aliphatic peak region upon photoirradiation. In principle, four different regioisomers could result as racemic mixtures upon dimerisation of 1a. Analysis of the $^1$H and $^{13}$C NMR spectra revealed that an approximately equimolar mixture of two regioisomers was formed in presence of CB[8], whereas in the absence of host all four regioisomers were observed.

The attempted structural assignment of such products by NOESY and COSY NMR was inconclusive, however, it is reasonable to assume that the NMR peaks of the $N(CH_3)_3$ groups are more downfield shifted for the head-to-head than for the head-to-tail dimers on account of charge accumulation on one face of the molecule. Under this premise, it follows from a comparison of all NMR spectra that only the head-to-tail dimers were produced for the CB[8] mediated photodimerisation.

The head-to-tail arrangement of two 1a molecules in the cavity of CB[8] is also energetically strongly preferred on account of minimised charge repulsion and maximised cation-π interactions of the quaternary ammonium groups with the carbonyls on both CB[8] portals, and as such it is most plausible that the head-to-tail templating of two anthracene monomers results in the preferential formation of the head-to-tail photodimer. Thus, from the combination of all the experimental observations, it can be concluded that the non-covalent tethering of two small-molecule anthracenemoieties carrying positive charges with CB[8] accelerates the anthracene photodimerisation reaction and reduces the number of regioisomers and side products.

Host-Guest Complexation and Photodimerisation of an Anthracene-Labeled PEG-Polymer In an effort to exploit the anthracene [4+4] photodimerisation for the ligation of polymeric entities, anthracene end-group labelled PEG (1b) with a molecular weight of 2.4 kDa was synthesised. The spectroscopic signatures observed for the CB[8] titration into to an aqueous solution of polymer 1b were very similar to its small-molecule analogue 1a, e.g. an excimer band around 500 nm in the emission, an isosbestic point at 259 nm in the UV/vis, and the characteristic upfield shifts of the aromatic protons in the $^1H$ NMR spectrum which suggested that CB[8] can tether together two polymeric entities even at remarkably low concentrations (10 μM in 1b). The ternary binding constant, $K_a$(ternary)=$(2.2\pm1.0)\times10^{10}$ M$^{-2}$ for polymer 1 b was found by ITC measurement to be two orders of magnitude lower than that for the small molecule 1a, but is still sufficiently large to enable almost quantitative ternary complex formation in the μM-concentration regime.

Photoirradiation of the CB[8]·1b$_2$ complex with a 350 nm light source was again accompanied by a reduction in the fluorescence intensity, a decrease in the absorbance at 254 nm and 366 nm and the appearance of an isosbestic point at 226 nm, suggesting that the photoreaction of the ternary complexes CB[8]·1a$_2$ and CB[8]·1b$_2$ yielded structurally similar products. The rate of the CB[8] mediated photodimerisation of 1 b is $9\times10^{-3}$ s$^{-1}$, approximately two times slower than for the small molecule 1a at the same concentration (see Table 1).

Further structural verification was obtained by ESI-MS experiments. Unfortunately, no ESI-MS signals could be observed for 1 b (and its CB[8] complex) in neat aqueous solutions, thus, a large excess of acetonitrile had to be added (1:10) prior to injection. As was mentioned before, decomplexation of CB[8] assemblies readily occurs in H$_2$O:acetonitrile mixtures. Consequently, the peaks corresponding to the monomeric 1 b polymer chains were observed prior to photoirradiation (results not shown). After 15 minutes of 350 nm light treatment in the presence of CB[8], the charge, assigned by the isotopic spacing, of the species at the same m/z value had doubled confirming that the photodimer 2b was indeed present (results not shown). The isotopically assigned charges were in agreement with those obtained from the peak-to-peak distance between the polymer-chains consisting of N and of (N+1) monomeric units. For example, ethylene oxide has a monomeric mass M(ethylene oxide) =44 Da and thus a m/z difference of 44 Da and 22 Da prior to and after photoirradiation in the presence of CB[8] yields charges of z=1 and z=2, respectively. A quantitative analysis of 1 b conversion into the photodimerised polymer 2b is not possible using ESI-MS as the signal intensity is highly dependent on the ionization efficiency, and thus on the charge and length of the polymer chains, both of which were doubled upon photodimerisation. Thus, the photodimerisation conversion was monitored by $^1H$ NMR experiments and was found to be quantitative within 15 minutes of photoirradiation when 0.5 equiv. of the host CB[8] was present (500 μM in 1b).

Furthermore, a shift of the retention time was observed in gel permeation chromatography (GPC) experiments, after photo irradiation of the 1b and CB[8] mixture, suggesting that a covalent bond was formed between the anthracene endgroups of two polymer chains. Prior to photoirradiation, the non-covalent CB[8] mediated ternary complex was not strong enough to withstand the separation forces on the GPC columns (at a flow rate of 0.6 mL/min) and resulted in decomplexation into the individual components, i.e. the GPC chromatograms of 1b alone, and the CB[8]·1b$_2$ complex were almost identical.

Photochemical Side Reactions in the Absence of the CB[8] Host

It was suprising that the rate of reactant consumption in the absence of the CB[8] host was similar for the small molecule 1a and polymer 1b, see Table 1, since a bimolecular cycloaddition should be sensitive to the rate of diffusion of the reactants. However, the relatively fast reactant consumption of 1b in the absence of CB[8] is the result of competing side reactions other than the anthracene-dimerisation. For instance, while the absorbance at 254 nm decreased upon photoirradiation, there was an increase in the absorbance in the 265-400 nm region when the sample was irradiated in the absence of CB[8], which is in contrast to the aforementioned findings for 1a, CB[8]·1a$_2$ and CB[8]·1b$_2$. Additionally, reversing the order of photoirradiation and CB[8] addition resulted in markedly different absorption spectra, suggesting that different chromophoric species are formed upon irradiation in the absence and presence of CB[8].

UV-light exposure of an aqueous solution of 1 b led to the appearance of an emission band around 525 nm while irradiation of 1a, CB[8]·1a$_2$ and CB[8]1b$_2$ solutions was accompanied by a decrease in the emission intensity. Additionally, this red-shifted emission band did not vanish if CB[8] was added after UV-light exposure. Structural information from ESI-MS experiments gave further evidence that photoirradiation of 1b in the absence and presence of CB[8] led to completely different photoreaction products. In fact, no evidence for a dimer of 1 b could be found in the ESI-MS spectrum of a photoirradiated 1b solution, however, strong signals that could be attributed to a degraded hydroxyl-terminated poly(ethylene glycol) monomethylether, [HO—(CH$_2$CH$_2$—O)$_n$CH$_3$+Na]+ species were found. In addition, the degraded PEG showed a large polydispersity while the 1 b starting material possessed a much narrower molecular weight distribution. It therefore must be concluded that the photoirradiation of 1b in the absence of the host is accompanied by hydrolytic cleavage of PEG chains at random positions. The cleavage of the anthracene-polymer linkage was also witnessed in $^1H$ NMR experiments, revealing that only a small fraction of the polymer chains carried an aromatic end group after UV/light exposure. As further evidence, the anthracene by-product had precipitated as a red solid from the aqueous solution after photoirradiation of 1 b in the absence of CB[8] host. Moreover, the residual aromatic peaks remained downfield (7.0-9.0 ppm), even after subsequent addition of CB[8], and were thus distinctively different from those of the covalent anthracene-dimers that were formed in the presence of CB[8].

Unfunctionalised PEG does not absorb light at 350 nm and was found to be stable under photoirradiation in a control experiment, thus, the degradation process of 1 b is most likely initiated by the anthryl end group. A photoelectron transfer (PET) from the triazole unit of 1 b to the cationic anthracene-moiety followed by thermal redox or radical reactions is a plausible mechanism for the cleavage of the anthracene-moiety and decomposition of the polymer backbone upon photoirradiation. It is worth mentioning that these side reactions were not likely the result of a photo-oxidation with dioxygen ($O_2$) since UV-light exposure of degassed aqueous solutions of 1 b caused similar spectral changes at comparable rates. From a synthetic point of view, it is of foremost importance that CB[8] complexation of the cationic anthracene moieties completely changed the photochemical reaction pathway from a degradation reaction in the absence to the desired anthracene-dimerisation in the presence of the CB[8] host.

Gel-Formation and Photochemical Crosslinking

Figure 21:
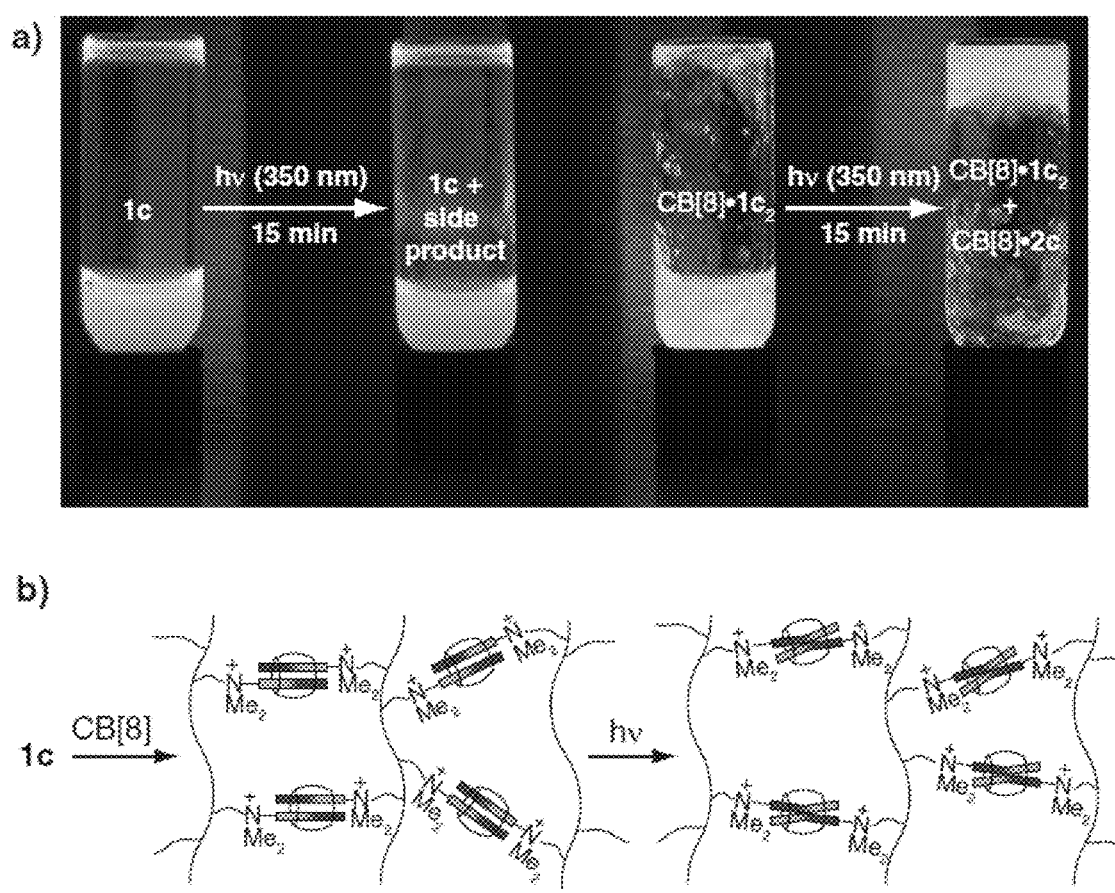
FIG. 21(a) is a series of photographs of 1c at 1.0 wt % in $H_2O$. From left to right: 1c prior to photoirradiation; after photoirradiation at 350 nm for 15 minutes; 1c in the presence of CB[8] (0.5 equiv. per anthracene moiety); after photoirradiation at 350 nm for 15 minutes.
FIG. 21(b) is a schematic representation of non-covalent network formation (gelation) upon addition of CB[8] to 1c followed by photocrosslinking through anthracene dimerisation.

In order to modify materials properties and exploit our anthracene dimerisation findings, side-chain functionalisation of hydroxyethyl cellulose (HEC) with the anthracene-moieties was carried out to induce supramolecular gelation through homoternary complexation upon addition of CB[8] followed by photo-crosslinking. The formation of supramolecular gels through non-covalent 1:1:1 ternary complex formation with CB[8] has been demonstrated (Appel et al. J. Am. Chem. Soc., 2010, 132, 14251; Appel et al. J. Am. Chem. Soc., 2012, 134, 11767). It would be advantageous for certain applications if covalent crosslinks could be introduced after the polymer has self-assembled into a network in order to increase the mechanical stability of the polymer and to slow down gel erosion. Here only two, instead of three, components are needed to trigger gelation: the anthracene-labeled HEC and CB[8], see FIG. 21(b) for a schematic representation. FIG. 21(a) gives a pictorial view of the gels prior to and after photoirradiation. A 1.0 wt % solution of 1c in water is mildly viscous and fluoresces "blue" under UV-light, which is indicative for single anthracene units.

However, when CB[8] was added (0.5 equiv. per anthracene moiety), the fluorescence colour changed from blue to green, representative of the anthracene excimer emission from the 2:1 complex with CB[8] (second vial from the right). The solution also became much more jellylike but did not form a free-standing gel. However, photoirradiation for 15 minutes with a 350 nm light source resulted in a cross-linked polymer to such an extent that it remained a free-standing solid, suggesting that a covalently crosslinked polymer-network was formed (vial on the right in FIG. 21(a)). In the absence of CB[8] host, the photo-crosslinking did not occur to any appreciable extent leaving the viscosity of a 1.0 wt % of solution of modified HEC polymer unchanged (second vial from the left), even if the sample is photoirradiated for one hour. To quantify the mechanical strength of the materials, rheological experiments were carried out.

Mechanical testing of the hydrogels demonstrated the great improvement of the materials properties upon addition of CB[8] and subsequent UV-light treatment, which were far superior to those in the absence of the host.

Figure 22:
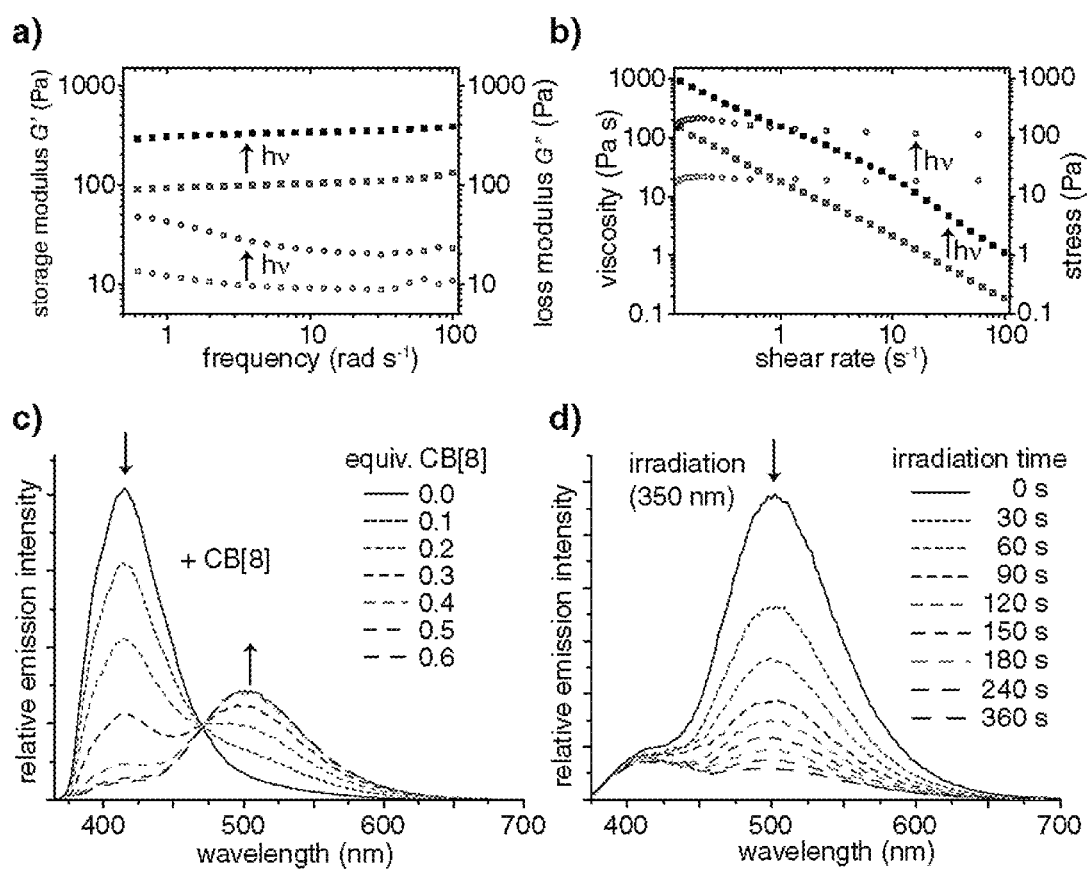
FIGS. 22(a) and (b) Rheological analysis at 20° C. of a hydrogel formed upon addition of CB[8] to a 1.0 wt % solution of 1c in water. Changes upon UV-light exposure (15 min) are indicated by an arrow. Squares refer to the left axis and circles to the right axis. (a) Storage and loss moduli obtained from a frequency sweep performed at 5% strain. (b) Steady-shear rheological measurements. (c) and (d) Fluorescence spectra of dilute aqueous solution of 1c (60 μg/mL) upon (c) addition of CB[8] and (d) subsequent photoirradiation with a 350 nm light source.

The frequency-dependent rheological characterisations performed in the linear viscoelastic region are shown in FIG. 22a. Upon addition of CB[8] to a 1.0 wt % solution of 1c, the storage (G') and loss (G") oscillatory shear moduli were increased by three to four orders of magnitude (compare FIG. 22a and FIG. 23(b)). The frequency response of the CB[8] crosslinked 1c material is characteristic for a soft, highly elastic hydrogel, as the storage and loss moduli curves are rather linear and parallel with tan d=G"/G' 0.15. "Hardening", i.e. a further increase in the G' and G" values by a factor of three occurred upon UV-light treatment (350 nm, 15 min) of the gel while the tan d ≤0.15 value remained low, see FIG. 22a.

Figure 23:
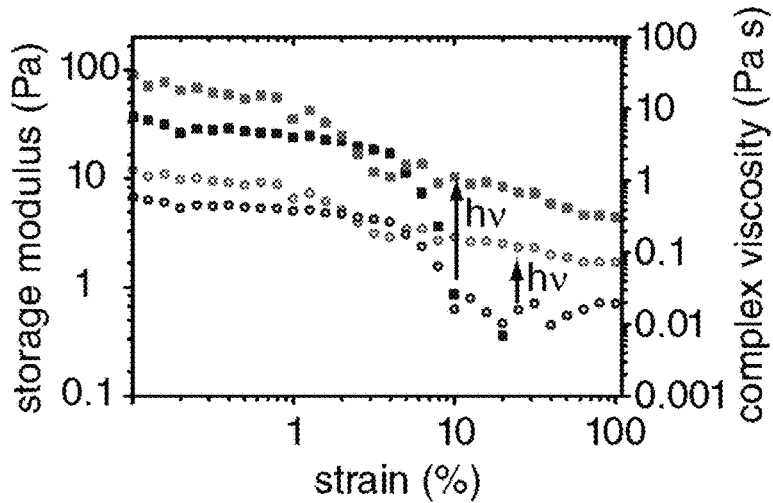
FIG. 23 is a series of graphs relating to the rheological properties of 1c in water. Changes upon UV-light exposure (15 min) are indicated by an arrow. Squares refer to the left axis and circles to the right axis. (a) Storage modulus and complex viscosity obtained from a strain-amplitude sweep performed at 10 rad s$^{-1}$; (b) Storage and loss moduli obtained from a frequency sweep performed at 5% strain; and (c) Steady-shear rheological measurements.
Figure 23:
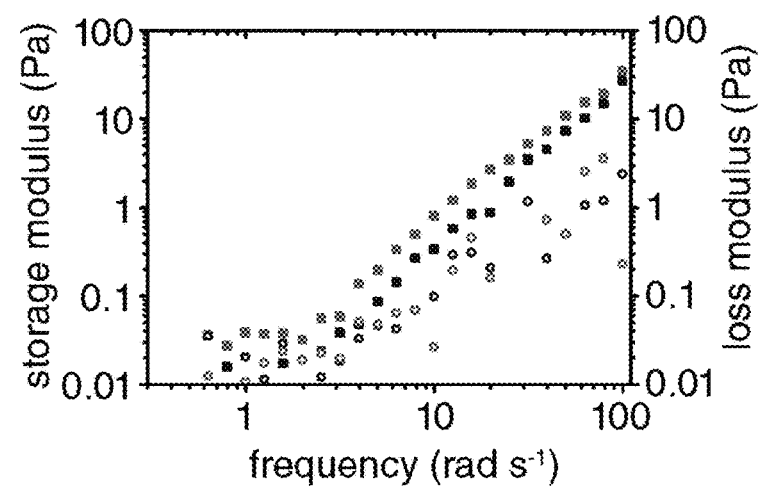
Figure 23:
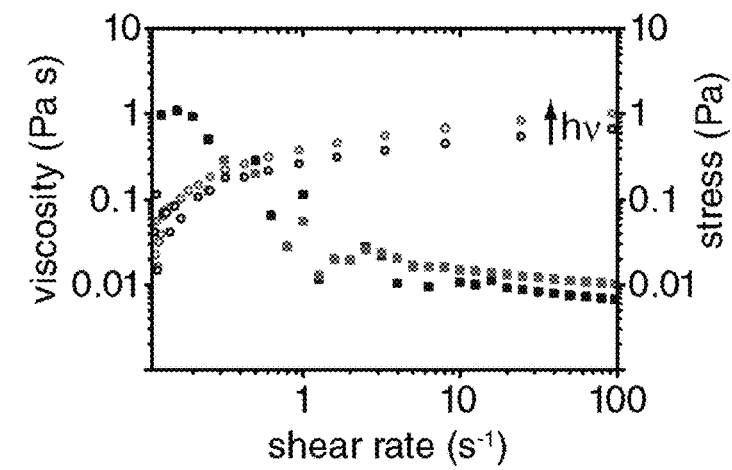
Figure 24:
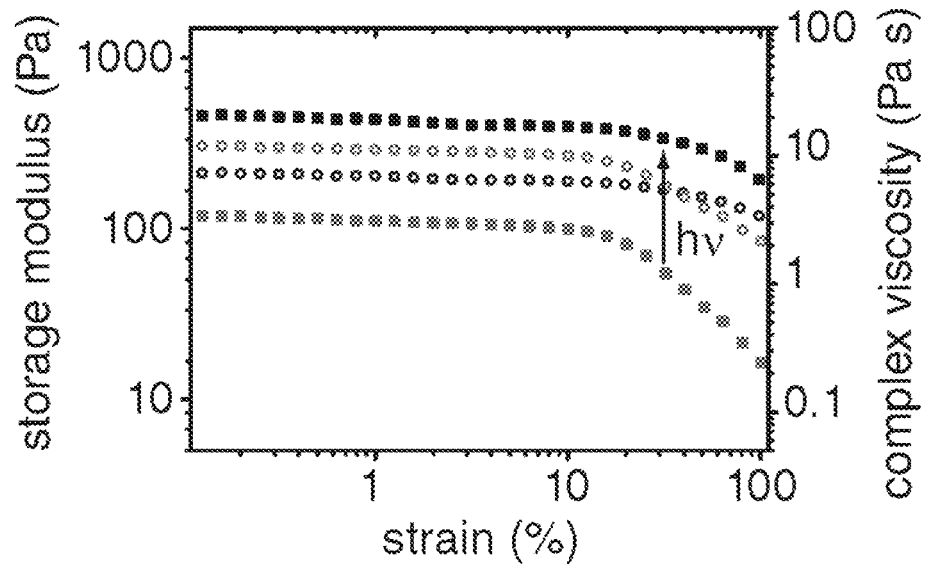
FIG. 24 shows the oscillatory rheological analysis at 20° C. for the hydrogel formed upon addition of CB[8] to a 1.0 wt % solution of 1c in water. Storage modulus and complex viscosity obtained from a strain-amplitude sweep performed at 10 rad s$^{-1}$. Changes upon UV-light exposure (15 min) are indicated by an arrow. Squares refer to the left axis and circles to the right axis.

Conversely, in the absence of the CB[8] host, hardly any change in the rheological characteristics of the aqueous 1c solutions was observed upon UV-light exposure, maintaining a typical fluid-like behaviour (see FIG. 23). Moreover, both the non-covalently bound and photo-crosslinked hydrogels displayed a broad linear viscoelastic region (see FIG. 24) with breakdown of their gel structure at strain amplitudes above 10% while other supramolecular hydrogels typically fall apart at much lower strains (see Appel et al., J. Chem. Soc. Rev. 2012, 41, 6195 and Mynar et al. Nature 2008, 451, 895).

It is worth noting that the UV-light treatment further improved the strain resistance of the gel. The effect of photo-crosslinking of the anthracene moieties in the presence of CB[8] was also tested by steady-shear measurements, that displayed an increase in the viscosity (h) of the hydrogel by a factor of 80 upon photoirradiation, depicted in FIG. 22b, while the 1c solution in the absence of CB[8] maintained its low viscosity (FIG. 23(c)). When the CB[8] addition and photoirradiation experiments were carried out under a high dilution of 1c (60 µg/mL), solution spectroscopic techniques such as UV/vis and fluorescence could be utilised.

Figure 25:
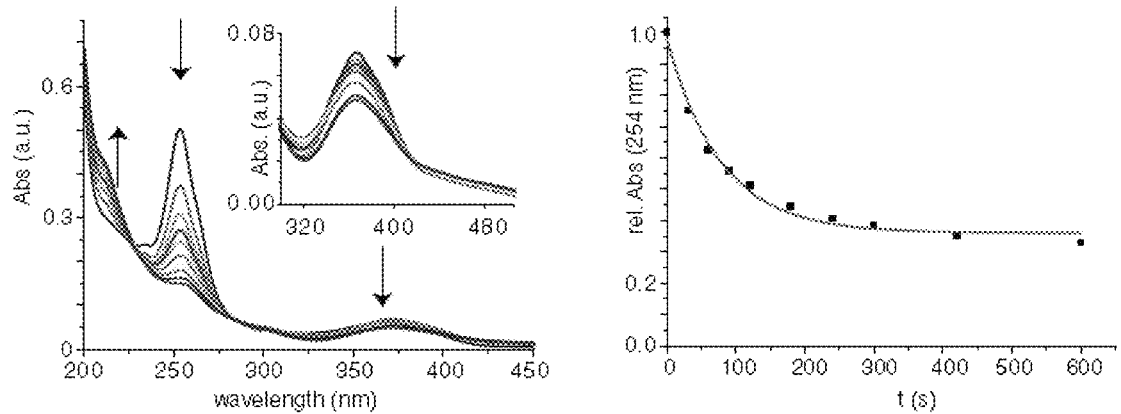
FIG. 25 show the UV/vis spectra for 1c (60 μg/mL in water) upon photoirradiation (350 nm) in (a) the presence of 0.5 equiv. CB[8] and (b) in the absence of the CB[8] host. The plot on the right shows the normalised absorbance at 254 nm as a function of irradiation time. The solid red line shows the best monoexponential fit of the kinetic data.
Figure 25:
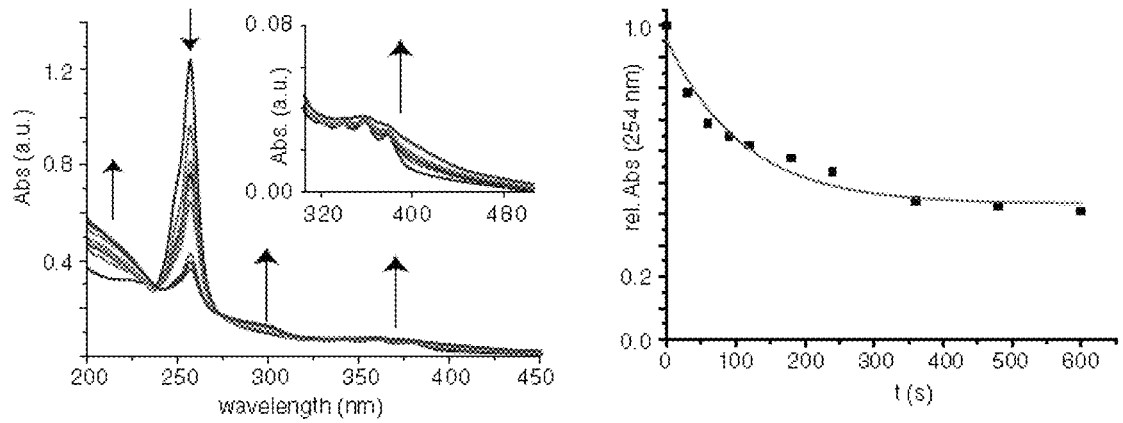

Titration of CB[8] into an aqueous solution of 1c showed essentially the same characteristics as were seen for the complexation of CB[8] with 1a and 1 b (data not shown). Most importantly, maximum photodimerisation occurred within 5 minutes of photoirradiation in the presence of CB[8], as was determined by UV/vis (FIG. 25(a)) and fluorescence spectroscopy (FIG. 22d), which resembles the results for the photoirradiation of the CB[8] complexes with 1a and 1b. Not surprisingly, the rate of reactant consumption was also very high in the absence of the CB[8] host (Table 1) since the multiple anthracene side chains of 1c are covalently held in close spatial proximity. However, in the absence of CB[8] there was again evidence for the occurrence of photochemical side reactions as red-shifted emission and absorption bands emerged upon photoirradiation (see FIG. S25(b)). Consequently, host-guest complexation of the anthracene moieties with CB[8] does not only induce non-covalent network formation and accelerate the subsequent photochemical dimerisation, but also protects the chromophore from leading to undesirable side reactions that can result in material deterioration and thus impede the gelation process.

Moreover, CB[8] complexation suppressed photochemical side reactions including degradation of the polymer backbones that were readily observed upon irradiation in the absence of the CB[8] host.

The rheological experiments were performed as described previously.

REFERENCES

All documents mentioned in this specification are incorporated herein by reference in their entirety.

Appel et al. *J. Am. Chem. Soc.* 2010, 132, 14251-14260
Appel et al. *J. Am. Chem. Soc.,* 2012, 134, 11767
Appel et al., *J. Chem. Soc. Rev.* 2012, 41, 6195
Benguigui et al. *Euro. Phys. J. B.* 1999, 11, 439-444
Biedermann et al. *Macromolecules* 2011, 44, 4828-4835
Coulston et al. *Chem. Commun.* 2011, 47, 164-166
Danil de Namor et al. *Chem. Rev.* 1998, 98, 2495
Dsouza et al. *Chem. Rev.* 2011, 111, 7941
Esposito et al. *Int. J. Pharm.* 1996, 142, 923
Estroff et al. *Chem. Rev.* 2004, 104, 1201-1217
Gokel et al. *Chem. Rev.* 2004, 104, 2723
Greef et al. *Chem. Rev.* 2009, 109, 5687-5754
Greenfield et al. *Langmuir* 2010, 26, 3641-3647
Hartgerink et al. *Science* 2001, 294, 1684-1688
Heitmann et al. *J. Am. Chem. Soc.* 2006, 128, 12574-12581
Horkay et al. *Macromolecules* 1991, 24, 2896-2902
Horkay et al. *Polymer* 2005, 46, 4242-4247
Hunt, J. et al. *Adv. Mater.* 2011, 23, 2327-2331
Jiao et al. *J. Am. Chem. Soc.,* 2010, 132, 15734
Jiao et al. *Org. Lett.* 2011, 13, 3044
Katakam et al. *Int. J. Pharm.* 1997, 152, 53-58
Kim et al. *J. Am. Chem. Soc.* 2000, 122, 540-541
Koopmans et al. *Macromolecules* 2008, 41, 7418-7422
Kretschmann et al. *Angew. Chem. Int. Edit.* 2006, 45, 4361-4365
Lagona et al. *Angew. Chem. Int. Ed.* 2005, 44, 4844 Large Array Manipulation Program (http://www.ill.fr/data_treat/lamp/lamp.html; D. Richard, M. Ferrand and G. J. Kearley, *J. Neutron Research* 1996, 4, 33-39)
Lee et al. *Chem. Commun.* 2002, 2692-2693
Li et al. *Biomacromolecules* 2005, 6, 2740-2747
Liu et al. *Chem. Eur. J.,* 2011, 17, 9930
Loh et al. *Biomacromolecules* 2007, 8, 585-593
Loh et al. *Biomaterials* 2007, 28, 4113-4123
Loh et al. *Biomaterials* 2008, 29, 2164-2172
Loh et al. *Biomaterials* 2008, 29, 3185-194
Loh et al. *J. Control. Release* 2010, 143, 175-182
Loh et al. *J. Mater. Chem.* 2011, 21, 2246-2254
Loh et al. *J. Phys. Chem. B* 2009, 113, 11822-11830
Loh et al. *Macromol. Symp.* 2010, 296, 161-169
Lutolf. *Nat. Mat.* 2009, 8, 451-453
Mynar et al. *Nature* 2008, 451, 895
Nakamura et al. *J. Am. Chem. Soc.,* 2003, 125, 966
Nochi et al. *Nat. Mat.* 2010, 9, 572-578
Peppas et al. *Annu. Rev. Biomed. Eng.* 2 2000, 9-29
Pezron et al. *Polymer* 1991, 32, 3201-3210
Reczek et al. *J. Am. Chem. Soc.* 2009, 131, 2408-2415
Rekharsky et al. *Chem. Rev.* 1998, 98, 1875
Ritger et al. *J. Controlled Release* 1987, 5, 23
Ritger et al. *J. Controlled Release* 1987, 5, 37
Sijbesma et al. *Science* 1997, 278, 1601-1604
Staats et al. *Nat. Mat.* 2010, 9, 537-538
Tamaki *Chem. Lett.,* 1984, 53
Uzunova et al. *Org. Biomol. Chem.* 2010, 8, 2037-2042
Van Tomme et al. *Biomaterials* 2005, 26, 2129-2135
Wang et al. *Nature* 2010, 463, 339-343
WO 2009/071899
WO 2011/077099
Wojtecki et al. *Nat. Mat.* 2010, 10, 14-27
Wu et al. *Langmuir* 2008, 24, 10306-10312
Yang et al. *J. Am. Chem. Soc.,* 2008, 130, 8574

The invention claimed is:

1. A hydrogel having a supramolecular cross-linked network obtainable from the complexation of an aqueous composition comprising a host and one or more polymers having suitable guest functionality,
wherein the hydrogel holds a component,
wherein the host is cucurbit[8]uril,
wherein the one or more polymers have suitable guest functionality,
wherein the one or more polymers having suitable guest functionality for cucurbit[8]uril have a weight average molecular weight of 50 kDa or more,
wherein the one or more polymers having suitable guest functionality are hydrophilic,
wherein the hydrogel has a dominant storage modulus over loss modulus across all strain values in the range 0.1 to 100 rad/s as measured by frequency sweep measurement at 25 degrees centigrade at a strain amplitude of 5 or 10%, and
wherein the one or more polymers having suitable guest functionality are selected from the group consisting of homo polymers of vinyl alcohol,
hydroxyethyl cellulose,
homopolymers of vinyl benzene,
cellulose derivatives,
hyaluronic acid,
carboxymethyl cellulose,
polyacrylamide, and
homopolymers of vinylbenzyltrimethyl ammonium chloride.

2. A method for the preparation of a hydrogel holding a component, wherein the method is independently selected from method A or B:
(A) the method comprising the step of bringing into contact in an aqueous solution a mixture of a host, a component, and one or more polymers having suitable guest functionality, thereby to generate a hydrogel holding a component, wherein the host is a cucurbit[8]uril, and the one or more polymers having suitable guest functionality have suitable guest functionality for cucurbit[8]uril, the one or more polymers having suitable guest functionality have a weight average molecular weight of 50 kDa or more, the one or more polymers having suitable guest functionality are hydrophilic, wherein the hydrogel has a dominant storage modulus over loss modulus across all strain values in the range 0.1 to 100 rad/s as measured by frequency sweep measurement at 25 degrees centigrade at a strain amplitude of 5 or 10%, and the one or more polymers having suitable guest functionality are selected from the group consisting of homopolymers of vinyl alcohol, hydroxyethyl cellulose, homopolymers of vinyl benzene, cellulose derivatives, hyaluronic acid, carboxymethyl cellulose, and homopolymers of vinylbenzyltrimethyl ammonium chloride; and
(B) the method comprising the steps of providing a hydrogel having a supramolecular cross-linked network obtainable from the complexation of an aqueous composition comprising a host and one or more polymers having suitable guest functionality, and agitating that hydrogel in the presence of a component, thereby to incorporate the component into the hydrogel, wherein the host is a cucurbit[8]uril, and the one or more polymers having suitable guest functionality have suitable guest functionality for cucurbit[8]uril, the one or more polymers having suitable guest functionality have a weight average molecular weight of 50 kDa or more, the one or more polymers having suitable guest functionality are hydrophilic, wherein the hydrogel has a dominant storage modulus over loss modulus across all strain values in the range 0.1 to 100 rad/s as measured by frequency sweep measurement at 25 degrees centigrade at a strain amplitude of 5 or 10%, and the one or more polymers having suitable guest functionality are selected from the group consisting of homopolymers of vinyl alcohol, hydroxyethyl cellulose, homopolymers of vinyl benzene, cellulose derivatives, hyaluronic acid, carboxymethyl cellulose, and homopolymers of vinylbenzyltrimethyl ammonium chloride.

3. A method of delivering a component to a location, the method comprising the steps of:
(i) providing a hydrogel holding a component, wherein the hydrogel has a supramolecular cross-linked network obtainable from the complexation of an aqueous composition comprising a host and one or more polymers having suitable guest functionality;
(ii) making the hydrogel available at a target location, wherein the host is a cucurbit[8]uril, and the one or more polymers having suitable guest functionality have suitable guest functionality for cucurbit[8]uril, the one or more polymers having suitable guest functionality have a weight average molecular weight of 50 kDa or more, the one or more polymers having suitable guest functionality are hydrophilic, wherein the hydrogel has a dominant storage modulus over loss modulus across all strain values in the range 0.1 to 100 rad/s as measured by frequency sweep measurement at 25 degrees centigrade at a strain amplitude of 5 or 10%, and the one or more polymers having suitable guest functionality are selected from the group consisting of homopolymers of vinyl alcohol, hydroxyethyl cellulose, homopolymers of vinyl benzene derivatives, cellulose derivatives, hyaluronic acid, carboxymethyl cellulose, and homopolymers of vinylbenzyltrimethyl ammonium chloride; and
(iii) releasing the component from the hydrogel.

4. The hydrogel of claim 1, wherein the weight average molecular weight of the one or each of the polymers having suitable guest functionality for cucurbit[8]uril is 100 kDa or more.

5. The hydrogel of claim 1, wherein the component is a therapeutic compound.

6. The hydrogel of claim 5, wherein the therapeutic compound is a biological molecule.

7. The hydrogel of claim 6, wherein the biological molecule is selected from the group consisting of a polynucleotide, a polypeptide, a cell and a polysaccharide.

8. The hydrogel of claim 6, wherein the biological molecule is selected from the group consisting of DNA and RNA.

* * * * *